United States Patent
Qin et al.

(10) Patent No.: US 12,209,247 B2
(45) Date of Patent: Jan. 28, 2025

(54) TARGETED INSERTION SITES IN THE MAIZE GENOME

(71) Applicant: SYNGENTA PARTICIPATIONS AG, Basel (CH)

(72) Inventors: Yinping Lucy Qin, Research Triangle Park, NC (US); Mark Rose, Research Triangle Park, NC (US); Zhongying Chen, Research Triangle Park, NC (US); Heng Zhong, Research Triangle Park, NC (US); Weining Gu, Research Triangle Park, NC (US); Wenling Wang, Research Triangle Park, NC (US); Qiudeng Que, Research Triangle Park, NC (US); Ailing Zhou, Research Triangle Park, NC (US); Mary-Dell Chilton, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 61 days.

(21) Appl. No.: 17/822,537

(22) Filed: Aug. 26, 2022

(65) Prior Publication Data

US 2023/0114951 A1    Apr. 13, 2023

Related U.S. Application Data

(62) Division of application No. 16/757,851, filed on Apr. 21, 2020, now Pat. No. 11,459,577.

(51) Int. Cl.
*C12N 15/82* (2006.01)
*A01H 6/46* (2018.01)

(52) U.S. Cl.
CPC ....... *C12N 15/8213* (2013.01); *A01H 6/4684* (2018.05)

(58) Field of Classification Search
None
See application file for complete search history.

(56) References Cited

U.S. PATENT DOCUMENTS 9,970,001 B2  5/2018  Miller
2015/0353917 A1* 12/2015 Miller .................. C12N 15/102
                                                  435/441

FOREIGN PATENT DOCUMENTS

WO  2015/066636 A2  5/2015
WO  2016106121 A1   6/2016

OTHER PUBLICATIONS

Cantos, Christian, et al. "Identification of "safe harbor" loci in indica rice genome by harnessing the property of zinc-finger nucleases to induce DNA damage and repair." Frontiers in plant science 5 (2014): 88716. (Year: 2014).*
Wilson, R K. "*Zea mays* Cultivar B73 Chromosome 6 Clone CH201-148j19, *** Sequencing." National Center for Biotechnology Information, U.S. National Library of Medicine, Sep. 23, 2013, www.ncbi.nlm.nih.gov/nuccore/545260365. (Year: 2013).*
GenBank Submission AC155451, *Zea mays* Strain B73 clone ZMMBBb0369D20 (Jan. 25, 2005).
International Seach Report for International Application No. PCT/US18/65114, mailed Apr. 1, 2019.
Blast N RID: CS5569DZ01R (Year 2021).
GenBank: AF464738.1, "*Zea mays* cultivar B73 putative gag protein, putative gag-pol precursor, putative transposase, putative copia-type pol polyprotein, putative copla-like retrotransposon Hopscotch polyprotein, putative gag protein, putative prpol, putative prpol", Jan. 19, 2006 (Year: 2006).
Clark, Pattern of diversity in the genomic region near the maize dornestication gene tbl, Proceedings of the National Academy of Sciences, Jan. 20, 2004, (Year: 2004).
Genbank AC208423, *Zea mays* cultivar B73 chromosome 4 clone CH201-244D17, Sequencing in progress, 2 unordered pieces, NCBI, https://www.ncbi.nlm.nih.gov/nuccore/AC208423.3, Jul. 29, 2008 (Year 2008).

* cited by examiner

*Primary Examiner* — Weihua Fan
*Assistant Examiner* — Brian James Sullivan
(74) *Attorney, Agent, or Firm* — Dale Skalla

(57) ABSTRACT

The present invention relates to methods and compositions for targeted insertion of polynucleotide molecules into ideal target sites in the genome of a maize plant. The present invention relates to maize recombinant molecules comprising heterologous sequences and also to methods of integrating a DNA of interest into a target maize genomic locus in a maize genome. The present invention also relates to regenerated maize plants or plant parts comprising the recombinant molecules and/or a DNA of interest.

19 Claims, No Drawings

Specification includes a Sequence Listing.

SEQUENCE LISTING

```
Sequence total quantity: 105
SEQ ID NO: 1            moltype = DNA  length = 1772
FEATURE                 Location/Qualifiers
source                  1..1772
                        mol_type = genomic DNA
                        organism = Zea mays
SEQUENCE: 1
gtacgtaacg aatctacgtt aagatcaatc tcttcgtgga gattcggatc cttttacttc   60
tagacgaggg aaggaaagtt tccctgggtc gtgacagtta gttgggccgt gtactgggtg  120
tagaatgtca ggcgcgttcc aagtatcgct aaagcccaag tggcaggctg atcgatgcat  180
cttggcccat tagtcggata ggtggttgct cgtcctagac cacaatggtc cagcagtcca  240
tgaaaccatc aggcccacaa gtttgttccc accgaaaata gtttccgctc cgcctccgag  300
cccgcccggc ccggctgccc gccaccgccg atctccccca ccgcaaccca ccttgagacc  360
tgagcgagcg tcaccccgac gcgcgggtcg accccgaagc cgccggcgag ccacagctag  420
catacgcgga cgatccgggg actctgctcg cctcgtgatt gctgctggct tgccggtggt  480
gtcatcggta cgtgttctgt atgaccgaat tcctcgttgg cggcagcagc agagaatgca  540
gggtggtgcc gcgtatgtag cagcgcttgc tggttgcgcc gccgcacagc agctgagcgc  600
ctgactggga gcctcagatc ctacgcgcat gtatgcatgt gacgcgccat gcattaaccc  660
catcagagct cagggtttca gctttcactt caggagtcag gatcagaatt cagaaagggt  720
ttcagttgag cctacaacct gtcaacctcc tatatacata catagggctt gcttcgttcg  780
ctcgtcgtcg atggacagac agatgcggta tgccgctcat gcatgttagc tgttgttgtg  840
tgccctccat cagttcgatt atggattttt aagtgggcat gcagcatgta cgcgtgtacg  900
tacgcggcgc cgtgacgacg ccgcgcccg accgcgaccg gccagcaggc cgagacgctc  960
gccgcctgat tcgcgcgcgc gccatgccca tgctgtgttg ctagctgctc aaactcacat 1020
gcctccgatc cggagtccgg ctagcaccta gcagcgagct tcgctcacat tccttgcctg 1080
cgtgcggtgc gtgcagtaca gcgactgcag cgagtttcgt tcttcagaat tcgccgacta 1140
ctggatcgat tcatagtttc agacttaaga agaaaggact aaactgaaag ggatgcgatg 1200
tgccctctca aggactgaag cgtcctttt ctctcaaacg acgacaggag gggggccgcg 1260
ccggccgggc cagcgtgcgt gctcatcgcc gccgcagcag ggatcggaga cgggagggac 1320
```

```
cgccccacct gcctggcaag ctcacggcga ttacagttgc gttacaggga ggatcgatgg   1380
cagctgcagg gcgctgtgat gcatatgctg atgcctgcac agtggcggag ttatgtgtgc   1440
gggaacaaac gaacaggacg ccgggaggcc aggccagcgt gctctcgcta acggaggcag   1500
gcgcagcgca aggacctcat ccatccaccc ctccacaccg tgcccaccac caccggttct   1560
ggcagagttt caggcagctg caactgcatg caatgcaatg cagcagcagg gagcgccggc   1620
agtgccttca ttttttttt  gtgctccacc cccacagctc cactgcatgg tgcgtggcgc   1680
atgccatgga agcactacga cgcaacactg gtcggcgtaa acacatgcac gaggaagagg   1740
tggaggagag ggcttgcttt tcacgtgac  ac                                 1772

SEQ ID NO: 2           moltype = DNA  length = 1961
FEATURE                Location/Qualifiers
source                 1..1961
                       mol_type = genomic DNA
                       organism = Zea mays
SEQUENCE: 2
gcaaatatga cgaagttaaa acgtgaaatc aagccactgg gatacatgga catttgagat    60
cagtccagat ctctctctct tttttgctg  cccagtgctt gctgcagttc caaccattat   120
gctgtcatat gttcatatat tgagttgtga tgttcatgta tcatgaatac acaacagtgc   180
taaaatgttt agaaatcagt ctagctggta ggaagcttaa tggaaattca tcatatcttc   240
cctgcgacct gaatttgggg cttccaaact acctgaagtt ggttacagat tctagattac   300
tgtttggtga tattaggact ggaactctat tctggcttgt agcttctcaa gtcattggaa   360
gtgatttaga caaggcctag attttgtt   gttggaccaa tttttaaatc tgaagcttgc   420
tgcaattaaa gcagataatg tacataggca gcaggttagt ttagctacgc aggctgccat   480
tccaaacaca tcgttgcagt gaagcatcaa atctaattaa aacatgtatg ataaacatgt   540
catagcttac ctatgccaat aagcagaata tttctcaact atatctatag gttgctgcaa   600
gcaatattga atttgaagga acttgcccaa gtttcatttt ataacacatt gaggtgtcat   660
gtcgattaaa ttaaatggag ttgccaattc atatcacatt tttttattgt acctccactt   720
agcactttttg caatactttc aagaacgtta ggtctttggg tgggtggtgg taatatactc   780
gtcttcaggg ggatgccaca tgaagaaaca aatgcagtcc ttttagcttc attgttagag   840
gcttttccagt ccttttgaga tgagctcttc aatacactgc ttgtacttta tatcatttga   900
tcttaaatac tttgtgacaa acccctgtt  cttccaattt aatctggtta agtgcagtag   960
agcatctctc tgcatgactg ttgcataagt ttgctggtt  cttgtgagtt catttcatag  1020
caggataatg caataccaaa gtgatgcttg tatacattat actggcatac tgcatccact  1080
cttcctatat aagcaacata aattaattac cctaggggg  tcatctgttg cccattgggc  1140
ttgccttgac tatcggcaat cgttcctcta gcagcagaat ggggaacccc ttaatggcat  1200
tgaaaacggt accctttagt ggatattgag attttacttt taagcttttg ggcattgtat  1260
tcaatcactg atatttccat aaaaaggata accacaggtt gaactttaca atggggtttg  1320
cagttactag cataatatgg ccctgttaag cggacaagtg ctggtaaatt tttatttcca  1380
tttgccacac ataattctta gttctattta tttactatat tagctttttct tgtgttgctt  1440
atggctggat acaagctcag cgtgatgtta gtaactggcc tggtcattag caatcgtatg  1500
gaaaccaggg acatggaata ggaactctct tttgtgaaca atagctgctg tcagcctgtc  1560
agttttactc tgtgcgcatc taatgcatga tagattgaaa cacatcggat gtgatgttta  1620
aggaatcttt tgtatcggat ctggatcata tggtcacaac cttcccactg taaaacacgt  1680
cttgttagct tttctgcagt cttgtctgat aattccattt gcatgccatg acaaccgaca  1740
acatgaacac aaacgacata ataataatgg caatagtgca tctataccta gtctcttttg  1800
gcttgccaat gtccatttgt gttttggtcaa tacctcggag ggactcccaa cacgtatatt  1860
ctatgaagtt catcttcaga gttatgttat gcccccctcc cacccccaa  tgaaacttga  1920
caactacatt ttttggtgg  ctctgtatga tgaagctgtt a                      1961

SEQ ID NO: 3           moltype = DNA  length = 1763
FEATURE                Location/Qualifiers
source                 1..1763
                       mol_type = genomic DNA
                       organism = Zea mays
SEQUENCE: 3
tgtagggaat aatatcattg tgtcttccct agttcgtagt cctgaaatgg tcatcagcca    60
ccaaagatta ttcactttga accaactgtt ttttttataa aaaagagcc  acaaatcgag   120
atgccgaatt caccaatgcg ctacgttttc agtgacactg aggaacagtt tatcagggag   180
cgaggggga  aacgccgaaa cggcatcgga atcggaatga gaagcagaat ggggatttga   240
atgctgcggc ctgcgagagg gagcggagtg gaatgaatg  tccccgcag  gtgccacccc   300
tacgagccgt ccaaaaccag gtcgaaattt acgccgccaa aagggccacg aaatccagaa   360
aaccccagag gaataaaggg ctctccgctt gggggccgg  gtgatgagag gtggatatat   420
atcttttcat gtcggtttcg gcctctgtgg gtaagagtg  tgggggtga  cgctaatctc   480
cacgcgcgcg cggctcgctc gcgtccggtc cggcgctccg ctacgggatg catgtgcgga   540
tgtatgcctg ctgcctgcat gcgagattcc gacggcgacg caagagttat ctggaactcc   600
acggccgcag ctagccggcg gcccaaccag ttctttctcc ggagatgaca gcaaaaagac   660
ctggattcga atgcttcacg gccggggct  gtcactcccc gctctcccg  gccggtgatg   720
cgatcgaaga gagcagagca atccaacggg cctgtccatt tccaaagcat ttccaaagca   780
aattccgaga catacatata tgccggcggg ggcaagttcg catgcgctcg cgtggcgtgg   840
cgtggcgctt tcgaatttcg atccggagca ggacgacgac gagccttgct cttgctatcg   900
agcacgacga tatattccat gcagcagcaa aatatgctaa cccacattaa caggctaggc   960
acagcaggtt tagcatggct ctgtatgtaa tacgtaaaat ggacagccat ggttttggtt  1020
tcgctagctt cgaggtcaaa agggtattaa cataattgac cttttaatca cgtacgtacg  1080
tcgaccatgg ccaggctgga ttcgaaaaaa aaagaggcta cttacggtat atatgtgatt  1140
aaactatgcc acaaaaaaaa actttgcttt gcagggggct taatggggga gggaatatat  1200
ctgaaaggga cggagcgaca gacgggagag attgcgtaag ggctaagtga cgcctttcga  1260
cggcgagctt ttttttgggggg ggctgcagtt gtgttgagag caacgtcaga cagacagaga  1320
gtaacggatg gcgataacga actcctcgga acagtgtagt gtagcggcag ggatggtttt  1380
tggaaagctg ggttttttttt tctttttcttc tggaaacaaa ttaaggccgg catgctatgc  1440
```

-continued

```
tactgagtgc tggccaggcc atcagtgacg gatgcacagg aggagcacct agtcctacgc 1500
aggaggacag atcgagcccc ggccggctgg ttgcacgtac ttattactac tagtgatata 1560
aaagcgagga gggacaggat ctaacatcta attgcctgta cgtactgaat atatgtcttg 1620
gtcgtcctgt tgtggagttg accagaggcc ggcgacatca tgtgacgcaa ttgtccagcc 1680
tgaaaaggcc aacattatca acactgcata ccttttctgc cgttggtaac aaacaaaaga 1740
ataatactgt agtagttttt tta                                     1763
```

SEQ ID NO: 4        moltype = DNA   length = 2026
FEATURE             Location/Qualifiers
source              1..2026
                    mol_type = genomic DNA
                    organism = Zea mays
SEQUENCE: 4

```
acatatcata tcgtcatccc atagtacaat gatttgctca aaaagcctag gctttaagga 60
caagttttga cacataaatt tatcgacgac aaaattttat gcccacaaac atgtgagaga 120
aacaaaggaa catgctaaaa gatagaatac atgttatcaa acattttca agatttcata 180
atttaggaga tatacatgcg acttatcaaa atctctacct gctactggct tgtgtttttc 240
tataaaaagt attctcgact attccttc ctacgactga ctcccacctg gtagataccc 300
tcattcactt tattggacaa ttgagttttt cttttgtca tgaagaccaa gaccttgtta 360
ccctttaata ttaagtaagg aataaacatc cttcaagaaa ataaaccac ctataaaaac 420
ttcttcaata ttcgttgaag tatttcttca ttaaagttca ggtattctaa aggtttggag 480
aagttctaca aaaaatgtat ataaaatggt gcaacgtgat tcttgtagaa atctctccat 540
tgtctttctt aatttttgaat ggaacaagga ctcaaaattt gagagtaatt aagtatatgg 600
gagaagctta tgtgctagca gattaggagt cattttttg cttagagtat aaaatgtga 660
agtaagtcat ctaactcatg aatcattgta ccatgtgcac atgtagtgcc taacacctat 720
gcgatgtaga catgggatgt taaacctaga gtagtcatag tgtgactttg ttttcgcaaa 780
aaaacaacta acattactag ggccagattg gcgtaagaa agactacacc atcaaaattt 840
agaaaggtca tgcatagatt gtatcacaaa aatactagat gttctatgat taaaaacgt 900
tccaagaacg tggtgtcttt gttctttgac aagctattgg gcctgtacag gatcagctaa 960
ccccacatgc gctacaagat ctcacttgcc ctatccatct acatccaccc cttccttctt 1020
tcttttctcca tcgcaccata tttttcctt cacccacatg gaagcacatg tctttttacc 1080
tttagctatc acattaggaa ggtgagtgtt gtctctcctc tacaaactat ggcgacaaga 1140
accacattag gaaggtgggt aacgatataa atgagccttt gaggggcagg atccaaggat 1200
taagtgctac ccacatgggc actctgattc cattgcctac cactagtaca ctggggaggag 1260
gtgaagtatg gggttcatcg aatgtggtgg gagagcgcta gggattgcat agttgaataa 1320
gggaaggatt tttttttcatg atacttagca ttagggctat aaggactaag atttcattct 1380
taggttcgat gatgaaggaa gctttgcggg ttgacatgtg gttggtaaga cgatgacaaa 1440
tttatgcttt ttaagactaa gacctaggaa tatgttccat caagggaatc ttacatctag 1500
actaggttac aagtcatcct ccatttggat atgattagtc ctaaaattgg ttgttagttt 1560
gttttttagtt gtttatccat acctcatgtg catgaacatg tatttggatg acaagtttat 1620
gtccctagga acacgaatga tcaaacacta gcaaccaaca atgatgtgtc aattttagat 1680
gtggagaagg atgatgaggg cctaaatgaa catgcaaagt accctagttc agagctagag 1740
tgtgatacaa gttgaaagct ttggtaatat gcatgctata ttccttgttc ctttatatgc 1800
aaagataata aagataataa acttcaggag tatttatttt tcatagagaa tgtataagcc 1860
tagttcacca acatgcattt catgtatata aaaatattac atgttcaaat aagtaacttg 1920
tttatattac aattatttga aaaggatatt atgtttttca tgagctttag ttgtccaagt 1980
actcaatcac acactcatac aaattggcag tgataactaa tatatt         2026
```

SEQ ID NO: 5        moltype = DNA   length = 2819
FEATURE             Location/Qualifiers
source              1..2819
                    mol_type = genomic DNA
                    organism = Zea mays
SEQUENCE: 5

```
cctctacatc tcccctccaa ttcccaaaga gtcaaagaca acggacgcag ctagctgtag 60
ctctctccct cctccggcgc aggtggcgcg ccgtacgtgg aaagatcggg ccgcttcgac 120
acgggcgcgc ggagcaagcg gactgaaggg cggtcacttg gcagcaaagc cagcaactac 180
cacgccacca ttacgacgac gacgaccggc ctggaggacg agatcctgcc tgcgacgtcg 240
tcgcgaggtt gttgacgaag ggcgtgcgcg tgcgcgagct gtacgtgtat atatgcaacc 300
acagcaagga tcgtaccgga agcgttggac gtcggtcgca gcgtggccgt gggttaccgg 360
ccaaagcgta tgtgacgcag gcacgcagcg aacgaaagcg gccggccggc cagattcaac 420
gccgcgcgtg ctcgcccggc cggccgtctg gtccaccggg taaccacact gccgcgctgc 480
ctgctcgtgg agatgcattg ctcacagtag taactctgtc gcctctgatc gagaggtgag 540
gccgtgatgc atgctcggac ttcttctctg gtcagtgag gctcgcatta gtggtggcct 600
acttggctcg ctctcagcca gcacagcagt gacagagcaa cggatcaacc gtctctgcac 660
gccgcacgcg ctactagaag accagtcgac cacaggaccc ggccgtctca tttcacgca 720
tcagtaaatc acttccagat gcacgtcgcc ctccgggcgc cttcgcacac cgtagcccac 780
ggctttctgt cgatcgggcc gggcgggtcc ctcggctcct ttgttctttc ccggcagcg 840
gcgaccgcgc cacgcgacgc gacgcgccg tgcgcgccgc gcggcgccac acgatcgaat 900
ccagtcggcc gggcacgcac gcacgatcat cacgtgctcc tttaatttcc cggagccgca 960
ctacgccccct gcctccatca gtccatctgc tccctgcggt gaggtcagcc atgcatgcag 1020
ctagcgtagc taggtgccgt tggatcggcc gcgaccgtac gtagcactat atagcagcag 1080
gcgacggatc agaaccccct ctgtgttcgg atctgtgtcg gaccagggag ggagggagag 1140
agagatagca gtgcaggccg cgccaagcgc cggcgccga gtgccacga ggatatctgg 1200
atcgggcgat caatgatccg gtgccgtggc catcgaccag agcatcacac gacgcgttcg 1260
gcgcgggga ggcttgtcag caggcagttc gaccgcgcga gagccccgga cggacgcccg 1320
gcgatacgga cggagggaat cccatggcgg cgtacggcc gcggcgcggc gcaagggatc 1380
gatgcacggg attggaccgc agactgacag cgagatcgcg gcggacggcg ggcctgccgg 1440
ccgacatgca ccggccaggg tagtacgtac gcgtactact agagacgtaa cggacgatct 1500
```

-continued

```
tgcatgcatg cacatgcaat tatgcatgca cggccctaaa aacagacact cccgatacta 1560
tgtatacatg ctgcatgcgg ccaagcaacg acggtggcgt atgcatcgag ggcgtacgtc 1620
ccccggccca gccgctgg gtccagggtc caggcgggg cagcgtgcac gtcgcggtcg 1680
cgaccatgat gccttgcctt gcctgccctc tgcatgcagc agatggtgta catgtcggcg 1740
acgggccac ggaaaaagca gcagaaaaag cgcacgcggc gaatgaagaa gggaaaagga 1800
aacgcaggtg cgagagggag cggatgcatg gatcgaccga gccggccggg cgtgagatgc 1860
aatgagtata acgatgaagt gatgaacaca acacaccccc acccggccgc agtgatggac 1920
gacctgtacg acgcaattca gctgttcggt gcggcgtcgc cttcgggccg attcgccgga 1980
cggacacagc gcgctgcatg tacccaccca aatctagcta acgaccctcc gatccctcta 2040
gcatgcagat gcagtgcaaa gtaataagac aaaccccggg tcggtgagac gatgccacag 2100
ctagctacta gttccaatca atcagctggg agagggccgg ttctggcccg gcctcccgtg 2160
ctttgctagc tttagttttg gcatcaacga atcgtcgcca acagtcaccg acgacgacga 2220
ggaaggagga ggaggaggag aagattagaa gggtgtcatg gtatggtcca caaaggcatt 2280
atattgatgc ccatgcgtgc atgtaaactg taaagtcttc ttaaatctta acggtgtggg 2340
caatgaaagc tagctagcta gcctgctatc tactggagca gcaggccgt gtggacggtg 2400
ggccacggac ccgacggacc aggcgcggtg caatattgcc caacgccggg cgccatggac 2460
cgacctacca acgtcgctag ctagctagct agctgctacc tatccatggg cggggtttgg 2520
cccggccgga cagggaacac gatgagatgc atgtgtgtgt gctacgcgga aacgaagaga 2580
tcgaattaag cgagatctct gtatggtgcg tgcccttggt tccgcggccc tgccgttgtt 2640
catgtacgtc atgttcacga ggatctgca tcaggcctcc tttgctagct gtccttggtt 2700
caatggttct ggattcgtgt ggccggtctg taattcactg cactggcgag attattattg 2760
ctactggata caggcaatat gtcgagcagg ccatccagtc tgggttcatt cttggtccc 2819

SEQ ID NO: 6           moltype = DNA   length = 2116
FEATURE                Location/Qualifiers
source                 1..2116
                       mol_type = genomic DNA
                       organism = Zea mays
SEQUENCE: 6
acacgaccca caaaggaaag gaatctaccc ccaggcaaag aaggcttacg gtacgggcct 60
gttagaccaa aaccctgca gcccacttgc aaaatagcac cgaagcaccg gcccatctaa 120
cgaaaccctg aggcccatc caacgaaagt agatgatgca agttcgggta cgattcggcc 180
ggcgctcctc cccttgttgg gcctgtgtct cccatcgcat cattcattca ccacatgcgg 240
cattttgatt tcagcgcagc attatttta tacatacgtt gggggaaaaa aagtgccaaa 300
ggccgaagca gtgaaacttg aaagaaatga agagacagaa cagttggtca gtcggcaga 360
gtggcacggc acagtgttgc ggaatgaaat gaagtcggag atcctatatg ggcgggcggc 420
ggcgaggtgc ccggtcgtcg tcggccgcgc gagcagtgtc acatggcatg tttgtgttgt 480
gccgggggcac atcagcaggc gaatcaatca atcaatcaat caatcagtgc gtgctctcga 540
tgacgatga tcggcccgga cctctcacgc aatgcgaggt ccgtcctga tcacatgcgg 600
tcctagctac acagggccct gccgggttca atccacctct agctgggact gggacgggag 660
ggattaggat taggattggg attaggacta gcaacctag ctaactgtgg taggatcgca 720
gcaactaacc ctccttcact agcgctggtc ggtgtcgttc ctgcgaagaa acgaaaccga 780
cgacagctag ctactgatga tcagagtact accacaaggg aataataatg tcgattcata 840
tatatagtac gacgcgtcgg caatctaatc atcgacgccg accggccggt ttagcacgag 900
gtatagtata tagcctctgg cttttgtctct cacacgctgc tgaggtcacg ccacatggca 960
tggagatata tatataggga acatagcaaa acagtaggca tgcatatgcc aagcgcatta 1020
tatttcgcta ccaagtgtag ttaacttgac gtgatgatc catggccgt ttagctgtta 1080
cctctctctt attatattgt acgtactccg ccatattgtt catggccgcc ggccaccagg 1140
agaatgttgt gatcatcatg catactagag cgatgataca tctgccgcta gctccttatt 1200
tctttcttca tcgacaactt ttttgttgga accgaacgcg tgttggagtt ggaccacgca 1260
gcacagcagg ggacgtttat acttgttggt aagctgttgt tagcgctaat gatgacaaac 1320
agacgagggg aagttttcgc ctgaaaaacaa gctaaaacct aggagctagc tacaggtgaa 1380
tcgaactaga gtaggtaact taacttgagc cagtcagtca tgcgcgctgg gctgtgcaat 1440
gcatatgcac cgctgacaat tgtaggccca gctgacagaa aatatataga cacatttatg 1500
tgcgagtcac gtcgctagct ctggatcttg agtcgctttg aaggaggcaa ctgatcgatg 1560
tctgactctg atgctaacca taccctttgca gtgagtgtga gtacaacgta acctactaga 1620
atcacgcatc aaattaacac tcgtcgtcgt tgcctctgta ccgagtaatt gttgctgctg 1680
gcgggcttcc agtttttttc atttttcttt tcagatggcg gagctcacgt ccgcttccca 1740
ggtccacgca cagctcacgt ccggctcccc aatcaaccga aagctgccgc tgaagctgaga 1800
ctgagacgga gggctgacc ggtggggcg tgcgtgatgc cctcctcctc ctcggaaaag 1860
gtgagtgggt gggtggccga gggccgaggg ccgtgcacag gctgacacag gccagttgct 1920
tttctgagct ctgcctgtct cttctgccca gatatgggac aatcctgcct ggtctcaatc 1980
ggggttgaga acatctcttt gtcgtcacca cggttactta cacttacctc ccgtggtaat 2040
taaccaggca aaagcaatta actgaaccca acgacgtgta cgtaccgtag acagacatg 2100
tcgggagccc ggacac 2116

SEQ ID NO: 7           moltype = DNA   length = 1634
FEATURE                Location/Qualifiers
source                 1..1634
                       mol_type = genomic DNA
                       organism = Zea mays
SEQUENCE: 7
gacaaagtac acaatcaacc cctttgcaaa attgtgagcc attcatgcat aaaagaggaa 60
atattgctct catatctggt atctatcttt tccctccaat tacagttaaa aaggaaaaag 120
gaaacgaaac gaagaggaaa gtaatattga ctgttacaga tcttattctc cccaatgcaa 180
gtggaactac tttgtttttt cgggtcttcg tccatgcttt ttttcccctc caaccatctg 240
attgttagat actgtcattt cgccattcaa tcggaatcaa tcttcaagtt gccggagcaa 300
acggcccatt ggaatcgaac gagaaccttc gggagagag aggagctggg gaaaatgttc 360
tagctagcta gggttttgtg tgggcggacg gtgactcgcg cttgcatgca ttgcacactc 420
```

-continued

```
tccggccggc cccgaccctc tccgtggagc cctagctaga tcaagctatc gcactccggc    480
cgtcccgtga aaaagaaaaa acggtgtttg gagaacacgc agcacgtacg catcgagagt    540
cccaacacag tgacaggacc acaccccag atcatgtctc aactctcaag tagatggcca     600
caggcatgtg atgagtctgt tgcagttgaa cgatcatgtc gtagtcgtcg accgcaccgg    660
ttttaatttc ctgatgacga gctagctagc tctctgtttt cagaatcaat tatttagaca    720
tgcgtgtgct cgatctacat atatagctag ctggccgaaa aggatgaagg ttttcagcc     780
atgcatatat atgcatcagt gcctgtcgtc tccttcgcca tgcatgcatg cacaccaatg    840
aaacgcgaac aatcatttag gacgacgacg acgaggagga ggactgcatg ctgctagctg    900
cctgcctccc tgccccgaaa acgggtgcat gcctgcatgc atttgcaccc acacccactg    960
cgcaggccgc agggtcgggc acaaggtcac cagcgccgga gatggtccaa gcatgcacag   1020
cacggctatg tatcgagctg catgcatgcc agcagctgtt ggttggccac cgggatttgg   1080
tctcctcccg cgtggccatg gcatgtggtg gtctgatgtg aacagctgct gctgctggct   1140
tgttcgtagc ctattccggc tgcatccact acggaccgac gatacgcggt ccatccggcc   1200
agctacatgc agagacgaca gatcatacta gctagctagc taggggcgcc gtcgagacca   1260
taccggcctg tgtcgtgtgg cctgtgtggg gaagctgaag gatgcttcgc agccacatgc   1320
cgccattgct tggccgcgat aagcaagcca tccattcgcg gccctgtgtg ttctgcgtgt   1380
agctctcagc tccgccgcac aagcggagaa aaacaaaaga tgtggccacg atttttgggg   1440
atcattttcg tggccaggca gcctccgct gatgtggata ggtatccaag caagtgaaca    1500
aagtagtggt gggcactgca ccaggaccag ggggaaggaa aggaagaagg atgcatgctt   1560
ctattcaatc tttcacccat ttgccaatgc gcacgtataa ctcgcccccg cgttgcctag   1620
ctccctcgac gacg                                                     1634

SEQ ID NO: 8         moltype = DNA   length = 4840
FEATURE              Location/Qualifiers
source               1..4840
                     mol_type = genomic DNA
                     organism = Zea mays
SEQUENCE: 8
cggttgtact tgtaaatcta gctgcttgta cgatagttat atgatgtgtt tttttatcca     60
tagcgaccac cacgacaatc tagacctagc tagtgcgact gattttaca tcaatacatc    120
gcaaaagcta cgcacttaga gagaaaaata aacattggaa tttagagggt acagtattta    180
gcacttcgtt acagatgtgt gaaaatccgg agccgatttt gcaatagccg tggatcgctg    240
aaatcagacc ttccttgtgc tgtctaaaat aaataaatgt tttgtgttct tcgtcggaac    300
aagaacaagc accggttgct cggaccgtgg agaaaactgg ttgggctgtg ccgagaaaca    360
atgagcgggc tgggctgcgt cttgacggcg ggcaccaaa ctgtcccgcc gtgcgcggca    420
ggcaacaacc acaacgtcat gtgcggcttg cttaactggg cccgttagac gcgggcttcg    480
tgtggccttg gaacacggcc gttcgacctg gcttcacgtg acgtgaacca gagcggagcg    540
gggccatcga tttcggccgc gcgaaacgcg tgcgcgaggc ctgcgaaagg ccgctggatg    600
aagctcccct tgattgaagc ccgtgtgggc cgcaccgcat ggtccggccg gcgatcctga    660
ccgttggagt acgatttatt cgatgcgtat gtactcagct cgatccatat acgatatgat    720
agtacgtaga catcttagac gtaagttgtt taaggaactc tctctctctc tctctctctc    780
tctcgggttt ctgtgttcat ctcaaagttt tttcagttca aaaaccaatt cgaaaacaaa    840
tcggcttaaa attcaggtaa tcaggtcaag cgacttact ctggtctgaa taacttgaga    900
catccgggtt gccatggccg actctagaca gcggccataa acacggtggt ttctttttct    960
tattgggata gtaggtcact ccaaataaag gctattgcca tatgctaagg agacggaatt   1020
tgtgacgcca tcgccaccgg gttaacgtta atattctact actagagaat ctagcttacg   1080
tttcggttcc ggccggccag tagaaaactc tctctgaacc gaccggtcag aatcccctgc   1140
tcggtgctcg gttgcttgga ccgcacgcac gcaccctat atcgtcagtg cctgtaacag   1200
ttcttattcg gtgattatta ttataatatt atttccacgtt tgcacacacc gcacatccgc   1260
ccgtttgtaa aactgtgagt tgatcgtcga gacgaaaggt ggagctggag tatatggctg   1320
ggcttcgatt gccgctcgca ggtcggtgtc ggtcccgaac tttttactc gcgctccatc   1380
accacatagc ctggcgatcc tatcgtctgc ctacggggcc gcagcggcgc tcctccatct   1440
cctgggtctc gttgtagcca catatagagt agtagattgt tcgtcctcgc aatgatccgt   1500
agtgcacaat gcccagtcga atagtcgatg aatagcacat acacatatat gcgtgtgtgt   1560
ggtcttgtca aggttaactg ctgcagagat gagatgccaa agaaaaaaca catattctaa   1620
ttaataaagc tttgtgtgcc gcgacaagct agctaggcta ctgtctcgta cgttcacgcg   1680
gtctaaatca cgggcgcagc acaaattcga tggcagcctg gactaaacga ggccgtggcc   1740
gtcgtcacca ttcaccgatc cacaggattc acccggggc aaaaccagcg cacattacct    1800
ttgcaggaca ggagttagag gcgccttttt cctggtccct ctctctgctg agcacatga    1860
gcagctagct agctcacgct actagtcact cgcgaagaac gaatcccggg ccggcgccac   1920
tagttgtggc tagctctcgc gtctttacat tcgcagctgc agcgtccatt tcacaggcag   1980
tatacatgca tgtgatcgag tggaaggagg agaggccacc gctggccgct gcccgctgct   2040
tttcacgtac aggcgccggc agtgcaattt ggcgacgatg cgaggtgttc gccagtatgt   2100
ctcgctgaaa gggtgaagcc ggagaaaggg ggaagaatgt ttgctgcggc gggagaat    2160
aagatcgcat ctcgatggga attagaacgg ccgccggccg agtgtgtgtg tgtggactgt   2220
ggatcgaaca ttccgccgcg cgcctgaaag gactgtcgaa gcattgtgac atctgtcagt   2280
cgatcgatcg tgtggttaac ttaacggatg ctaaccctag cttctttttt ctcttcagtc   2340
tagctagctt tctatctttg gagacaggga cagcattttt ctttttgtt ttttagtggt   2400
acctttaatt ttgctggtgt cggttgtact tgtaaatcta gctgcttgta cgatagttat   2460
atgatgtgtt tttttatcca tagcgaccac cacgacaatc tagacctagc tagtgcgact   2520
gattttaca tcaatacatc gcaaaagcta cgcacttaga gagaaaaata aacattggaa    2580
tttagagggt acagtattta gcacttcgtt acagatgtgt gaaaatccgg agccgatttt   2640
gcaatagccg tggatcgctg aaatcagacc ttccttgtgc tgtctaaaat aaataaatgt   2700
tttgtgttct tcgtcggaac aagaacaagc accggttgct cggaccgtgg agaaaactgg   2760
ttgggctgtg ccgagaaaca atgagcgggc tgggctgcgt cttgacggcg ggcaccaaa    2820
ctgtcccgcc gtgcgcggca ggcaacaacc acaacgtcat gtgcggcttg cttaactggg   2880
cccgttagac gcgggcttcg tgtggccttg gaacacggcc gttcgacctg gcttcacgtg   2940
acgtgaacca gagcggagcg gggccatcga tttcggccgc gcgaaacgcg tgcgcgaggc   3000
ctgcgaaagg ccgctggatg aagctcccct tgattgaagc ccgtgtgggc cgcaccgcat   3060
```

-continued

```
ggtccggccg gcgatcgtga ccgttggagt acgatttatt cgatgcgtat gtactcagct  3120
cgatccatat acgatatgat agtacgtaga catcttagac gtaagttgtt taaggaactc  3180
tctctctctc tctctctctc tctcgggttt ctgtgttcat ctcaaagttt tttcagttca  3240
aaaaccaatt cgaaaacaaa tcggcttaaa attcaggtaa tcaggtcaag cgactttact  3300
ctggtctgaa taacttgaga catccgggtt gccatgggca actctagaca gcggccataa  3360
acacggtggt ttcttttttct tattgggata gtaggtcact ccaaataaag gctattgcca  3420
tatgctaagg agacggaatt tgtgacgcca tcgccaccgg gttaacgtta atattctact  3480
actagagaat ctagcttacg tttcggttcc ggccggccag tagaaaactc tctctgaacc  3540
gaccggtcag aatcccctgc tcggtgctcg gttgcttgga ccgcacgcac gcaccccatg  3600
atcgtcagtg cctgtaacag ttcttattcg gtgattatta ttataatatt attccacgtt  3660
tgcacacacc gcacatccgc ccgtttgtaa aactgtgagt tgatcgtcga gacgaaaggt  3720
ggagctggag tatatggctg ggcttcgatt gccgctcgca ggtcggtgtc ggtcccgaac  3780
tttttactc gcgctccatc accacatagc ctggcgatcc tatcgtctgc ctacggggcc  3840
gcagcggcgc tcctccatct cctgggtctc gttgtagcca catatagagt agtagattgt  3900
tcgtcctcgc aatgatccgt agtgcacaat gcccagtcga atagtcgatg aatagcacat  3960
acacatatat gcgtgtgtgt ggtcttgtca aggttaactg ctgcagagat gagatgccaa  4020
agaaaaaaca catattctaa ttaataaagc tttgtgtgcc gcgacaagct agctaggcta  4080
ctgtctcgta cgttcacgcg gtctaaatca cgggcgcagc acaaattcga tggcagcctg  4140
gactaaacga ggccgtgggcc gtcgtcacca ttcaccgatc cacaggattc acccgggggc  4200
aaaaccagcg cacattacct ttgcaggaca ggagttagag gcgccttttt cctggtccct  4260
ctctctgctg agcacatgca gcagctagct agctcacgct actagtcact cgcgaagaac  4320
gaatcccggg ccggcgccac tagttgtggc tagctctcgc gtctttacat tcgcagctga  4380
agcgtccatt tcacaggcag tatacatgca tgtgatcgag tggaaggagg agaggccacc  4440
gctgccgct gcccgctgct tttcacgtac aggcgccggc agtgcaattt ggcgacgatg  4500
cgaggtgttc gccagtatgt ctcgctgaaa gggtgaagcc ggagaaaggg ggaagaatgt  4560
ttgctgcggc ggatggagat aagatcgcat ctcgatggga attagaacgg ccgccgcgcg  4620
agtgtgtgtg tgtggactgt ggatcgaaca ttccgccgcg cgcctgaaag gactgtcgaa  4680
gcattgtgac atctgtcagt cgatcgatcg tgtggttaac ttaacggatg ctaaccctag  4740
cttcttttttt ctcttcagtc tagctagctt tctatcttgg gagacaggga cagcattttt  4800
cttttgttt tttagtggt accttttaatt ttgctggtgt                         4840

SEQ ID NO: 9          moltype = DNA  length = 1726
FEATURE               Location/Qualifiers
source                1..1726
                      mol_type = genomic DNA
                      organism = Zea mays
SEQUENCE: 9
gcggctagtg gatcgatcac acatgtttcg aactatcttc tttttccctgt atgaggtaca    60
gtagtagctt acggacgaag ggatagatag atatatacat accatgtgct atgcgcgtct   120
cacttgtgta cctacagcta cagatgtgca tctctatcct atctcttcac tctggccacc   180
ttttcttcta gctcggaagg aaaaaaaaag catgtattat tgcatcactt ttttttttgca   240
agggatacgt tgcagcagta ctactactgc gacgcgaatt tcattcacg ccgcgtacgc    300
gataggcacc gctgcatgca cccaccggca cagtactaac ggtttagatg tctactactt   360
attaattcaa tcacgcgtct gcgagaaagc aagccgacgg gcatcttctg cccgagtctc    420
tccgcgtttc tgtaactaga attgtcatag tcagggttgc caaacatcag catcccgagg   480
cagtttcttt aattctgctt tttttttatat atgtaagttt gcttaccgaa tgagctagtt   540
ctaaacaaac tcaaaaacaa aacaggcaa ctgggggtcc cttgacattg cacagatgga    600
cctgaccact ttgagattcc cccggcttct atctccttttt ccctcccctt ggatcaaatg    660
aacaaaggag cgcattctct ctctctctct ctctctaaaa gattaaaaaa aagcctgcat    720
gtagtgttct ttgacaagga caaggaagcc ctttatacatc aatacatcat tcgtatgttg    780
ttgttttctg tgttctttgc gttccttttt ttccccctccc tccgccttttt ttctacttga    840
ttgttgccaa gatctggagc acctgctctg atctgattgt gtgcgctggt ttactgaacc    900
ttccggaggg ctatacgctt cgtacgggga cataccaatt tcaaagaatt cagtcatcag    960
gtaggtggtt caatcatacc gatggttccc tcactgcatc actcaccttc tcatttttac   1020
gcatcataat tttttgttcc cttctcctta attcccatgc ggtgaaggag agatgtgaac  1080
taacagtttg gcgctgcact gttcgaccgg ctaaacacgg ggccaatgct ctctgtacgt  1140
gcagatggat aggatagtct ttgattcttg tttcaagatg acgtggatag tctataaatag  1200
ctaaatgttt gcctcgacta ctaacttgcc gatatgggcg agggtaactt taaattaaat  1260
ttttaaagca tttgacttgt taaaaaaaat aaaagcctat attctttgtt gatggaggga  1320
gcaagtggct gaaaagccgt tgccatttct gggcgctccc taaactacgc ggcaagcagg  1380
ctattgggag cccttgtcgc tgtcgacgcg atgtgcggcc tctttcttcg tcctcttggt  1440
taggtcttat ctacatggtc acgcatccag tttattcatt aggtacgcta actgtgtgat  1500
cgtatgttca gtttaattta tatgtgttag agtataaaaa aattatgta aattttacat  1560
tagcttgagt cagtcagtca gagcaaatta atttagcggc tagaccgcta gaggctagtc  1620
gcgtgcgtgc gtcgctgata ctcaccgtca gtccgtcacc gacacttggc ctgggcggcg  1680
tgtagcagca gcacggatac gggcaatacg gccgggtgca tggtct                 1726

SEQ ID NO: 10         moltype = DNA  length = 1923
FEATURE               Location/Qualifiers
source                1..1923
                      mol_type = genomic DNA
                      organism = Zea mays
SEQUENCE: 10
cggggccata ggaggttact aggtttcatg gccacgggag ctatggttcc gccatcacag     60
gccccaagac aagtattcca gatcaaaaca tataaaatatg ttttgatttg acggcagcca   120
aaagtactgc gacgacgtac gtacgtacac taaaccgatg taaaaccgta ctacgcgctc   180
atgttcggcg gccggatcca cgcagaagtt tgacagcgga attaacagag gcagagctcc   240
ggatgatcag tctcacttac ctcccagttc tcaacagcct cgtctgtagc caagtcagaa   300
tatatatgag tgtgtgccac tgccgacaca tgcatatgag ctattgagct cgacagggga   360
```

-continued

```
aattaaagag agagaaaatg ctacagtagt ggaaactgct cctgatgaga ccggccggcc 420
ggaccagatc gaccttgcaa gagcggagag gacggccggc cggtcgcagc tagcgctgga 480
tctcggggagg acaacgggca ctgtggcgtg cacatgcatg tgcgatcgaa agaagcttgc 540
gatggtgtaa atagtgaggt cccagctgtt cacagtgcat taatttgtgc ggccggcgag 600
cgacgacgag cggtggcggt gcagagaacc gacgacgagc ggaacagttt ggtcagccaa 660
ctctttggac ctgcatgcta tgctaatgta atgaatcgaa ctgatgagtg cgcggccggca 720
cctgtgcaga cgagtactac tactctacag tggttcatgg tcaccgtgct gctgtgtgcc 780
tgtgcaccgc gaccgacgac gacgccgcga ttcgctcgtg cacgcgagag ccagtcagcc 840
actgccgccc ttgcgcatga tgcggtcggt gaacctagct agctagtcg tcggcgcctg 900
ccctatgcat gcggatgcag gacaccaca catgtgacag cggcatccgg cagcgctgct 960
ccatccacaa cctgcagctg ccgatctggc atcattacca agagagagag agagctgggg 1020
atggattatg gatatgccaa agcttctagc gcaacgaacc gacacagaca cagtgctctc 1080
gtacggttgg tgagacggct ggctggcatg gcatggcatg gcacacccca tgcatgtgga 1140
cagtggactg ggggagaagg agaggaggtt accgatggag gtcggttttg cagaatcatc 1200
ctctactaat atagtaacta gggatccgca cccgcgccct ctattacctg aggcacgacg 1260
ctgcgtggat ccgatcatgt gggccgcagc cagctctggc atttggatcg cagcacgatc 1320
tttaccgagc aaaaacaaaa ttattacagc cgcgactgcg atgtactact agtactcaac 1380
ggcaccacgg ccgttctcgc tcactcgtcg cccacgccga cgccaccacc gtgtagcata 1440
gcaatcagtg acgagctgac aattgggggc gtgctgtcac gtgggccact tctctccgat 1500
tctctaccac tcttttgttt ccgcatggtc taagtggacc ccatcgcctg gcgattcttt 1560
ttttccttct ttactttata ataattccct cgtcccgtgg tcgcgaggat agacagacgg 1620
atggaggaag acgcgacgg gagatgcaga tgcgtcacgc ggtgctgtg ccgtgcgggtg 1680
cctttcgggg aatttgtgcc gcgccaaagg ggagcctcgt ggggcccga ggcctgccgc 1740
ggacccaccg gggctcacca aaagctggct ggatattgct tggcaaaaag gacaccaaaa 1800
gaaaacggga aagggttggc cgtaaataat tggcacacgc agcatatgca cacagcttct 1860
tcaaaagaac aatataagta ggcgttagag atccatacga ctatacctat tgctgtccat 1920
att                                                                1923

SEQ ID NO: 11           moltype = DNA   length = 1660
FEATURE                 Location/Qualifiers
source                  1..1660
                        mol_type = genomic DNA
                        organism = Zea mays
SEQUENCE: 11
ttagaatttg ctatgcaata aatatttaaa aaggtgcata taagagagaa aaacatggat 60
atagtgacga gattactctt gttaggtgtt ccttgaacat ctaccctagt caaagtaaaa 120
tcccttacca cccttcttat gggatcacac aaatgatggg aatttatacc caaaaattcc 180
atgaaatatg caatagaata aaagaacgtg gcacaaattt gacatgtttg agatataaag 240
ttatcatcaa tctatagtag ccaaaacaag gacaaacaaa aaagtttaag gaattaatta 300
ggactcaaac atataggaat tgaaacacag acatgacaat agcaaataga atcaacaat 360
tatgtaagtt tttaacacat aaaaatcaaa caatggttat agacttgtag ttctccaatc 420
tctagttttt cattgattag caatgcaaag gttgtatggg acaaaaactc aacataatcc 480
ataggcatca agtttactat ggtatataag accagcaaga ctaagataat attatggtcg 540
catatcactc attataaaca aggggtacata aaagagtaca ttctaaacgt ttttacaata 600
ttgcatgcat ttgcttattg cactagtagg gacaaaaaag acttctagtc agagaggagc 660
caacaacaat gccctttgag gtggttaaaa cctagggggt gaagaaggggc ttcttttggcc 720
atcaatgaag cattataaaa tcatggaacc acttgttact caatctctca ctatttgtct 780
attcgatgtg tgatgaagtg ttgatgatac attgtgtgtt ggcacatggg cttgtgttct 840
actcattacg taggccatgt gataggatga gtagtggcta actcgacaag tggtgaccaa 900
gtgaggtagg gttacatagt ttttatatat atgatattat ttgggcatac attataccta 960
tattattggg attattttgg tcagaatttg aaatgcattc tataatgttc gaaggccta 1020
acgggtaacc aagaagggta cataggaaac atgttgattg taatgtattc gatatccttc 1080
taaaatttgg ccataaagcc ctttataggg agtgaaaaca acacatcaat gtctcgtaac 1140
ggagaaatcc ctattattta aagggattgg gccccattt ccatgcctac ggaatgctta 1200
tattcaagt gcactctaga aacgtaactt gcacatggat gacatgatca agactcgtcg 1260
catgtgatac aattaccttt tctactccac attcttattt gactttttgtc tctagtattt 1320
tttgttgtc ctagacaccc catcagtaga gtccaccttcc ttgtcaatga accttaacta 1380
cccaccacca aaaaatccct cttttctactt tcattatatt ggtataattg ctatagctat 1440
cttgttagtt gcaaaaagac tagtcccatt gccttactag tgaccctaat ggagggctac 1500
atatccttgg tagatgtgga ggtaccaatg gttccatcac atccattaga ttaggaggac 1560
accatgatag gcactagtct caacattaac catagttctt gttttttctt ttaaaatcga 1620
aagcattatt ttgttttaaa ttcttttagt cgaaataaac                         1660

SEQ ID NO: 12           moltype = DNA   length = 1552
FEATURE                 Location/Qualifiers
source                  1..1552
                        mol_type = genomic DNA
                        organism = Zea mays
SEQUENCE: 12
atatatatat aggacagcgg aagtagtgcc gtacgtgtgc aaaaagactc cctacgctag 60
ctagctagct agctagctat atatatgcgt gcattttgta gggatcggag agcttgtcat 120
tgcgtggtat atgttcgttc acgcagtggc cctggccgtg tatatatagc tagagctagt 180
gacctttcag tgtttcatct agtcacccct atcgtctatc ctcattggag cctagcgcgc 240
gcgggcgcgg tgacaggagg ccgatccggc ggtcgacgag gggcgagagg gacgagatcg 300
gatccaaagac acacaaaaaa aaggtaggca gcgaccgacc ctagctatgt atcctacgac 360
gtgcgtgcat gcaatggtga tccatcctgc agtacgcttg cgtcgcagtgt gtcgcctcgc 420
ctgatctata gccaccacac gcacacacac atcgatctct acgaccgagc tgacgctgtc 480
gtcgtcgctt actaccactt gacttactac actgccgtag gaaaggcctg cgccgtacgt 540
acatgctcac gctgccctgc tggtgcctgg tggtggtggt ggtgtggtgt gtgtcgatcg 600
```

```
tgtgtgcatg catgctggca tgctgccgtc ccagcgcccg gccggtcacg cgcgccaaca    660
gccaacgcta agtatgtagt ggccgtggtc gatgctgtgg taaacaagcc atgcactacc    720
accaccagct agcgtcatgt atctcatata tatctcaact gagcatgatg cgtgtataca    780
gtatataagc aggctagctg cacctgcact cggaagaaca actgcatgtg cgtacgtact    840
agcagatga atagctagca gctagctaga accgtgtgac gtgttgtgat ttgaccgatg     900
gcaaattaaa aggtgctcta atccgttatc tgtccatatg tatatgtgga atccgacgac    960
acacacggcg atcgagagtg atccatgagt ggccgacgtg tattacacac atcttatata   1020
ttagcttatt aactgtgtcg tcttgtgatg tcagctacta ggtgccgccg tgccgcagta   1080
tgtagctagc tcgtcaccaa ccctcacccc ggccccctata tatatctttg aattatatat   1140
gtatgtatgt atagtatgtt ttctcaagct caaaatatat atagttgatg ttatacgatt   1200
caaatattgt ctcaaagcag ttattacttt ggctcaaata ttttttctcta cctctctttt   1260
tctcgttgtt ttacgttgca catgtttttt agaataaaag aagtatatat agctttacaa   1320
gtaagtatgt ttaaccaaaa gaagaaaaag ctaagcgcat atgcgtcgt tgaccgcaat    1380
aaccagcacg gaaaattcta acaaaccgcc cgacaggtcg aggacgtcag gtcacatcga   1440
cgatctgctg gttggaagaa acatatggac atggagcccg tacgggccgg ggggagaaat   1500
cagatacgcc acgcagacgc accaccattc atgcgtttgt atatgctagc ta           1552

SEQ ID NO: 13            moltype = DNA   length = 1636
FEATURE                  Location/Qualifiers
source                   1..1636
                         mol_type = genomic DNA
                         organism = Zea mays
SEQUENCE: 13
gcggtagtag tagccggtgt ttggttgcta gccacacact tttgtgtaaa gtaagtcgat     60
caagttggtg agtacttggt tggttggata ttaaacttgg gtaatagtct ttatagctcg    120
ctagctagct ccaagtatat catagagtaa aaagcgtaga aaaattgagt gattcatccc    180
ttgagcttgc attgcttgct caattgacta ctcaccagag ctctcaggca tctctctagg    240
gatgatgttg cgcatcccct ccgtaaatga cggcgccccc tcccgagcag gcctgccttc    300
agtggcggct accttcttgt tggaggtctc gtctctctct ctcgagcggt atgcagtatg    360
ctccccgtcg actctgctgt ctgctcgcag tccattcgtc caggcagaac cctaccgcta    420
tactagaagt aggtagtagc cccgcctccg acatggaccg gaagaccgc tcccatgcac     480
tcctcaccgt gtcccgtacc tagaagacgg gatggaggag aaagacgtga aggagagacg    540
agtgtgtaac acttttttt tggggggtgg gcacattaat gtgtgtacat gagcgaccga     600
gaccagtact acaagtctct cgttcgtctt ctctccatcg atcgaaacat gccgcaccgt    660
cttcagtagt tctctctgct ggcgaaaggg catgcatgca tgtgcggaaa ctatactaga    720
acattaacaa actaacaaat ataatccggtg gtctgtgtat aatctaaccg tagctatata    780
gcaagcagtg tgggtgtggg cagctgctgg tgtgcggcgt gagaaatata ggagggggac    840
ggatcggacc agaacacaac agtcgaagaa cacggggaac agtgcgcgcg gtgggtggcg    900
cggcaacagt agtgctagtg ccggccccgg tccccatccg atgatgaccga ccgctactac    960
taccagcttg cattgcgtcg acgacgcatt gcttgggccg cgcgcgcgtg tatgtgtgtc   1020
cctgtcacct gtcgccacca gatcggctcg ccggccgccc gctaccgaga tgaaagtaca   1080
gtacgttgga cgagcgcgca cgctggcttt gcccacgacc acgagcagtg cagtgtgcaa   1140
acctatctat ccaagcacag tatgctact acatatacga tctactctag tagctagggc   1200
gactgtagcc ccaatgtacg tacaatatac gtacgtacgt gcacgctgct tcgtgtcaaa   1260
aaaaaggcca ctgtacctac ctcacgaagt actataagga cctgtcatgt ccttatatga   1320
gacatcatag taccgtacca aagtatgtac acgcggtgca ccggatcgtc tcaggtctct   1380
atcaagcgaa ggccgagatt ggtgtggata ccaaatcgaa aacatgcagt acatttgtcg    1440
tcagcaggct atgcccagca gcacactcat cctacgcatc gatctgcgtc taactattca   1500
ccttccagcc ccaccgtgga tgacattgtg caaaatgagc gctcgacgta cgtaccccat   1560
ttctttggct ttctctctgt ctcctacgac tgtgtatgcg tatctgctga gatagagcgg   1620
tcactttcct cgggct                                                    1636

SEQ ID NO: 14            moltype = DNA   length = 1584
FEATURE                  Location/Qualifiers
source                   1..1584
                         mol_type = genomic DNA
                         organism = Zea mays
SEQUENCE: 14
ggtactgatt acctaggaaa ataatcttgt tgagggtcta gctggtaacc tggttgataa     60
gggggtggct attctactct attctgatga caaatttgtg aattaaagat gacttataca    120
ttgctagaaa catgaatctt gttgtatatt taaataatgc tatttggacc aaagattaac    180
ttcactaata ttgaggaccc gatgattaat gataataatg aaaatttaaa cacatgctga    240
tgtttaattg tcaagtgagt atgttcccca caaagtatct tggggtcccc aacagactct    300
acatcattga ctggctacac gtctatgaga aatctaccaa aaaattagat gcattggcat    360
gctagttccc taacaatggt ggaagaggtg ttttgattaa atccaatttg aataatcctg    420
ttatatatca aatgtctata tttatcttac tccaaaccat cattgataag attgataaat    480
agagaagatc attgctttag taatgaggga ggtttactag cttataatag aaaatgttat    540
ctattcaaat ggactaagta gggaaaagtg ccaagaaagg aggtttaaga attataaatt    600
tcaagcaaat agatattttc ttagtaaata attggtggta taaattagta aatatgtagg    660
ggcattaaac aggaaagtac tcatcctaag tatattagaa ctttgtgaat ttggaaaatc    720
aagcatatac atgatgattc tcgaaatatgg acagatttac taattttaaa ttaggcatgg    780
aaaattcaag tcaataatgg aaagggacca tattttagct tgatgcttag caaggaaaat    840
ttcccctcca tcgtcaacac cctgttctat ttgtactttg taatgaaaaa accagtgttt    900
aggtttaaac atgtaaatgg tactcaagga aaaaggtagt agacatccaa ggtggctccc    960
atccccttgc tatgtgattt ttttgagtta ataacttata tgcatgcaag gattgcaatc   1020
atatatttca ttctccatat tagttgcata tttctagtca tagcaattgt gaaggtttct   1080
taatgtactt tgactatgtg ctcatgtaaa tttactccct acttcattca cccttgggca   1140
ctgatgtacc ctaaacttga tatgatggtc caaacttctc tttgggagaa atggaatgaa   1200
gttcaatatc attccctata gagcattgcc ttcgccatgc ttaggccatg gatcctcctc   1260
```

```
tagtggccct ctaggatgaa attcatgttc aataataggt cttactatgg tctataattg    1320
atggcatagt cgccttcgac tccaagctcc actatgtgcc aacatcaccc ttcctcacaca   1380
agcagatgtt catcatctat gatgatatac attagggcat acaatgcatg ctttacaggc    1440
ttcgctaaga cttccacatg cctaaccttc ataatgtggt ccatgagttt atttgcaatt    1500
gctccatgtt aaatcaatac aataccaaac acattcgcgt acatggggat cttaatgtca    1560
ttgcgtattt cgatggtggt ttga                                           1584
```

SEQ ID NO: 15          moltype = DNA  length = 1776
FEATURE                Location/Qualifiers
source                 1..1776
                       mol_type = genomic DNA
                       organism = Zea mays
SEQUENCE: 15
```
tgcggctgat ggtgtaaggt gctaaacagt aaacactgta gctgcaacgc tgctagaaca    60
ggcagtggag cttggatcac cttgctgtca ttttggttac gacttaagcg attgtctatt   120
ttgtcaacat gctttaatct tatatgctct tttccttgga aatttgcagc ttgtatctga   180
cattcatgta gccccagttg gcactgttct cgctcagggc atgaactcaa agaagaagca   240
cgaagtaggt aattcggctt catactgatt gttgaacttc ctatgtcctc tttttttcc    300
tgcaaatatg ttgttatttg aactctcatg tttgaagaaa ttgctttatt cagattgaaa   360
atctagctgc tgtggttcat gcaattgcaa agaggtgtgg agccaagaca gtggttgatg   420
taggttctgg ccaggtatgt catatgcatg ctagcatctg tgcaattgta accagattcc   480
tagtagtcat aattttcttt ctaatacttg gacagttgat ccctctttt attccttttg    540
gttgtgatta tgccatctta aatgttaggt ttatgcattc atcaccaatc ccgagcaaga   600
atgccccaat cgatccagct aaatatactg ccccgagga aaagcaatat actgtgcttt    660
atacatgtcc atatttcata aactatgcct ttatcgcatg atactcttga agtctggatg   720
ctaagagtcc aaattatgga ctgttttact catcttcaa tagtcagaac ctacaaagaa    780
catgttctac atggtctggt tcgttatttt gttgacttaa ttgcaagctg caaacaaatg   840
aacaagtcaa gctatctggt ttttgttgta gacattgcat ggcaatgcct tattttttat   900
gttgctgtta aatgaaagaa atgattgaat ttaacctagt atcagcagta acgtgttgtg   960
tcatgcattt atcttatttc ccatcttatt tgattactag ggttatctcg cacaggcctt  1020
atcttttgag taccaactcc gtgttgtagc aatagatgct tcatcacacc atgcatcagt  1080
tacaattgct cgtgcagaaa gaataaagaa gcactatgct gctaaatggt gcaaccttca  1140
tcaagtttaa tttgagttct actacctttg gattccatc taatggtata aattgtgcct   1200
attattttg ttagtgtgga gaagcaactg ctcatggcat ctagggcagt cacctgtcat   1260
gttcttctca gtgacacatt ggcagcagtc acattagatg catgtaagga tgacaatgga  1320
gaacatgtga gagatactaa aacatctact aagaaaatca ctcaaatcca ggaatcaact  1380
cagggcaccc ctccattaat cctgctggt cttcatgcat gtggtgatct ttcagttaac   1440
atgctaaggt tggtatttgc gaagttgaga acatggccat ggagcatggt cctttctcca  1500
agctccgctaa atgttgcata ttgaaatata gtattttcca ccttggtgaa agtccttcaa  1560
atattacatt ctttttttaca gagttttttgt gtcctgtgaa caagtaaaag cattggtaag  1620
cattggctgc tgttacaact tgctttctga ggatacttat gaggacacag atacctgccc   1680
tggttttcct atgagcaagg ctgccaaaca ttctgaattg gtacttggga aaagcatccg   1740
tgaccttgca tgtcaggtat gatagcagtt catgat                             1776
```

SEQ ID NO: 16          moltype = DNA  length = 2025
FEATURE                Location/Qualifiers
source                 1..2025
                       mol_type = genomic DNA
                       organism = Zea mays
SEQUENCE: 16
```
ccatggcatt gtcatcacga tttgattaac ttattcctac tctactaaga caaaatctct    60
tgaaattctt taatcctacc cctcaatgct cacctgcagt gaccccacct cccacgcccg   120
tggtcatttc cacacgtgac tccctcccct tacctctcga cctccaccct tgttctccct   180
tcacagactc cattgtcgcc accggccttc accacctaga agtggcaatg caaagtgcgg   240
cctcacctac ggttgtcgag gttcgggtga atgagcacct tccacaacgt agatggtgca   300
aggaaggcgt gttgttgggc atgcaagcgg tggtggcatg tggcctctca acgctacgac   360
acaggaggtg agaacgtcgg aatcaccggc ctcaaccctt aaaggcatgt gtctaagatg   420
aagcacatgg atgagcttag catggcccac taggctagct atgttgtgtc ggtccgatac   480
gtaacggatt gtgcctagt gggctaggc ccgtgctagg cttggcgccg tttggtcatc    540
catatatagt cacaaccaaa ggaacatacg aaagatacct atttttttt cttttgtttt   600
ataatcacta aatgtgtaac aaagatagag gtggcattat gtgaacttgt gagatgaaaa   660
ctactgccac tttctactag catggaaatg catccaaatg ctctccatgc atgtgagatg   720
ccaaattggc aatgcagttg aacctatcat tgttagaatt agattctcct tgagtgagga   780
taggggaa aaagggcgtc ctaatcgctt gtgattccga tgaatatata aagtcgctcg    840
gtcgtcatgc aaagtgcgca aggaatgctc tttaaggtac attactctac cctccttat    900
ctttttttt cctatcagct gaatgtcctc tggatcggca agaatgttcg tcttcgatgc    960
tagactagaa ggctggctgg atcgccctgc aatcttctc tctcgaggat tgcatgatcc   1020
gagcttctct ggcgctcctt tttataattc gacacgaatt tggcttgcaa tcatttctgc  1080
gttattcttg ctttcggtta ttttttttgt ttctcctcat ctgatacttt gcatatccac  1140
atcactttat tctgcggttt gctttattct tataggctaa aatctcattt cagtggcctt   1200
ttggtgccat ccttttttggt cccttgctga ttcgttcttt agtgtcttgg aattgtagct  1260
gatcgatgct ggtatcctga tgaccaagaa tatatatatg acactgataa atgattggga  1320
aaaaaaggg gtccatggag gaggtcagta tgataaaaaa aatagtgctc agaagaatat   1380
atatgtta gaagaaaagt tgccatcgtt cccaaagttc attaatttt ttgttaccgt    1440
caataatctc attattaaga gtaagaagta tattattggc tgtatgaaag ttatactgct  1500
agattttgtt tttgcctaga aatgcttaaa cagaagtaac ttttttttca ccaaattaca  1560
tctgcaacga catcgttaaa aaatgagaag aattaagaat agaaagatgt ttgaaaatca  1620
ctccaggtca cctcggacaa aaaacctgcg cctttggatg catagacggc tctggtcccg  1680
ctggaccacc tgatcaggag gtgtgccccg cttgagagag atcagagatg cggcaaagag  1740
```

```
tgcatgcatg cacgcaccat ttgactctct ctccccTctc tctctcttTt cattgtaatt    1800
ccaatactac tatggagtac tatttattat tatgtgtcta tgttactgcc tgactgaatt    1860
ttcacactgt agcagttcca agattggagc ctcaaaagat gagcttcttc ctccaacatt    1920
atcgccaacg ccaatcatgt gtgcgtccta catatgtcga gtgttttgcc cagcgcgacc    1980
aggatttctg tagccatgca gggattgacc tagggaagaa agtga                    2025

SEQ ID NO: 17           moltype = DNA   length = 2103
FEATURE                 Location/Qualifiers
source                  1..2103
                        mol_type = genomic DNA
                        organism = Zea mays
SEQUENCE: 17
agaatgagag tacactcatc atgcatgcgc tttcatacgt aacagtacat tggatgctca      60
aacgctctac acgtgtgggc cggtgcaccg ggtacgtact cggtgcagtg cacatatata     120
tacgtgtgtg tcggggccag ggccgggccc ggggccttgg ttgctgtctg tagtagttca     180
tgtaggtgtg tgtgttcttg tgtggggctg gcatgcaaat ggtttggtgc ccgacggtcg     240
aggcgatcca tgtccatatg gccatgatat acagtacagt atggctgtaa agccgaagac     300
aaaagcctcg catcgggcag aggacgacaa agagctggcc tgtacctgta ctgtacgtac     360
ttgctggccg gccgggccga aaccacgtcc atccaccatc tccattcccc ccgtcgctcc     420
tgcggcctgc cgcctgcctg ccacgctgcc aggtccagct gccagcgcca gcggccagct     480
caccaccttc ttgcccctca cttttcagtt ttcaccattc accggcggac tcccttggcc     540
ctcgggctgc ctgcctgtct agtgtctact acaggagtga ctagcagtgc gagaggccga     600
gagcagtgct cgtgctctga gcaccacgta cacgtacagt agtggcacgt gccaatgcca     660
gctgccatcg atcttgagcc gtgtgttttc cagcaaggat tccggcaggc tccaggcgag     720
accagagtac cagaccacca catgcgatgc aagccggctt gggagtgcgc gcccgcgtag     780
acacggaagg ggggaacggg gatcccagtt cgaggttcct gtctccccgg ccccgcaagc     840
ccaacaaatg gccgaataca taccatgcgc cacgtggagc ggtggtgcgg cacagctgga     900
tccctggcga cgaacgaag acgagaccgt ccgtcttgac cgcctactgt actgtacttg     960
ggctgcgtgc gagcttgcag gctgcacgca gctgccgcct gctgcctgt ctttcttct      1020
gtactctgca gctctgcctc aaccgctcga ccgaacgcca cagtgacact ggcagcaggt    1080
acgcgccagg acgaacggac ccaacacagt gtgccagtgt ggtctggccg tacgtttgtt    1140
tgttactgtt gcgatcccga tcgtccacgg caacgacgac acgccgacga ctttcggcca    1200
tccatccgat ccgaccctg cctctgcgag ctgtaattaa actcctcggc ggtagtacgg      1260
tgcaccgccc gccgcccga ccccaattcc cgcacgcggc cgacggttc cgggcagggc      1320
agaacaggag ccgccgcatg caccatccat cctagccgta gcccgccgct ctcggctccc    1380
cctcccaacg acctgccgct gttcctcctc tggctgcctg gtgcctgccc gcagcgcca     1440
ggagacgaga ccacgctcct ccaccacccc ttccacgtgc tccctccttt ccttgccttt    1500
cctctcctct cctctgcgtg gactggacac tgggctgccc tgccaactc cctcctggac     1560
gtaccttaaa accctaccct ttccccctgc tgctcgtgtt gaccactacc gctgttccc     1620
agcaggtcac tccctcagac cctcactcag acactcatct ttctttgcct gatccggccg    1680
ttacctcttg ctacttcctt tccctttttt tcggccccaa tgcgaacgaa cggctcccat    1740
tcccttcttc tttttgtaga cagacagaca gagagagaga gagttttcgc gccgttgcgt    1800
gacggctgac ggggtgtgag gcgccgattg ttctttcgcg cggtaggatt acacgcgtca    1860
atcaatcatc cgcgtgtgca atactatact gctactacca gtaataaaca ggcaggaaaa    1920
gccaacgcac ctgcctgcct ggctgctgg ctgctgctca aatttctgcc ggcgccgctt     1980
cggcgtggat gaggatgagg aggagggagg aaggactact ggagtaggta gtgggaagct    2040
gacgtggcgg ggtggtgcag cgccggaagc ggcatctcga ggggcgcgtc ttcgatcgct    2100
agt                                                                  2103

SEQ ID NO: 18           moltype = DNA   length = 1535
FEATURE                 Location/Qualifiers
source                  1..1535
                        mol_type = genomic DNA
                        organism = Zea mays
SEQUENCE: 18
gtgggtgtgg gtgctttgac tcgcggtcct cgtcgtggtg cccggtctac tactaggctt      60
gggccaccac gccagtgctg gattctctgc ctcgcccact ccttttttgc ctgcgatttt     120
cacagctgac agctctagac actagtgcta gtttagggtt tcatttgttc gtgtcccgct     180
cgcctcctac tgtcaaccaa cctctttttgc tcttcgccta gctagtcgtc ctcctgtgag    240
gtcaacttcg gggaatttc cacggtcgcg tcgcgctctc gcccttTctg ttcgcttgct     300
gcacaacttc ggggtacttc ttggctggcc agttaataca cttTcacccca ttagaggcca    360
ttaccagaga taagtattcc ttgcttggcg ccttctccgt cggagatgcc ttaagactag     420
gctgctggga ctctttcggc tgttcaggaa accgtgggag agatcgctct tgcacttgcg     480
ccccaggcgt agaatgtgtt catagcgagc tcccatgatg gatcctcctc cccatcccag     540
ctaagctact agttcgttcg ttgcttcctt cttcctcaca gcagatcgag gaaggagacg     600
gacaagaaca acctaatctg gcctagccgt ggatatgatg cagcgtgcaa cgaaatggtc     660
aaacgggaca ctagcgcacg gcggggaaac gagacaacgt agcacggcaa gctagcagcg     720
cgacgacaaa gccatcgccg tcggcgttcc cgtacgttcc cgtgctgcaa attgcccacc     780
gtagcggccg gaggtgtgcg agttatccaa gcacaagcag cgtggtcaag gaggctgcct     840
acttggctcg agtggagtgg aagtcttgca cgggccagcc aggtcaccgg agactggcta     900
cacgccgcct gcccgctgag ctcgacggac ggcgcctcaa ttgcctcttg cacttggcact    960
cccgctctag gtgcgaaac ccatgacagc ggatgctaat actacgccgc ggaagacggc     1020
aggtggccat aggagagcgc cgcagacacc aggacagccg gcgaggcgca gcgggcacag    1080
cccagcaact accccgcaag gctcgtcgga cgctgcatct gcatcgccaa gaaagtaaac    1140
ataaatgtga taactatatt ttttTtaata tttatatata tattTttttat tTgtttatg     1200
taaatTaaaa aacgaaaaca taatatagta tgggcccagc ccaccgtgcc tattTccccT    1260
tcatggacat acttTcatgg acataggagc gtggattcgg tccacgggat cttggattTg    1320
gtccgaaagg tcaccgtata aaaaaataac ttttTaccgt acttaacttt tgtatattga    1380
tttaattgat aattgaatat attatatatg taccTattat ttaatacatt gcatgtattg    1440
```

```
aatattgctc ctagtgtttg cttatatgca tggagcgact ctaggcgaga aagttctcca   1500
gaataataca ttgacgtcaa gatcaaggat ttgtg                              1535

SEQ ID NO: 19           moltype = DNA   length = 1943
FEATURE                 Location/Qualifiers
source                  1..1943
                        mol_type = genomic DNA
                        organism = Zea mays
SEQUENCE: 19
agagaggaca gctgggttgt actcgatctc gatgactcct gctccccgta tgcgagcacg    60
tcaacgctag atgtaccgcc gtcgtcgcgc ggggcagctg tcgccccgcc cgaatcaccg   120
tcacagccgc cacgcaaggt aatcctcctt tccagcatcc ctatgtctcc gtctccatcc   180
ctctgtcgtc tgatccgatt caccatccaa ttttgactgc tttcgtttca gttgtgtatc   240
ggtatataca gacgctggta tcaaggcaac acacagcaat tattactacc gccatcaata   300
taggcgttct cagctcgcca cggccagctt tgtactcctt ccttggtttt tggcgcacaa   360
agaccctaga ttactctagg tagaagagac ataaataaaa agctactgct agtactgcta   420
cagtactagg agtatgtaat accataggat caacggcccc ctctgcagct taagatccta   480
aaagtaaaaa gtatagtaac tgcgcgccta tactgtgcga aaacttatcc tctcactgca   540
cgccaattaa cgcggagttt tacctcacca ttactacttg ggtttggggg aagaaaaagg   600
cgctgaaaag gcaccacatg cgcaaccaga agggaaggct acgtatgctg ctgctgcgta   660
ctccgtgtgc atggactccg atccctccca gattttaagc gaggtgctag ctacaagtgc   720
agattgattg gcgctgacca tgcacgacgg tttcaaaatt ctccagaccg agcagttttt   780
ttgcaagcgt tttcgaaatt ggctagctca gctgataaat atagatacta taatgatgga   840
ttggttagct tagctaggac tataggagcc cggaggcagc gagatgttat tattggtccc   900
tcgaccgaac aggacaggat ccacgacgac agatcaggtc agggtcaaca cacgagagaa   960
attaaaaagc agtgtgagtg gaacaatcat gcatgcagcg atgcctagct ttggcgtggc  1020
ctcatctgct gctgctgctg ctagattcag atgcatcccg ctcccattat cctgtccagg  1080
ccaggggtgc cgtgacagtg acaggaagag gttgttgctt tgctttgctt tccttttcct  1140
ctcgtttaac ttcccctttt gcccggacca acggcacta taggctagct agcgcccacc  1200
tgaccccgcc gctgcataat ttgcacaccc ccgcgctccg gcccctttcat cagccctctt  1260
ttttccccct ctcttatgca cgctaggttc cgaaatttta tctatttatt tatctattta  1320
tatataattt gttttatcca cagaaaaatc ggtagcacat catcaacagc gttctggggg  1380
gtggtcggcg cacgtgacgc ccccgtccg gctgggatga caccacacca cacgccatcg  1440
ctatgcatgc tgttgctgcg gccgcgtgag cgtgacacac cgtgcagcgg tcgttttctc  1500
ttttcggccg tccctccctc ttcttttcgg ccgcccctcc ctctgtgtgt gcgcgcactg  1560
tgcagcatgc accagtcacc agcagccgcc gctgtttttt tttttgcctg agaaagtgcg  1620
tggctgccgc gcccggccca tggccgggga aatgtccttt cctcttcgg cctccgtccg   1680
gcggcgcacg tcctcgtggt gacgtgacgt ggtgcgtcat ccatgcacgg cacgtacggg  1740
gggagggggg ggtgcttgag cgcgtgttcg gtgtcccccgc cgccggcaga cggacgagat  1800
ggttgtggtg cgtgcggcgc cgtcgatcgg gacctggatg gctagctctc tgcctctctc  1860
gtgctttgtg cagaggcatg cttttacgcc ggcgagcggc ggtgctgcaa cagtgcaagt  1920
agctagtagg taggtcggtg ata                                         1943

SEQ ID NO: 20           moltype = DNA   length = 1569
FEATURE                 Location/Qualifiers
source                  1..1569
                        mol_type = other DNA
                        organism = Zea mays
SEQUENCE: 20
gaggacgttg ctggagactg acttagtagc gagtccggcc actacacgca cgcacgatgg    60
ggtgtgccgg ctattgcgaa ccgatgcacg cagctatcgt ctcttcggct gttcggcacc   120
atgtgagagc tgagctatcc ctgagcagct gcagtgcaca cggcacctgc gagcgttttc   180
tcgaccctgt gttctgtgat caggtcgcaa atgcgttgtg ggcagaaaga aggcacaggc   240
acggccggta cgccgagcctc cggtcggcgg tggtagcgcg aagaaggcgc atggagcgta   300
cgggtgacgg cgtggggggca gcgaggccga gattgccgtg tgagcgaatc tgaagcagta   360
caccgtgatc cgtaaacgat ggcccacttc acttttgttgt gtgcatgaac gcacgccgac   420
acggccacgt gccacggcgc ggtggttcga tcgttcactg gtttggtact tcggttcggt   480
ccggttcgct tccggccgcc taacctgcca cctgccaggc agcgggcagc gggcagctcg   540
gacgacaggg ctcgtgagcg cacacgctgg ccatctatct atcttctcca gcaactcctg   600
atctggaggc atgagcgcgg ccggctctgt tcggccggcc gtgcgctgga aaaggggtct   660
gcagatcggc tacataccct aacagcaaac cgatgtgatg tacctgtagc atgtcattgg   720
cagcctgcat gcgcgccatc gatccccatg cattgacatt gtgattgtga tgttgattgt   780
tgagactagt cagtgacatc gctttcaaga tgtaatttcg aaacctattt tgctgtgatc   840
tggtcaccag ccggaggaat aaaaaagggg ttttataggg cgtgcgcctg tggtctggct   900
ggtcacagga aactcagcga ctcttttctgg ctgggtctctc actgactacc ataccaagca   960
ctagaactac tctgtctgtg ctgaacaatt cttttttctca cctcctcaac ggtcaacaca  1020
cagtacaggc tgagacttgt tcattcttcg ccggcctgga agctactact acgtactata  1080
aaacaaagca cgtacgcatt gggcgatcgg cggcgtcgga aatgtgctga gtagtagtat  1140
tcaggagcta gcgttgaatc cgccgtcact ctcgccacca aatgcgctga acagttccga  1200
ttccgctttg aagctctcaa acttcacacg tcgccatcgc cgccatcact gcgcccggtc  1260
acaatcccta gaagcttcct gcacaacggg gcagcctccc tctgcctcct gccgatccct  1320
gcgttcatcc aaagatctca gctagctagc cctacattcc cctccgctgc acattgttgg  1380
gcgtgcagcc ctgcctgcaa accgagaaat tgctcctgt ggctcatg cccacatgca    1440
caaccacgtg gccatgacct gaagccccca acaccccacc ccacctagag atctaacgct  1500
gctgccgata tctcatgcct agaccttttt ctatgggatt tggtctttgg ccttctagcc  1560
atattctca                                                         1569

SEQ ID NO: 21           moltype = DNA   length = 1750
FEATURE                 Location/Qualifiers
```

```
source                  1..1750
                        mol_type = genomic DNA
                        organism = Zea mays
SEQUENCE: 21
gctggacttc agcgccatag gtattttcgt caagctcgtt accaaggttt atgacattga    60
ggtcagcgcc ataggtcatg gtgttaccat atcgttacgt cacttctacg ctaacatctt   120
gtcgatggtg tcaaactatg taacctcgac gctatagaac atgaaataga cctagagtct   180
cgaatcgatt gtagttttgt ctcaagtcta aacatgtgtt gttgccctct tgttttgtat   240
tttgttcttt tttttgttac gagagaagag atttaaaaaa aaacacaaga attgacgtat   300
ctgtaacgag cagagtacac acgtgggcta gctctccgct gaaaagaata cgatttacat   360
acgtgtaaag gttgtgccca ctcggcagaa atttggtgat gcggggccag gtcgttagcc   420
tcggatgcag cctgcaggca gcctgtggtg tggtgtggtc caaaaagggc gggaacagaa   480
acgagggggct ggacgcctgg acccatggat caggtggtgg tggtccgtgt gggcgcaagc   540
accagtacag tacagtacag tacttccccc cccgctcctg catgcatcgt cctctgtaaa   600
cacaaggctt tacccgaaag cacaagctca cctaattaag ctcatgtacg cttctggcgc   660
gcacaataga cacgccgta cgcaggagca catggcacca accgaatgat ttgagcaacc   720
gtctccgcat ctggaatcca ttccactcac ccaaacagag ctccagctcc cctctctatcc   780
agcagactgg acgggacggg acggagcgta gactagcaga acagaagcca ggcaggtcgt   840
ccggtcgggg tcctttccct cttctctcc gttttctccg ctggggaaaa agaaaatcgg   900
aaaatgacgc tccacggaag aagcgcgcga gccgatggca atggttcccg tcagcgtcga   960
gcggcgatgg tccccgagac ttttttccccc cctcctcccc tgcgtgccgc acacggccgg  1020
aacggttcctt gctgttgcgg cttttctatct tggaacagcg ccggccggtt gaatccgccg  1080
tgttcctagt gcaagttgca gagcggagca aagcaaggga ccttgccgca aaaaccgtgg  1140
cggggtgtcg tctaactttg tccgtcaagg gtcgccgtcg gccttgacaa aacgacagc   1200
tgctgaccgt gacgagttag aagagagaga gagagggaga tagaagaaaa atcacccacc  1260
tccggaccctc cccacacgaa acgaaaagct acgacctacc tctcttccag acgtaacgta  1320
agcatgaaac agaaagcact gcctgccgga aaaacaaaaa caaaaacaaa aaaaacccga  1380
aagactaata aataattcac cgctcctctt tcgcatttct ccggatcttg tatgcatgat  1440
gtgtgtgtgt gtgcctgtgg ataattggac gcactccacc ctacagtctc ctctctcagc  1500
ttcgttcctg cgccccgta tcgtatccta atcctaatgc atgctcacgt ctgggtcccg  1560
tgggccacca ggttttaat gtgcccttct gtagccacac gcggagggga aaaggaaccc  1620
gcaagaaatg agagtggaac agaaggcgtc tattttgca cgatggtata ggaagcctgc  1680
tggcgggctc gacggtgcct cgatcagagc gtacaaaatg aagcgtgtga agctgttgga  1740
gttgacctac                                                         1750

SEQ ID NO: 22          moltype = DNA   length = 1942
FEATURE                Location/Qualifiers
source                 1..1942
                       mol_type = genomic DNA
                       organism = Zea mays
SEQUENCE: 22
gctcgtaaac ctcttcgttc ttttccatgt tggcggcatt ccctttgtcg tcctttgaac    60
tagaccctta tgaaaaataa gtcgcttctg ttatagtaga tgggtatcta gatagatcag   120
aacagggatg cccacttttg ctttcacatt tttttgtcca ccacaataat aagcaacatt   180
gtgcctaaaa atatgttctc cgaggcaaaa agaagtttta gcctagctag ccatgggttg   240
catgagctct gacaaggcct tttatggcct agtcactttg gttcgcacga aaacaaaagg   300
ataatcttct atagttttta aatccaatta atcaaaaaaa tcagccgatg caaaacttgt   360
agctatattg caatttgcaa agctaataat tagtgtaaaa actacgtacc ttgtgaggct   420
tacctgtgca taggggtgggc tataggaaga agatgcgtca ttatctaaaa ttaagcctta   480
atttggatgg agggaaaggt atttgtgaa tgtattgtta acggtgtagt actccaatcc   540
atgctactta aataatatac aaacggacag gataataaga tatcaatcat atatactacca   600
aattaatgat tggcatgaaa caagttaatc aaactaatgt ctgctagaca agataaaatg   660
ttatcaaatg caaacacgtg tgcgattgtc gtcctcacgc gcatatcgtc ggcctttcagt   720
gttttttct ttctttacat aaaatattaa aaaagatca gaggggaatt cagggagaaa    780
tggccgggaa caagactagc cagaggaata atattgacgtc acaaatcaca cacagaatgc   840
acatcgatgc ataatatatg cgtccgcctg tcggtctcat cgtcagagtc aatcatcacc   900
tactgacgaa ttaatggaca aaaatcacat cttgctatgc acaaaccggg acttgctacc   960
aactctatct tctctctacg cataaacaac atgtaaccca caaattaaat gacgatataa  1020
tcgcccagtt catgcatgag ctaatattgt ttttgggggg tacatggaaa atcccagtac  1080
gtgtatcttt ttcggtccag ctgattattg ctgatgaggg gccggggcca tcggatcaac  1140
agtcgcgtct ctgaaacctt cactgggatg tctgatgtct ctctcccccc tctcattctc  1200
atgagtaaac agttcaactg catacatgga cgcgagacct tcttctttttc tcgcagaaga  1260
ttgctccttt ccttgacgca gagattaaat aaagcctgaa agcgatgcgg tttagatgga  1320
gttaattaga gctagaacat gagtttttga aagtgtttgt ggtagtaggcc ggccagcagc  1380
agggggtagaa tggataggcg cacgcaacgc aaccgacaag cggcacacgc tggtactgca  1440
gcctgaaagc tggctgacaa tggtggatcg agctactagg tagttagcta gggcctgcag  1500
ctgcaactag gccggtgccg gtgcttgctc gttggacatt atatataatc ctgcaaactg  1560
cgatgtgccg tattgaaata actagaaaac aatcgctgct gtttgcgaag gttgttatag  1620
attggatgaa caaaagtgta tatatatcgt ttcttttttaa tttgtcatat ttgtagcacg  1680
ttcgaagctt tagttataaa aaactaaat ggtaaaatct tgaagtatgt attatattaa   1740
taaggcataa cacaaaggaa atgcatcctt catttattgg cgcaatgata ttgcactggt  1800
agattaatcg ttctaaatgg aagacccaa acacacatag ctagcagcgt gaccttgaag  1860
ggaaaggagt acgaaaaaaa atgttgtcaa gatgacagga atggtagctg gctagtggag  1920
cttctcggtc tcggaattca tc                                           1942

SEQ ID NO: 23          moltype = DNA   length = 1574
FEATURE                Location/Qualifiers
source                 1..1574
                       mol_type = genomic DNA
```

```
                    organism = Zea mays
SEQUENCE: 23
ttcgtaataa taatgcaata ctgatggaga cgtcgacgac tggacacaga ttcatatata    60
ataatgcaat actaatgggg cgccctcagt ttcagtcttt gcgctggaaa tggccgatca   120
ttaaaaaaat ttcttttgtc gaaattcata gacttgcgaa acgatcttga aatatactta   180
cttcaccatg ttcctgcacc caaaaaaaaa agttctccca ttcccatcct cttccaggaa   240
caaaagcaca gctaccctac ccaggtgagg gctgagggat gtgtagtagt actgtccatc   300
cctgcatggc ggaatgggcg ccggagtcgg cggcgcttcg agaatcatgc gtggcaggca   360
gcgagaactc caatgcaagg cagcttgctg ccatcgattg ccatgactga aacacgcatg   420
catgcatgca tgcagagttc tagtgtctgc aatggacaat gatgaatcct cctctcccct   480
gcattgcaat tgcaaagcag catgcaatgc aatgctctag atcttccggc gactgggcgc   540
cggcgaccac gcccgcccgc ccaccaccaa ccatacgcat gaattttaag ctgcccctca   600
tcaaccagtc atgagtcatc attgccatgc acccccccc cgccgcgtcg tccgccgtgc    660
ctgccatgcc atcgccggac cagacacaat gattcgccca tgatcatcgc cggaccggct   720
agtcgatgtg gatcgaagca acgtacgtac tgtacgctgt gctgcagtgg caccaccact   780
gtatgtatcc actgcaccgc ttgttgcgcc cacaccaagc acttggtagt ttgcatgccc   840
cgcagaggtg tgcaggccgg ccatgcctgc aggctggctg cagccggctg catgcatcgg   900
ccaagcttgg ctgcagagct agcgatgcat actgggctac tggcgtcgca ggcggcgggtg   960
atgcgtagtc cggcagtggt cgcggtcgca gccggccagc aggaagcgcc actgggggttt  1020
tggagagacg tgcatggcgc tttctccggg cgctagctag cttagctcga gattgactgg  1080
caggctgcat gggcaggcag tgcgcctggc cgcgcctgac gacggctgtg cctcggctag  1140
ctcttgctgc cagtgccagt gccaggcaag ctgacgcccg gtttcctcca ccaccggcca  1200
ccgccatcca ggatcaggtt cagaagagga gagaaaaagt gtgcatgatg gagaaaatact 1260
gtgagcttca gtttgcccga tgtcacagca gcgcgcgcgg tgggcgaggg aacaggagga  1320
catgtatgtg ctcagctcca tgacccgccc tccaactgt ttacggtctt cgtggccctc   1380
taacggttac agtgtgagga tagcgcgcgc tccgtcaggc caagtcaacc ggatgagtgg  1440
acgcagcaaa acagtgttgc atgtcacaca agaatataaa aaaaaatttc ccttcgcgga  1500
ccccttttta ttcaccggtg gtgccagtaa ctctttcctc cctatgctta cgtatcaatg  1560
tgcagatagc taga                                                    1574

SEQ ID NO: 24           moltype = DNA  length = 1601
FEATURE                 Location/Qualifiers
source                  1..1601
                        mol_type = genomic DNA
                        organism = Zea mays
SEQUENCE: 24
taactaatat gcctcactaa tcattatata cataaacaac tgattatttg cctcccagcc    60
aatgatataa gaagtgacaa aaaacatgta aaatcaccac caggaagaaa aaaaaacttt   120
ttcaatgttc cagtatataa catatatact gacaaaagac cgtatgagaa tttggcccaa   180
tagtccctcc aatttgacgt gatcaatcta aaccactttgc tagtttcact cgataaagaa   240
gttacccaat ttcaatgcc acatataaca tatatggtac agcacccaaa ttatttgaat    300
ttggacataa ggaaacgtta catgcacctc aagaactaac tgatcagttt ctggcctgaa   360
aacaccagat tacccagcaa gtattggaac agtcctgtca cagttttagg ggagttgcca   420
atagctacca ataaatgaaa ttgactgtcc aagcattatc tgaataacag gctcagctgt   480
tgaatttctg acaaggtgaa aacaataatc ttactcagta tatgtcttgt tgaacagctc   540
gcacgaacca acaataccag gccctccaac tttcgggtac tgaaatagta gaatgaagat   600
gatgtggaaa atgcagtcaa aagtcttgta aattataaat ttttagtagt ctggaaaatc   660
ttgcgtccat cttttgaata ataatgtgaa gaccagagcc atgatgtgca agattacaag   720
atttgatatc tgaactttga agtgacatat atcaatata cactaccaaa tcaagttcat    780
ttgcatctca acctcatcgc acagttcgaa aaacctaagc aggtatatat aacatggcat   840
tctatagtgt atggctttat gaactacttt cttatttttgc aacctacttc ctgatgtagt  900
ttaagataat attggtaaaa aaatgaacaa tgtacaaatt aatccactga tccattatca   960
agcaaaaaaa tgttgcaaat gatggaactt gcctgtgata ctagtgaaag aaattttgtag 1020
gtatccaatg catatctcac caaagcctca ttctccctg gatttatagt acacctgcaa   1080
tgcagaaaag aaagacacga gcactaataa acattattca ctaagctctg ctttataata  1140
catcggcaat gcagaagaga aaggattgag cactaacaaa ctattcactg agttttgttg  1200
tttgtccttt gaattggtaa tcacacttac cactatacca gttcgtattg tatgatatgc  1260
agatactaga taggataaca ttgtaaatta accacatgta cataaactag gattacaaat  1320
caagttcttc aatcgaatag caatcaagga tagtcctgca atatatgaat tagttgattt  1380
cttgactaat gttaaatttc ttgactacat agttatgact ggtatttatg cagcaactac  1440
aatgaatttc tgatgataaa tcactagctc caatgttgta cctggtcctg tcctttatgt  1500
tcaatctctg gagcctggat aggacaaatt aggtggcttt aggagctcct aggcacgtcc   1560
agtaagtgtt tataggcacg tgagttgtat tttctggtag g                      1601

SEQ ID NO: 25           moltype = DNA  length = 2872
FEATURE                 Location/Qualifiers
source                  1..2872
                        mol_type = genomic DNA
                        organism = Zea mays
SEQUENCE: 25
tttaccgcag catcacgccc acgccggcct ccatgctctc gatcgattat tatatttccc    60
accgcgcgcg cgcgtccaga tgctgccaga atcccatcat tcatttccat gcccggccgg   120
ccggcctgcg tgttgaaaag ttgcagctag cacacacgat cgctatcata ttcaggttca   180
gccctgcagt tcgttgcagt taggctctga aacacatgta gatagttaga tagatgcaca   240
cacacacaaa tgcatgcgag gaggatcatg catgatgatg aacagtcgtt gcgcagtaga   300
gtgagtggag cacacgcaat cagacgcgct gatagctcct gtaattgccg ccatcagtga   360
catgatgatg atgctggcgc gttcattaat tccctgcagc tggcagatct ccgatcccat   420
ccgtcgtcgc ttgcagtggc tcagcgagag cctctgatga gcttaagctc ttgttcaata   480
tgcgctcatg catctcactg tattacatca tgcttactcg gtgatgatgc atgacgagac   540
```

```
cgggcaaaat gttgctcgca tcgggaatga tgaggaatag tagtgtatat aatgatgcgc    600
atttagtaca gccttttcga tttgtttagt cttgatgctc acgggatcga tgagaaaggc    660
tgcaggccgg gtgcatcagc tgctaatcat caccttgtct tatattactc cagcgatcga    720
tctaatctaa tccgatatat gtatgcggta tgcctagctt tctagttagt tatgtaaaat    780
gcagctagca aaagacacag gggtatactg atactagtat acaataataa tgccctaaat    840
aatgcagagc acatgtatct aatgcagcag aaaggcaaaa gaaagggtaa agagtataa     900
gtagtgtagt gggtgtgcat gggggccaac cacaacagtc tgaacaaacc tcttgcattc    960
tgcaccatcc atatgcatat gtgcttgctt tcgagctctt ttggaacaat aatctgcagt   1020
ggcccgccta cacagtcact ggaccaccac agtgagaaca agagagagag agagagcttt   1080
ggtggtctgg tctctgaaac ccatgtgatc atcatatccc tgccctggcc actaaataat   1140
ataatttctt gttttccatg aaggatcgt tcacgcgatg tagatcaagc ttacgagcat    1200
gaaaagtggt cagaactcct acttaataag gagttcttgg gatatatatt tgaccctact   1260
tctagtatag taactacata taataaacaa ctcagttgaa aaagtggtca ggtcaactct   1320
gctggctggc tgttgaggtt tcagggtcat acaaacaaga ctggtgaaag ctatctgctt   1380
tacttgtcat ggcgccatat ccccacgatc gaggactttc ttttcttgct tcttcctctt   1440
ccttcagtgc tagctagttc tgtacgtctc tctgccccct gggcctgcgc atcctccatt   1500
ttgccgcgaa ccatatgcag acaacgcgcg tcaaaataac cctagtcgtt tactgctctt   1560
gttggtttcc ttggattcag ctagctgtgc gtgtgccccg gcccccaaat aaggtgagat   1620
ctgtcgtctg aaggcaggca tatgatttgc cttgatttct acacccagca ggccgggggc   1680
cggctccatc gagagctcag ggacacagag ttgacatcag tgtgtatact ttttgtacgt   1740
tacacttgag tgcttcatca gctagctgct agctactcca ctcctagtct cctactacta   1800
tatattgcgg tacatgacca tttgccagct gctgtaatga cacaggtgct atatatattt   1860
ctacaaacca aaatcaaagg aagaagaaaa aaaccagctt gattatcata tgctggatta   1920
aattatccaa tcatcccaca atcatgaaat agttaactag agtaacgtac ggtaaatgct   1980
tattattaat tttggatcat gagtaattaa acttttttct actgtttgta cgtactttaa   2040
cgtagctggc agctaaatcg ggtttaaaag cggtatctg gtctagctca aaagggtcac    2100
ctagctagct ttattttcca tgcatgaaaa atatgaaagc tttgctcgat cttttataat   2160
ttagaaagtt ccgcgcgctg acttgtttgc atggtgtgtg tctttgcata gctctgctgc   2220
cgcattaatt ttgccgcgca ccacgcagag acagtgcgca tcaaaatgca agttctggtg   2280
gcaatgcttt tgttatttac tttgttcaaa caaaagaagg taaaaatgag tcgacgaaat   2340
ggtacgtaat aaatatctgc tcagttgcaa ggcatgattt gccttattgg ttgctttgct   2400
tccacccagc tagcgctgaa cgcttcgaga ggcagggaca catgacaggt ttggtacacg   2460
tactcgagtg cttcatctgg ctagcaccgc tggtgagatg agtaactttt acttaaacct   2520
aggatatatg atcactctta tagtagtatt acatcgtgca tcaggccacc aggttgaacg   2580
atacacagta aaaaatagga gtagaggtca ataaatattt atattccacg aataagatat   2640
cattttttt tttttgctga taaatggtaa aggagaagtt agaacccta agggacataa     2700
taaatattc agatgataat atcgttaaca cacaagagag taatgtccaa gatgaactaa   2760
ttgacaagag ccttatgcta ttaaacttat tcatcccttg tagttaaaca gctttcatta   2820
aagagagaaa tattatcagt ggtaaatggt aatgattttt gcataaaatt tt          2872
```

SEQ ID NO: 26         moltype = DNA   length = 2642
FEATURE              Location/Qualifiers
source               1..2642
                       mol_type = genomic DNA
                       organism = Zea mays
SEQUENCE: 26

```
gtgagtaaag taaacttcat aaatttgaat gcataagcac ctagtacgca aatacatgcg     60
tgaaaaataa gagtaaaatg tcggctccat aatcctgcat tagggataaa catgatatgt    120
tcagggaatt ctaacaaaga ccgatagatc tacacatatt ctcacctgaa ttggtgtacc    180
agtgagacac cagcgccgat ctgcagtcag agcagccgca gctagggata tcaaactttt    240
agaagatttt atcatgtgtg cttcgtcaag cacaactcta aaccaatgta cagagtacaa    300
agccccattt tctgttgaac cctagccaag cagatatcaa aagttcagtc aagaataagt    360
ttgcataatt caaactaaat attaatagca atggacccag cagttcccca tcattgcatc    420
catactttgg tcaatgtggc tatcttgttt atgcatgtat ggaccaaatt taagcaagcc    480
atattttacc aataagattg tgtaagtatg acatgaagga tcaaatgcag aaacatggtg    540
ggaaggacaa aagacaagca aatgggtaat gcattatctg tattattttg ataaaaaatg    600
gacacaagta aaagtagaag atgtcaaatc aagtggctat agtagtaaga gtatgcaaat    660
gaccaatcaa tcgcatggtc tggtgctatc taggttatct taattcttaa ccaatgaatt    720
ttttacaaaa gcttgaacat aataagagta aactgaaaga aataagat ctcagagctt      780
acatcgattg aaaactctga tgacacaaca ccatatgtag tcaggacaat atcactctga    840
ccaatgatgc ttgcatcttt tggcctgttt tgtccatagt gaacatatat attcgcagtg    900
cctggcttag tatgagcttc aatctctgcc tgttattcat aacatcaact ctagtgttca    960
gaaaaatagt tgaagaaac acttaaagat gaaattggta aagcaagtca aaattatgtt   1020
aacctcttat cttttacttt tctgcagcaa ataagcaca atataatgta gcataggcaa   1080
tggtggggtg gtgccacaat tagaactata ccttccactg actaattagt gtcattggac   1140
agataattag attgctcct ccaataagtg gggcctagg tttcttgtgt ttgctaaaag     1200
agaaagggtt agcaagcttc ttcacagcat catgcgattc acccaaccca ctagcttctc   1260
tagggtcgt agcagcattc tgagttgtga tgcatccttt gctagaatca gaagaagaa     1320
gagctatcgt cataatgtc ttccccagtc ccattgcatc tgccagaatc ttaattta      1380
ctccagttaa tagaattgat cgtaaaatca accagaaacg atagctatca tagaaatgct   1440
aaacataaag aaatacaata ttaaaatat tcttactcct cctctagaaa gttgtaatgt    1500
actaggaaat tcagttgtag catcgcctga aaacacgttc aagtacaaaa cgagttccct   1560
cctgaaaataa atgcaataaa atatgaaatg taatgtccaa ctattgccag aatggttat   1620
aaaaaacagct catataacac atgcatactt atcctcagtt ttgtatgctt cccaacaagg   1680
gtgaagggtt gtagcggcat cctgggaaga actacctttc tcaagctgca gcatccaatg   1740
aagtgcctgc ttttgataag agcgtagatc acacatcaga gaatcagggg gagccctttc   1800
ctacaaaata taaattcaga gcacactgag gtcaggataa tatccactag ttgctgaaac   1860
actgcacaac gatgggctgt tgaattacct ctagtgcaca gctgtctgag atcccaatta   1920
tatcatccaa atctgaatct gaaacagttt cttcaccatg atcatcttcg tttccatcag   1980
```

```
aagacaacct caatctgccg gatgtcagct ttgcagcagg agaccctata ctgctctgtt   2040
caggcagaaa aaacataaaa ggccaatatc tattattttg atagcagtgt aacgaatgaa   2100
gtactaaact attaccttg tttcagttgg ccgcttcctg gaataaagat cttctggagt    2160
aaaagcggcc tgttttcaat ttatgtcaaa ccaaaaaaaa tcagaccata ctaaaatgtt   2220
gattccagag aaagaggaat gcatgtgact taaatgacct tgtttctttt aatgtctttt   2280
tataccttta tccacattct aaaatcatat gttgtacaat gttggggtaa agatatataa   2340
atggttctca tacttcttaa ttttttgctt tcagtgttca tcagtgactg ttcaaaaaat   2400
atttatcaac gctacgctaa tttcatgata ccaaagaaca cctaattaca attgtacaaa   2460
ctttggcaat gcatatttat acattcacct atccaagagc tttaaattgg tagacttttg   2520
cagtgcattt gcactagata ataaacgagc aggggatgat aagagcgcac agctcaccgt   2580
aataaaagga gcaagtccta tcaatttgaa aagtgcaggt agggggtgaa atgtggagtc   2640
at                                                                  2642

SEQ ID NO: 27           moltype = DNA   length = 1657
FEATURE                 Location/Qualifiers
source                  1..1657
                        mol_type = genomic DNA
                        organism = Zea mays
SEQUENCE: 27
aatgattgaa ataaccttga atgacttaat atcatagttt caatacctat tcctatccac   60
caacttgttc tgatgagggt tatgacatct cagtgtctcg ctcctgttgt tcagcaatag   120
gagcctttgc accaacaccg cctttgccac ggggtggttc cctttcttca ccgtcatccc   180
catcatcatc ccccgtaca cctcgtcgtc cttaccctca tttcattcat ccttctcctc    240
atactagtgc tagcagcgga acatttatgt tcctagtata taaaacttaa atgagtcaat   300
gtcacaagaa acaatacgat gcaattcaat agcacaaaaa tgctattcct attaataaaa   360
tgttttcact gaatataaaa taagaggata tctgaatagg tgaagcatca ataaaaataa   420
cttaaaactc actgattcac tatccttctc ctgagtctca cgtgctgcat ttgttgcctc   480
ttaccaatcc tcatccagct ccatatcctt tatatcctca ccattaggcc gaggcttctt   540
gaaaaccccg ttctacaaaa aatcaaatgg cgtgaaaaca taatcggatg tctaaattca   600
tgaaaattat aacacaatga ctaaaactca caattgtgtg cctcttccga cacattgcca   660
aagtagaata tccaattgag ccagccgaca ctttgtcaga actaataata gctctgatgt   720
ctccaataag cttctcatgt gccctcttta ggaccaactg tcattcctgg tattttccta   780
tgccttttca atcttcagct aattggcttg gatatttacc agcacatcttt gaaacatctc   840
tattacaatc tctcaaagcc ctcaaaacct catccttaca aataatgtca acaatagtag   900
caatttctcc tacaagtagt ggctccaaac aagaaagccc atatgcctct atttgtggaa   960
cttcctgttg agaaacagga ggaggagtag gtctactaga aggtcctgcc ttcgtagcat   1020
cgtgtgtaga agatggtcta gctcctctca tagcaactat tttccaacca tgtcgtggat   1080
taggaatata cttcattatg ccatccttg ctttaaaat gccagctagg gaagcgcctc     1140
cccaacatcc ttctgttgaa caccgtgatg aacatcatta tatatagtct caccgacatc   1200
cttcaactgc aaatcaaaaa gcaaaaaaat acaaataaac ttcatacaaa acgattgaac   1260
acaattgatt ttgtaaaaaa agatgaaaaa gaaagaaagg catgacatta ctaaccatca   1320
acttgccata agtaaaagca tgagaaactt ggtccacaac tcgatctgcc tttgttatcc   1380
tcatgatcac atcactagtg aaaaatatcga gatcgaggtg tgcccaaagg gacatcgaca   1440
ccagacaaca aattatctaa aaagtaaaca tgtagatata caaacaata taaaaatatc    1500
taaatgtcat aatacaaaag ctaattatgt gaaatgatta tgaatcatag gataatttct   1560
aagaattat agaatgactt aaagtgacag aaacaaactc acatatattt attatgacta   1620
aaaaacatga tatatgaaat gacttaggta ggcaaat                            1657

SEQ ID NO: 28           moltype = DNA   length = 1912
FEATURE                 Location/Qualifiers
source                  1..1912
                        mol_type = genomic DNA
                        organism = Zea mays
SEQUENCE: 28
acattgcaac aatatgtcta tatatgatgg tttctgcacc gtgatgagta gcaaagccac   60
catgcatgac cgatatgcg attggcgaac ctaaaaggaa agcgcgaacg cgaccacttt    120
ggcttggcgt cttcctcgtc tttccactcc tacatgcacc ccctattcca tcgaggcatc   180
atgcatgcat gctgtcctgc tcgctaaaaa gccatggatc atgcgatgcg cacgagagcc   240
ggaggacaaa gcaaaggccc tagctagcta gctagcaagc ttttgtaaag ccgccatttc   300
cgattggcct ctacctcgaa cagatctcat cgatctcgat ctgccgcctc tcccatcaag   360
ctgtcatgag tgacaccgtc gtcgtcacat gcacacatgc gtggcgggca ggaaaaatgt   420
gcatgggcga acgagcgagc cgttggttgg aggcccgccg gccgtccaag cacgacatgg   480
agatgatcct agtcgtccgc cccgccctct ctgatatgta ctagaggcaa gtagtcctag   540
cttgcacttg tgtgtctgcc atgaacaaac acgacagtgc atgcatggtt gcgtatgtac   600
aagtcttgca tgttgccatg catagggtaa aaaagagaga gagagagcta aaagtgatca   660
tagcattttg aatgtcgtag ctattttcaa ttttcttctat tttgaggaag ctaagctagc   720
cacagatttc cagatgctat agggtaaagc tcaaatgct agcttctctc agctctgtct   780
cttgttctga gaagttgttg cacgtactag gagaagatcg attgaactct agctactggt   840
aaagttgctt ttgaaggtaa attaaagcct aaagtgtaact gatcagctga tttactagga   900
agctgagtct gcagcatggt gtggtagtgt gaagagagat atacagtgag agcatcatat   960
cgatcggcat gcatactact aatagtgctt cccacgttgt cactcgcttt ttgctctgcc   1020
ggccatatta attcgttact ctttattttg catgagttca tcagatcagt tcctctctcc   1080
ttagaccagc tacatacaga caacggtggc gagagtccat caccatcagt atctattggt   1140
atttaggatg gactaaggtc gttcgtcagt gcttaatcac accgtgcaag caatgtcatt   1200
gtacttacct ttgctttatg acatgcaaca gctgcatgcg ctgcagatgc attcacctcg   1260
aaatgcatgc atgcaccact cgccagtcgt cactcaccag cattatattg cttgtgtctt   1320
ggttttcggt cacccccccct cccctctac aaattactat agagagtgag tgagattttt    1380
ttttttcactg gacaacacga cgagtagtag cataagatat atagcctaac ataataatcc   1440
cattcccta gaagaaccct atcacttaac caccgcccaa tgcaggaacc gctttatatt     1500
```

```
taaatctggc gatattcttt actgtctgat agttcgtgcc tgtgatcggg aggtgtgcct  1560
caatcatggt taacagaacg aacatggggc ttgtgattcc tccttagctt ggccaagagt  1620
cacagtcgtc gtcgtcgtca gtcagagggt aggctactca catctatgcg aactactgac  1680
atcttttcct cgattctttt tatcgtcatg ggaacatgga gcttttcatg agtctactgg  1740
gctagctagc tagctcgtac aaccatgaga ttggatacag cctataccgg cctgtctagg  1800
aggacaaatg cctagagaat tttggaacca aactcgaaag catgggagta gttttttcact 1860
ctcaagattc aagaggccaa gtagactagt agagtgtagc tagggagact ag            1912

SEQ ID NO: 29           moltype = DNA   length = 1275
FEATURE                 Location/Qualifiers
source                  1..1275
                        mol_type = genomic DNA
                        organism = Zea mays
SEQUENCE: 29
tatagtcgat ctaatgacat agaactgtac tgactcttga aagatttcct gaacttttgt   60
ttggtaaaat atcgcgaggt caataaaagc tataagtcat cacccatta ggatgaagca  120
aagcaacata gacaaaacaa aagttaagag acaaacagca aggacactca caggaaccat  180
gataatcatt atattatatt agcgtgtatg ttataaaagc taacctgcct gcccccacat  240
attacatact gtagcataaa atattcaacg aattaaagca agctaggttt aggaccacat  300
gagcagctct gcctgtccct gccgcggcgt ccaatgggaa gcagccataa gcaacgcgct  360
gccagtaccg ccattcagat ttcagagagg ctcatgatga catcacacat ctcactttgg  420
atgggtccca cttcgccact accaacgcct gcagtgggtc atgcatgctg ccatggcagc  480
atgtgggagg gggggctcag catcaggccc tcatcacaca gctcgtcaag tgatcggccg  540
gaatggagac ggagtatctt tttccaatgg aatcccccct gcacgaacaa aggaatccag  600
tgaaggcatg tggccgcatc agacattgta tcagctagcg gttagttaat aaaggagcct  660
cagctagcag ggaatctttc tgcactgcag tttgctgccg ctgtgatctt ggtcttttgg  720
cgtcttgcct tgcgcggtgg ggtagaacaa gccagcagct gttagcagag gtggatgaaa  780
accatggtcc ttgcatgcac agagagagag agagagagag tactcaggct ggcagcagca  840
gccagcagca gagcgagggt ggtcaaggac acttgttgag atgatgtgga gaggtccgtc  900
catgtccatc tactaccagc ctgcaggaac tctgttcctg attcagccca ttcaattaag  960
ttgttagtag taggagacat gtcatcagtc gatgtgcagt acgacatgca tgtgtcttct 1020
gctactgctg tgtctccaaa ggctcatggt ttcactgtca caccgaccag tgctgctgct 1080
gatgcaacag ttgcggtggt acttcactgt tgcatctcgc attcggttgc aataccttga 1140
cttcagttta gatctatcca aaaacacgct gcctgtcgat atcttgcccc gggaagcatg 1200
gagtgaacag aatcaccaca ccagggcgat gttcatctac aagcgtggcc aacgaatagc 1260
tgtttacgta caagc                                                  1275

SEQ ID NO: 30           moltype = DNA   length = 2102
FEATURE                 Location/Qualifiers
source                  1..2102
                        mol_type = genomic DNA
                        organism = Zea mays
SEQUENCE: 30
attttcacgc gaatatgccc ctaagaccct gtccacttgc ccttgccttc tcttgcacag   60
ctccccgcct ggcgcctgcc gcctgttgac cggacgcgtg cgtccgtagc gtggcgcacg  120
tacggagtac tcgcagcgac cccacccgaa acgagccaaa aagaaccaca ccgcacaagt  180
gccaagtgcc aacaccgccg gaaaccacct cgtgctggcc catcccgaca tcccgtcccg  240
tgctcccctc ccctcctctc gaccaccctcc tcgtcgtctt cctcgccccc tccgccacct  300
ccgcccggc ctctccgctc cacccccgc ggaaaccct actccctctt ggcacaggag  360
gcctatgacg gagattcgcc gcgcgcaagg agggagtgga ttcgcgactg cgcagccgct  420
gccgtcgtcc tagggcgcgt cgagcactgc cacccccattg acgggcccat ccccacgaca  480
tccgccatgt tcgagggcca cgtatgatct cttaccettc ctccatgttt tccattcct  540
tcagcacctt tgatcgtgac cattttgat gcgcgtatg gaggaagcc gcgtgattgc  600
ctagtggacc gatgtgttgg tttagtcgtg gcgttgttct gtccgggtta ccaaatctct  660
gtgcagatca tgttcgtatt ggggatagt ttggagggt agaattcggt gcgttgatga  720
ttgacccttg gtcgtttgcg ttatgatctt cccttgagga agaattgcat gttgatttat  780
ggaggagcct ctaaacgggc aagttgtgga cttttggtgc ttatgtatac gtttgttcac  840
aattttatag ttcgactgaa ttccaactat tgaggaatct gtttactttg gttgagcaaa  900
atgccttatt tcatttggcc tacgatcatt taagtagctc atgacacatt gtctgtgatg  960
gttgcatatg gtgatctggc agcaatgtga aagttcatag ctgcggcatt tcttttctttt 1020
taaattgaaa tctcctagcc cctgttacct cccgacaata tgcacttgtt gcccttaaa  1080
tttggatatt cttctttcgt gattgcatct tattctcacc agtgaatgca gttttgagca 1140
tccacactat tatggtgaga gctatgtttt gtgccatcct actgcactgc ttgggatttc 1200
attgtgtctt ttctttttgcg tcattatgta agaaacatc atgctggtaa atagtggagt 1260
cgtgagtaat tcatgaggtt ttacagcaac tttgctcatt catggcaata gacacgtacc 1320
acttaaatgg tgaatcatgt tatgcactct ttcgctatct ataatttcat atcgaatttc 1380
tattttttgt ttttcctttt ttgactcttt catcattcat catttgtgtt aagttctgag 1440
ccatgacata gttgtaactt ttttctacag gtgctgatc tgctacgcaa atatttgggt 1500
gaatatgttg aagggctttc tgttgaagct ctcagaataa gtgtatggaa aggtatattt 1560
cttcataat aatgttcttt tctattgctt aaccttcatc tcctgcaatc cgattccaat 1620
tatttcatgt tgttatatat gctttctatt ctgctgttgt ttgaccaagc acactctttc 1680
cttatttaga caaaaaaata tcaaatctca acttattgt attgtttatt tgatactacc 1740
ctgaagttag atgaagtgaa caagttgtaa cttcttttgtt gtatgaagtg ggaatgtggg 1800
ataggtgtta taaagcttgc cgattacgtg catacagaga aacagtctta ttcaggaact 1860
cgaggattgc ctcccacatt ttactcatgt acatccttg cttggctcta agttgagtca 1920
tataatggat tactgctctc ctgcgcttttc gaaaaaaaa taatggatta ctggattctc 1980
aggcctgatt tggccatgca gtgtctctgt cactcttgca tgtatgctca tggatcctgt 2040
ttctagagat gaaataccca atggtgttct atctccatct tgctttttta accgtaattt 2100
tg                                                                2102
```

```
SEQ ID NO: 31           moltype = DNA  length = 2367
FEATURE                 Location/Qualifiers
source                  1..2367
                        mol_type = genomic DNA
                        organism = Zea mays
SEQUENCE: 31
tatggataaa taaatccgga catagtaagt gtcacatatg ttatgctaga taggacaggg    60
tagccgcaaa tactttatga acaacggtgt tacggagtca gaatagtata tcaatgtata   120
ttcattttcc tcttatgatg actacttcac ggacttgtat tgtattatta aaaatcaaat   180
tagggataaa aaaattgtga ttatatcaat caaaactaaa ggcaatatta gaaacataca   240
aaaatacatg atacatgaca cttcttagtt cttacatcct catgtcataa taccaaaact   300
aagggtcata atatatccat aattgttctt gattagcaaa aaaatcataa ttgttattag   360
aataatcatg ttggtacaaa ggcttgatta tgtcctataa atgaattata gcccaaaagt   420
taaaagaaac tcaaaacaaa acataaaaga tattaacaaa ctacaagtaa atagttgata   480
aactatatta aattgttggc atagtgtcac tgctgcatgt gcaaacatct gctgctgctg   540
tatccgccgg gttcttacgc atgtatgaga cagtgatttc atgagaaaga ttattgacac   600
gaaatcagaa tccagaaaac aataacttaa acagcacaaa gggagcagca gtgtccttgt   660
tggataccct cgtcgggaag gtgatagatc acataagaat cactaatcta aaaaacaaaa   720
cagtaagttt aagagcaaaa cagcactagt accttggcta gactgtacat tgtacttgaa   780
tactctgggt gaccaacccc cagaacacgt ccttctatct acagatggca attaaaaaaa   840
gataaattgc atacttcaac aagtgaatta caagcacatt tacattttcca ttgttttgct   900
accatgcttt gatgctttca ttgaatgggt acaggttgtta agcagcagag tgacagaaga   960
tgacaacata tattcgtata gttctgaaag gttatatttt aacctatttg tatgcgatca  1020
accaaaaatg gacaattata agtatggtca agtaagatga tagtatagca taactcaaat  1080
attgttattg tggaatatca cattggtatc aattatgaca gaggcacaaa atttcaagaa  1140
taaatgttaa acataaataa gcaagagcac aaaaagttga ggtgtggtac cttcaaagca  1200
cgctgcaaaa gggggggaaac aacaaacaga aaagggtata agaagcaagt tcaaatcttc  1260
gaatgaaaaa aattaagttc aagacttgga atgaaaaaat taagtgcaga agtatagca   1320
gcagttgaca caaagggtat aatgctacaa tggaaacagt tcaattagcc tttcacaact  1380
tcatgagaaa aatacatcaa ggatctcccc tactgtgact tcgttactaa atttcattct  1440
gtgtatcatg ataatgatgc atatagtgag gactagcatg cctcaaacaa aaagctgcct  1500
acaaaaatgt ccattcgctc acttgcagct tgaacagagt attagcatgc aaaattttgc  1560
acagatttac aaatttctta gattatgatt cccatcaaag gtaacagata ttgtcattcc  1620
tacaaactat tgcatgcggt ctgttttcaa actgtttaat gatattcacc aaaaaagaca  1680
aaaacaaact tttcaaactg tgttgcatag caaaattaca gaagaaacta taaaatctaa  1740
acaaagaaga ataactcatg aggcaacaaa acgttacctc ataacatgtc tgggcttgag  1800
caagcttgag ttgaagatga tagcatattc caagactatg cacagttctt ccaaccctac  1860
attaaaaaat atataatttg atgaattgcc aaatttagga taccatgcat ttggtgtttc  1920
aacagttcaa cacataggat caagcataga aacacattga gatagatagg aaattcattt  1980
agaatgttca tgtaggtgta gcaacgactt acatctgcag ctttatccct gaaacttagc  2040
atttggaatg tgatggctat cgtgctaaaa tgttataagt ttgtcaaacc tataacttct  2100
atggcactgt gctccagttc acttgtgtgt gcgacgtgtc tacaactgta atagcactat  2160
gctacaacac attttttgtaa atatgtactg aacctaatct atgactatca aatggtaccc  2220
ctttattggt agggtacatg tcataaaatg tccctggggc aagctgccat gtcccttcag  2280
aaaaagggga gagctagaaa agcatcaagc agaatcagag caaattatcg aacacgacat  2340
tcaggggttca tcttccgatt ggaaacc                                     2367

SEQ ID NO: 32           moltype = DNA  length = 1942
FEATURE                 Location/Qualifiers
source                  1..1942
                        mol_type = genomic DNA
                        organism = Zea mays
SEQUENCE: 32
cggttccagc agcggggccc gggccgcatt tggtggtgat gggcacaatc acccgggt     60
cgggggcattg agaatcgaaa aggccagtgg ccagtggtgc gtgcgcgcac acgctggtcc   120
acgcctgtac ggcggctcag gtgcgtgggg gcacgtcggt tatgggaggc gccacagcat   180
gcatgcagta catagagtgg cgatggcgag cgctgggggc gtcgttgggg gtgggctggg   240
ctgggcgggg gacgctggcc ccggcgacgc cacgcgacgg agcacccgac gagacggcac   300
gcgctagcta cctagctggc tgccccgccc gcccggtgtcg gccgatcctcc gttccctgc   360
agcaattcaa cgccccgtcc cgtcccgtcc cgtccctgtg gcctgtgggc gggctgcccg   420
tcactcccgg ccagctgcca cgacgtacgg gcgggggggct agctggcacg cccggggacc   480
ggactggagt acggtacggc ggtggcgtcg gcgcatggat ggggtggggg tgggccggat   540
gcttctgctg cttgtggtgg ccaaccacgc atccattggt tcatccgatc cggacaccac   600
accacacctc ccccgcccccg cacgcacgcg gtgcgggagt gcgggactag cctgtcgctgc  660
gcgtggcgag cgctcaacgc ccgtgccgcg ctgctggtcg ctggtcggtg ccagctgcc    720
tataggtggt gatgacggtg ctgctctagt agttagttct ctactactac tcctagtctc   780
ctagctcact agtgaatgct ggttgcagat ccgtgtggtg cggatgcagt acggtacggg   840
cgcggaggg atctcgcgtca gtggctgtcg gggcctcgtg gggagctggg gggaatggga   900
tctcgcgcct cggtgcggta cgctcgggtg tacggcggca tgtgcggccc ttactcccat   960
ggaatcaaat caatgtccgt cgtcgtgtgc tctggcaccg agccgcgt ccagtagcgt    1020
cgtcgtctcg tacgccttgg cctacgccag ctacgcgcgg tcaccacgca cgggaacggg   1080
aagcagtgca tgtaccttg gctagctagt agtaggcatc tacccacgcc atgcattctc   1140
cgcgccgcga tctgctgccc tagctcgtct cctctgctca cagtcaccgg aatgcatggc  1200
gtcaccgcca cgcaagccat acggagcagc gacggtcgat ttcatcaacg acacgacgga  1260
gcgatgaccg caacaaagca cggtcggtcg gtcggggtcc tgagcgcgtg cgtgcgcgcg  1320
caagcgcaag cgcaagctgg ccggcggatc aggaaatttc ggagcggaca gggacgggtt  1380
ggccagtcga cagggggcct ccatgcacaa gcgattgtgc ggccgtggtt cgctggcggt  1440
ggcggtgccc ggcgcccgcc cgctgggcga tcgatcgatc gatcgcccta ccacttcttt  1500
```

```
gtgccgctgt tggttgtgtc acgtcctcat ggccggttgg ccgggccccg gtcctggctc   1560
atcctgcgtc caagtgcaag ccgcgagtaa agtaactgtg tcctggccct ggctaccact   1620
ttgtgccgct gtgttgccta gtgaccgagc tcgcccagcg gggagaacag aactgtgtct   1680
tgtgcgtgcg gccagctgtg tggcgcgctg tggcgtacgt cgctctcccg cgccctgtgc   1740
acgtgtgtgc gcgcgcgcgc gtaaccacct ttttctcgtt ctcggcaaca gcccggcact   1800
gcaaatcagc aggcgatcac cgcccacaca gctgatgccg atcgagcgct ctgggcggca   1860
acgcgcgctg ttgcgctcgc tgttcgtctc cgacaaagaa aaggtggcgt cggtgttggc   1920
tggtcatggt taatcatgtc ac                                            1942

SEQ ID NO: 33          moltype = DNA   length = 1994
FEATURE                Location/Qualifiers
source                 1..1994
                       mol_type = genomic DNA
                       organism = Zea mays
SEQUENCE: 33
agggatccta actgcttgct ttcgaatgta acccaacaga ttcacgagat aggctaccaa   60
agagatgttg tttcgacaga caaagaaaa agagtgggat atcttcgtct ataataaatg   120
agttagatgg cgagatgtta tcagaatacg ctttgggattt aagtcacggg cctgacacgt   180
gtgagacaac cttgccatcc tccgacaccc gtccgtccat gtctgcactg acgcctccga   240
gagcgcaacc tgccaacaca cgctgacgag ttcagacgag ccgagcccat atgatatgcg   300
gccatgcccg tgccgctgta aggacttctg aaccactggc attagtttat ctaacctat   360
tacattaccc tgaaagatta gcgcctgaaa gatttgcctt gctgctaaag catgcagtga   420
cattgcatcc agcaaaggac agcacccagg tgacaaatgc atttctctgg ggggcgaatc   480
acgaatccat ggcaacctga cgggctgcct gctctgccaa tactggtcac acttcagtga   540
caaagggcat cagaaccaat gcaagaaatg gtcggtgcgt ctgaagaaag atgagagcaa   600
gcaggcaggc cgtcgtggtc tcttaaaatc gacgccggta gactttttat tttatttta   660
ggtggcttcc caagaatgtc ggcacgcgc cgagcttcca tgccgtggca ggaggcgggc   720
ggggcgaggt gaaaaggagg gcggctctcc tctgacgctg ctcctccacc ttacaattaa   780
aatatttgtt gggtcgattg gatgatggc gtctgtcaac agctaatgga atcctcgaaa   840
gccaagtctc gccttttttt ttcttcttct cagatctgca gtgcagtgca ggcgctattg   900
aagccatgtc tcgattggga tgattgctct tgctcgcccc aggatccgga tctttctgaa   960
agttttggga tggactatcg ttggtgtaaa agtatacagc tcactgctct tttcatgttc   1020
tatgctatat gtattatata cagagagaga gagagaggg tgagtttgga ggtttagata   1080
atggataaga gagcttagcg atccagctag gatcagatca tcagaaggcc aaaaacctcg   1140
agagccttac acttgacaaa tgcttaagga ctcacgctta aagcttcaaa agacaacaaa   1200
gtggcagttg gttctcaggt aaagtacaaa tagatggaaa caagtcagtt ccatctgatt   1260
gcaacatttg gagggtgaca atgtattttg agcttgtttt ccaaacataa aaaacatgga   1320
caggaaaaca caacaaccaa cgtcagctgt cacttctaac aacaggctac caaacagtgt   1380
gacatataat gcaaggcaga cacgcaccat ttcaacgtac taccataaaa ccagacccag   1440
tgttctgaca gagcactagc acactgctac gtgtgcagtt aattaacgga gctgttgggg   1500
tttgactgca aaggtgcatc caacatccaa gcagcaaatc tgacgtacta gagctcttat   1560
gaacagcacc tgaattagcg tatcatatct gacgaaaacc aaaaggtact gtacctgtct   1620
ctccgcttgt aaatgaaatg aattgttggtt ctggtatttt gatctctgtt tcttggaggg   1680
cgtgatagct ttgcagttag gcaaggcaat caccggggga tgatccagtg cgttgttcta   1740
accaaaaggg cagtaaaccc aaccactcgc tagaggtaca agaagttcag gttgcctagg   1800
cgttctgtcg caactgccaa cagcaaaggg atctgttggt gactgcagct ggatctgact   1860
ctctgagttg agataatcgc ctactatatc ctgtcagtgt caggtccaat aaacagtctc   1920
actcagatat ttggtatcgc aacatgcgga ggatattctc gtcgaaacga aatgcaatta   1980
tccgtggatt atca                                                     1994

SEQ ID NO: 34          moltype = DNA   length = 1898
FEATURE                Location/Qualifiers
source                 1..1898
                       mol_type = genomic DNA
                       organism = Zea mays
SEQUENCE: 34
tatatttgac actataacaa atactaacat attttttatg cattgagcgt tgctgactct   60
cgtcaacata tctcagaccg atggattttc gaccggacag agaaagcaaa ggcctgcagc   120
ctgccggggc gttcgtacgt acgcgctact tgtcatgagg cggaacgagc gagagcattg   180
aagcgccgcg agcaggcaac ggatttccc agcagctata tagcctgtag agaggcgctg   240
aaaagattga tggatcgacc agcactcagc gctctttcg atcgtgtcgc atgcatcttg   300
actagtagca gcttgtttgg atcggagctg cagcttatt catgcgtcgt cgtcgtcgac   360
cgctcatcta tctgcgcgca ttatatagca tctgctagct actactagtg cgcatgccac   420
gcgagcacat cattcggtca atgcagcctg cacagctgcg cgtacgtgcg ctgctgcatc   480
gatcgacgat ccgtcgccga ttaattacgt atactctggg aagatagata tactgtaagg   540
ctgatgcctt ttttctgatg agccattgg atcgatcgat gtgcatgcgt gtcgccagaa   600
ataaagaagc atgcagccaa tcaagctagt gtgtgagcaa cgccgcaggc aggccaggca   660
tgaatgcgtg atgcgtctat taatttgtcc catgcatatt atttactgtc gtgagaaata   720
tggcattagc atgcacactg ctccactcgc caatgggcac agttgctcat cagccatcaa   780
cttttgtttt gtgtcagcgc atgtatatat gtggcggcta gctgtgttct cgctatcatc   840
aatatgcagc agagagagat agaatagata gattgacagc tacgtactac tagtgtgtat   900
ctacatagat gtacctttgc agtgcagaga agatacatac aactacgtgc tgatatgcat   960
tatgcatgca acgcactgcg cacctgtcag tcagggtacg tagcagcaca tgcactacac   1020
tgtaccagca ggttttttcc ttggatcatg tcatctgtgt tacgtgtggt aaaactctgt   1080
atccgatcca ggacgaggac gaccatatca cctcacctga tctacataca tatgccatgc   1140
agtgcaggat taattattgg cctccatgca tgcatgaatc ggatcccggg acaatatccg   1200
gacacatgca tgcttgaatg gacgtacgta cgtacgtgca tgtgtatatg tacgtgtatg   1260
taattatgta tgtaggtgtg tatacctagg cggctaataa ataaccggat gtgtatactt   1320
gtgcaagacg atttaattac tacttagata tgatcttgca gaattaaacc tactgagatt   1380
```

```
agctaggtat ttaggacgac gagatatata cctagctagt agtttgtaaa gccatgcatg   1440
actgcatgag cttctggagc tagctagcca gctatctgcc ggcggctacg ccgcaaacga   1500
cactggcacc gcgcggtcgt cagggctggc ccaggcagca atattgcaag ctgatcctgg   1560
ccattgattg gtcggccggc ctcgcgcgca ggctcaggtg gcttctgcca ttccggtcgt   1620
ggcgcgcacg ggtctgtgtg acgatgatta gggagggccg atggcgggcc atatatattg   1680
cgaccgatat catttggcca ggtacacggg ttaaattccc attcaaactt tgcctacttt   1740
tttattgtat taggctctga ttccgccagt gatggatatc agtgtcggct caaaatccga   1800
cataattgct agaattggat ctggttttg gggtagtaat tgacattgat gaggcctccg   1860
ctgattcctg ttctccgaga cgatagcgat agagagat                          1898

SEQ ID NO: 35            moltype = DNA   length = 2417
FEATURE                  Location/Qualifiers
source                   1..2417
                         mol_type = genomic DNA
                         organism = Zea mays
SEQUENCE: 35
actcaaatta ggcatccatg gtgcaaccca aatgtgttgt caaagttaac ccatacctta     60
gatctagaat tgctgacact agatccatat ggtgtcccat cttcattggt tctaggagta    120
gcatcattga cttatagtga ttgtagttgt ggctcatcat tgctaagaac atcaatcaga    180
gtggaagtaa tgccaaatag ctcttcatgt cgttcctcaa agtcatcttc atcgtcacca    240
cacatcctca acttatagtt gctagggtta ggatcatcgt ctatcacagg ccctttggta    300
cctcaatagt ggctactgca caacaagatg catgtgactt gcaagaagaa gacattctta    360
catgtttcat accaagggga tacatatgta gtcagggtta ggtcatatat tacttgcaca    420
aatacaacaa atgtttatga ccaagatcca tggatctatg taaagagaat aaactaggtt    480
tttaggaata gctataaaaa acagaaggag ggaggaaaac atggaggcgt gcagagggga    540
gaagactata gatggcccaa ataggagct tcttaatgcc ttagtgaccg tgactagatc     600
ttctgaggca gcaactagag acaaacatag aggaaatatg tgtgtaggaa atgaaggtg     660
gagctatgga ggtaagaggc atctttggtg gtcatggttg tagatctagc gatgaggtag    720
ctggagacat ggagagtgga gcgaggagat gaggatgaga catcgatgga ggcaagcatc    780
tatggctaca gggtgatcca tgctagggtt atacaaggtg ggaagggga ctgagtgagg     840
ggaggcgagg atggtatatg ttcaagctaa tatgtgggga caaggagtg acccaagcat     900
gaccccgtag tcatggtagg cgagtatggg cccaacaggc ctgtcgagct aaaaccctag    960
gccatgggtt gtggggattt tgaccatcta taggtgattt gtcaatgttt tgtccattta   1020
ataaggtct atttttacaag gtttttatga ttccactttc acaatatttt aaaaacctac   1080
aaaagaatcc atgtcggcaa cacaaacgac cctagtttac taaacatttt cccaatcaaa   1140
acaaatccta ctagagaaat gcatgttcct tagaagaaat ttgaacataa ataatattca   1200
agaaacaata caatattcct accaaattga cccgacatca tccctcttga atatgctttt   1260
tattattatg ttgttatgaa aaagattttg cagatagttt gaaagacaat gatatatttg   1320
cttaaacgat ggtttgaaga atgatgagtt gtttgggtgc aacaaatcta gtggtagtag   1380
tttggaagac aatgatatat tgctaacact agtgttttg gagttctaaa gatgacttag    1440
gcagggtttt aggatttgga ttggaacata aaaaatcatc aaatttaacc aactttggtg   1500
aggctctatt taatatcaaa caagtaaaaa gttttagtct aatttgatta ttttttctcac  1560
aaaagtgtaa gaagcctaca tgttcctcct tcatcatata agtgtaaacc tagaaatcca   1620
taaccattgg ttatgaactc taagtcaaaa tttgaagaca ttttaactag atttcattaa    1680
aacatgcctt tttaacatga acacctagaa tttccatgat ttatcagttt taatgggcca   1740
agtccgtatg ttccctcatc ttgatcatgg acttgtattt tttggtaaaa aatagtagct   1800
aaaaagctg atgtcaactt tcacacaaga gttaagggg gctaaatgat catagttaac    1860
tcttgataca gttaggacac ctatgcttta taatcctaga taccactttg gccaaaaaag   1920
atactgaagc tcccctttaa gattaaagta ttcatttggt atcttaaaga tagaagtgtg   1980
ttgttgtgac taaaatagac atttgatcac ctctttttc taaaactaag atatttcgaa    2040
gcttgttcat attgggttta ccgcatctag atccattgtc catatgcttg gaagttgtgt   2100
ggtgggcatt gagagggttg gaaaaaacct ttttttgaggc ttcttgctat tatttggata  2160
atttggtgtt acacataata atttcgttgt ttatgcttga gaagacacaa aatgcttcat   2220
ttatgaatgc tacaccctgt gaacatatt ggttgtgctt tatatactct attgtggtat    2280
gaggacaaag gggagcagag tgtgaggaca tagggagaag gttcaagtgg taaaaaaagt   2340
gattgtagac tattgctttg agcgccttca actaaaatga tgtcatgaac taacaaaact   2400
ttggatttga ttttctt                                                  2417

SEQ ID NO: 36            moltype = DNA   length = 1589
FEATURE                  Location/Qualifiers
source                   1..1589
                         mol_type = genomic DNA
                         organism = Zea mays
SEQUENCE: 36
catgattgct tggatttatt ttcgttggca aaataaatta tattcctatg gctttcaaac     60
ggtgtccagg aattccacct gagagaagag ggtgccatgc gctgtgcatg aaagaaatt    120
ctctctctgt tttttttca atccaacaaa ggagagtcct agcctaggcg tgtcgttatt    180
ggtttctcac gtgatgtcgt cctccctgta gcaagcgttt aagcgtcaac gattaccgcg   240
tcgctatccg tcgccgttgc gatgcgtgga actgtggaag gcccggaaaa ctggaatatg   300
ccaagaaaaa aaaactgtca ggatcgtcag gccccactga acctcggtct ccgtcgcgag   360
gaaactgccg agaaggtgta agtaaacgct tgtgatatcc tctgaacgtt gttggatgat   420
caggtcgcag ccacgtgagg atttacgaaa attctcgcgc ttttctttat ctactagtac   480
tactatttcc tcaggtcgaa aacgacgccc atggttgctg ttcgggtttt ttttttcttc   540
tgcttctggc attttttct cgttgtcgcg atttgatatg gctggagttg gtgtcaggac    600
ggacggggca ggttcattgc acccacgcca caccccggccc tggttcgtcg ttttttttga  660
agcggaggca tccgccatct gatgatcgaa tcgaacgagg ctaccggatc acgtctgaat   720
gcgatggcct acaaaatgag caacggcgat ggagcggatt cgaggtatga aagggccttg   780
ttgtgctaga tggctgggc tgcacccgca cggccggctc tgtgctgcca gctgccact    840
accggtatgc aaatgcaacg acaaccacca gatcctcatg ggggaaaaat acgagacgac   900
```

```
aacgtcatag agaaacactg tagacgtctt ctttctctct ctctctctct cttggaaaat    960
agtcggcaag agcactgtta tgtactccta gtactgtagg acatgggaaa aaagaaagct   1020
ctacgctctc cacagtagat taccggcgcg cgcagttact gaactcctcg agcagcacgt   1080
gcgagcagtg gaatgttcgg ggcaggagga agcagaagca caccacgagg tttcctctgt   1140
cagtcgtgtt gccaccacca gatttcaatt cgacttcgtc gcgtggtgct tcatgtacac   1200
gacaatggaa ccaatatata tattttttta ttttttttggg gtcttgatcc ggtcggttgc   1260
ggcgtcagag agccgcgctc ctgcaatttc agaatggaca gtgtctgtaa cgccagattc   1320
cctccttgac ccatgaggaa tggatcaaac caatttagaa acaaaaaaaa atgcaggtac   1380
atatgcgttg tgtgtcgacg gcatgcgtgg tgaaatgaac cacgtgcagg ataacgagga   1440
cctgaagcta gtagcgatcg gctatcatca gcacgagtca aatatacacg aatgcgtgg    1500
cgtgcctttt ctgctctcta aagtttcgaa cgcagcagga tcatcaagac tcaaagggc    1560
gcgaagcagt tagttgttgt gggactcga                                    1589

SEQ ID NO: 37              moltype = DNA    length = 2299
FEATURE                    Location/Qualifiers
source                     1..2299
                           mol_type = genomic DNA
                           organism = Zea mays
SEQUENCE: 37
taaagggaga cgggacaaac gagtgtgatc cagatcgtga cagcaaaatc tcgcactggt     60
gaagcgtctg tttcagaagc taccacaccg gtcaaaagta aaatcataag ctcttccttg    120
atccttccgt ggatagttca ggtaaattct aaaataaaag cggcttgtat gtgttctact    180
gttcttatcc acgcgttgac agacagacgt cgttgtcgtg gaaacgttgc cctaccattt    240
ctggagcggt agcagattcc cttttttgcct acctccaatc aacatgcatt ctcgtctaca    300
caaaggtgat atggtcatga tagcatggcc atgcctccat ctcgttgcca tcccttccgg    360
catgagggtg gtgcggtggt atgcatgtta gctgcagaaa ggaggacagt cgttcttctc    420
ttgctgtcct gcacaactga aagatggaaa cctgaaatat ggtaaagaac agcgcggtac    480
caacgtggct ttcgcgactg cgatatgcac ctgtacactg cacccgactg gaaccacaca    540
gccagtagca agtaggcatc atggaatgaa atcaccggaa caattttatt tttattattt    600
cccgaaaaga aaagggaatc acaggactat atacactgcc cccacacagt gtcacaaagt    660
ccattccggc aactgttccc aggctgcttt ctccgacctc ctagcctagc gatgctcgtc    720
gtacacacat tattccgctg cgctatcttc tcccagtgaa ggaaaccgag agggatttgt    780
cacaggagca caggacgatg tactgtgtgt tgctgcgatc gcaagcgata acagcgattc    840
atggtttgga aacacatggt ggtttgcaag gttatgattt atactattat atattctttg    900
tcagggacgg taatgctgca tcaacacaac agcaacgcga gtggtggact cgcgtctcgg    960
ttgttcgacg gatcgttaga gaccgaccaa atcagcgagg gagcatgacg agacaagcag   1020
atagtttagc acgagtacag gacaagccag ctttgtcgtt gtaacggtga ttacatctac   1080
ctgtcttgta ggacaggcta ggctagagta ggacggatcc aattggaagt ccctatgcat   1140
tattgtgtgg gccgggccgg gatcaagccg ataaggtgat aagtaccctg ttccaccttt   1200
ctagatggtt ggcgctcacg agtaaatcta ggttttgtct aaagcaaaga cggcttttgc   1260
tttgctttct catgtgcgtc ttcagagttt caggcgatat gccgcaaagc aagccgaagc   1320
gtcctgtcta cccgagatat ggctttttttc actgtatggc agatgagaga ttcctagccg   1380
ataaaagtca gaccacttgc tcggtcaaag cttttgtcctt agcattttgta tgaggctaga   1440
gagcgacata ttctgatcgc catttcgtgg gtgcgcgcgc tgctcaacaa cagtcatgtg   1500
ccttttttta aaatctactg tagtcagatc cagctgcagc tgatgtgaca cggtctcgga   1560
gagccaggcc ttaacgaagg gggcccaaca taatatgatc ctaggaggcc cggcaaatgt   1620
tgggccggaa gaactgtatg ccggcgccat tccaattttgg aaattcgttc tttgttctgc   1680
tgacccaag tctgaactct gaagtagttt ctcaatcagc tcgagctgaa aatattatta   1740
attcgccaac tagcgaggtc tgacgaacga ggcgctgaga cattctcgga ttctccaact   1800
gctcagaggc gctgagagtc tgagatagac acgagtcagt tgcttgatca ttccgctaac   1860
cgctataaca ggatatgtgt agctcgcgtc gtaaaatcgc aacactggaa ctgttcaacg   1920
gggggacatc ggaattaaaa aaaatgtcgt ttgcaccaaa aaaaggaaca aaagagttaa   1980
ttcttttctc atgcgtccat ggtccagtcc atagggctca acaggcgtg ttagttgtgc    2040
acttctttcg tggaacattc ctttcgtggt taactaggag ccaaatagat aatgtccgta   2100
ttgtctgatt ggcaagttgc tgattaagac cgtcagaatt cgcagacgta tattctctcg   2160
cctcttgctc ctattccttt tggactttcg gttcagttg gaacaaagga cgtccttgta    2220
cggtcagact cgcatcacgc tacttactaa aatgttacgc gggcatcggg cttgtgtggc   2280
tccgttctcc acgcgcgtc                                               2299

SEQ ID NO: 38              moltype = DNA    length = 2603
FEATURE                    Location/Qualifiers
source                     1..2603
                           mol_type = genomic DNA
                           organism = Zea mays
SEQUENCE: 38
ttgtagtgca tagttgctta attattcatc tttttaaacc agagtctaga gataagtaat     60
cttttgtcca ttgctggatc ttctgttctt aaagcttcat ggcaggcttg gaaattagtg    120
tgtctcatat gtatcttgta gcaggcactc tttcaagtgg cgacaacaga atggatgatg    180
atgtgattga tgatgaagaa gatgctcaga gaagaagatc aagatccaaa aagaatgtgg    240
tgaaggaagc taataatcca gcagtggcct atcaacttca cccacttaaa attatacttc    300
atgtatatga tactgaagat tctggtagca aacgccgtaa actcatcacc ctgaggtttg    360
aatacttggc aaagttgaat gttgtttgtg tcggaattga agattcagag ggtctggaca    420
gtaatatctt gtccaaccta tttccagatg acactggttt agatctgcct caccaggtat    480
gtaatttaat tcgaagcaga tggttttgat tgctagttac accatcctta tggaagtttt    540
ggtgtttgtt tatgtaccta cctgtttttg gtttatttca gcctcacagg cctttaatgt    600
gattttagca gggatatgtt tgttactac atctgtatct agtatcttct tggggcctct    660
catttacgtc agctgaaata gtgacttgtc aattttctca gatggctaag atttatgttg    720
ggaggttcc aaacttcagc gacaaggatt caaggccata caagtgggca caacatttag    780
gtggtatcga cttttttgcct gaagtgcctc catctgttgg ggatgattct agcagagcat    840
```

```
taaacactgc tgatttgtca tctgggcttg ctctgtaccg tcagcagaac cgtgcacaga   900
ctattttgca gaggatccgc ttgcggaaag ttgcacagat ggctcttatg tgagtcactg   960
gtctatgttt tttgctgttt gggacatcga tgaaaaaaac cggatggcag attagcctga  1020
gagtgaccgt gtaatttgac tgacgatttt gagctaatga tgcttttgct tcattgcaca  1080
tgtcattctg agttatggca atactatgaa tcatttaccg ggcagaaatt gtgaaacata  1140
ccatttatat cttcttcata tgttctctac atattgattc aaagctaatt attggcgacc  1200
ttcattataa tgttattcat gactgttata tacatggcct gtttgattgg tagcatccct  1260
ttgaagtttt cgagtctctt tgattacagg tggcaacttg attatttgac aaagctgaag  1320
tggcctcgaa tagaacataa gaatgcacca tgggcatgac gcaacccact gtgcagtcta  1380
catagttggt cattgacaag ttatcctgag tcatctcgtt ctattttgat gctaagtggt  1440
gctgcaagca atgttgacag tgatgtagag agatctgtga caaactggga agaaactgag  1500
agtatcaggg aggatgggga gcttccagtt gttattcctg ctgagaatga gccaaatggt  1560
tctacaattt tgcaacctga ggtgtcagct gagatccgga gccattctag aggcttatct  1620
cttatatcaa agagtgcaac accatctaag ctaagcatct cacgaagttt tggtagaaat  1680
gaggacgatc ttgatctctt gatgtatagc gacagcgagt tggaggacca gccctgcatt  1740
cttgacgaaa ctgaaaaagc tactagcccg attagagaca gattctggga ggagtatgct  1800
tccaaggaat tcaccatggt cctgagtaaa actatgaaga atggtctaaa agtcatgctg  1860
gaagccaagg taaactatgt catcactatt tgttctaagc cttcatgcat ctctccatgc  1920
tcttgcttct gacattaaga cttatcacag gttaagataa gtatggagta tcctcttaga  1980
cctccccttt tcagattacg tttgctctca gaaaagtctg aaattttgaa gtggcacaat  2040
gatcttcgtg caatggaagc tgaggtttgt gctaacatat cgtgtaacat gttttattta  2100
gtgcatttct gagggtagct cttaaagctc actatcatgt gtgcaggta aatcttcaca  2160
tccttcgaag catacctcta tcatatgagg attatatatt gactcaccaa gttatgtgcc  2220
tggctatgct gtttgacatg cattttgatg aggaaaacga gaaagaaaa gtcacttcag  2280
tgatcgatgt tggtctttgc aaacctgtta gtggaactat gcttactaga tcggttaggg  2340
gtagacag aaggcaaact atttattgga gaggtgctga ttgctcttcc agttacttgt  2400
agagtatgtg cgatcttgat tggtcttggt tgagttcagc attgactacc ctctggagaa  2460
atctttctg ggcattggag aactgcatat ataacttaag agctgacaca gatcccttg   2520
tttatcacta ctgtgtcttg acagcaatag ctgggaagat ttctctgtgc ccatactgac  2580
tcgagaaact atttacaatg ctg                                          2603
```

SEQ ID NO: 39    moltype = DNA  length = 1609
FEATURE      Location/Qualifiers
source       1..1609
          mol_type = genomic DNA
          organism = Zea mays
SEQUENCE: 39

```
cgcactctgc actgcgctgc gcttcatgca tgcatgctgg atcgatcgag ctcgatcact    60
tggaccaccg cgatgctcga tcatgctctc cggcctgcga cggccgccca gcatcgcaac   120
aagaagaaga acctgctttc gcagttacca tgcatattca tttattccac cccatcgaac   180
gcgatccatg atccatgcat ggccaccgtc tgatctgagc accaacacag cccccccatg   240
aatacccatg caccctacc tgtaccggat catcgctccg tggcttccca tattattctt    300
catttctaaa ctgtatgtac tagctttac tatatacatc aatatataa ctggtatatg     360
actacatata atatccaccac cacaccggtt ttttaatcac tagctaatga aagattttcc   420
taagcacaaa agggtaaaaa gaagcttgcc atatatatag atcttgacat gtgtgtactc   480
taaaacagct tgagaaaaac taaccccttca gcaataaaaa aggctacttt aaagaatatg   540
cttatcactc gctgctagga ataggaacaa acgaactaaa gggaccggag ctagcgatcg    600
agtacacaat tccttttctt ttttttttac ttgattaatt tgaaaacccg aaaggcgcct   660
tttgggtatg taggccggca ggagccttgg cagcatggac caaataaatg tgtatgcgct   720
gctcctagct agagagaaca tgctatcttc ttggcaagtc tctgtctctg atctctccat   780
gcgtgatggc cttacctcat cccatcgtat ttctgcagact cgatcgacta gttatattca   840
gcactaggag tactatatat actatatgca ttttttttgt tacttgcttg tccacataca    900
caatgatcct tgcatacttt gctttctagg cggcctccat tatattgcat atatcatcat   960
catcatcctc atgtgtgggt gcacattata ttatttctat ctccttatgc aacgatgtgt  1020
atgtatgtat gtatgtatga tcaattgatc tgtccctagc tcccgtgacg atatacaaac  1080
atttacacgg cgagtttgg atggatcgat gtgctgtgca attgcaacaa gcacgatctc   1140
ggatgcatgg ggatgcatgc agacagaaa gctaggccga atgaaagcaa gattgcatac  1200
atggatccaa gatgcgattt ttatccttgt tgtttggtgc cgcctgtcct agttgccaag  1260
gcgagcgtat gtatagcatg tacaactgtc tcaggcagat gcaggcaggc aggcatatga  1320
tgctttttatt tgcaggcaca ggcatgcaca ccaccacacc cggccggcac cggccagtgg  1380
agttgcctat gtgatgagaa attttggagc tttccttgcg gcttcggtat ggtccagctt   1440
ttatcatgcc aacgactaac attccctgtc ttgctgctct tactgagatg tataggtagg   1500
taggtaactt ctccaaaata aaatacacat tatgttaatt atattgctcc atcatgattc   1560
atatgattat gagaccacta tattattcta tactatatgt tgatagcta              1609
```

SEQ ID NO: 40    moltype = DNA  length = 1794
FEATURE      Location/Qualifiers
source       1..1794
          mol_type = genomic DNA
          organism = Zea mays
SEQUENCE: 40

```
acttttcctt gaaatcaatt aaggggctca gattttatgt ggcctcttac cttctagaag    60
ataatgagta gtgtaccata gcaaaggcca tgtgatcata ctggatcatc taggataaaa   120
catatgtgtc aagtagacat tgggctatac acttattta tatactctcc gatgatgta     180
ttattataac aacatatac taataaaata tatgctctcc tttgatttta tttccatgta    240
tatatagcaa gattaattta caggaggagt atcttaaaat gagcatattc aaacaaataa   300
aaatatacac tttgtccaat cgtcatggac ctgtgactag ccacttcacc tatatatata   360
tatatgcata taaattacac acagaaagga gttaaacaaa ttgtcaaaag ggagggtgat   420
acggtaaaat cgatgggcca acggaaaggt agagcgtgac gtgcacgacg atggctcgat   480
```

```
cgaagcccctt ccaccaactt gtgatttatt gactaattaa cgccaagtgt caagtcaaac    540
ccacagcaga gaaagagaga gagctagaga gatctagaga gagagagaga ggggccagga    600
tggatggatg gatggatgga tcaatcacgc actaatgagc tagcgcaacg caaagggcgg    660
gagagagaga gatcgagcag agcattttct tgcatgcaat tatatatctc gtccgtggcc    720
ctctcatttt attttcgcgc gcgcggatgc ggggccggga ggccaggaa tcgacgacga     780
cgacgcaact atttcatggt cgggcgcttt attttatggt cgaggagatg atgccgctag    840
cttgcactat tatttggaca aatcatcgtg cagcttttaa ttgtcggcac atgacctttt    900
cctccgtgcg atttgtgtgc gtgggcccgc cgccgtcgtc gtcgtccctc cgcccgatcc    960
catgcatgtc tcaagctctc tctacaccat gcacgcatgc atgcatgcat gtgtgtatgt   1020
atgtatgtat gcatcatgta cagctagta ggctccattg atacatcgtc aagcttttcac   1080
aactttaagg aaataagtat gctcaatata tatatactac tactatatac tactaggacg   1140
gagatcgaca aggaaattaa aaggagggaa gagatcgaga gagacagaaa gaaagagaga   1200
tctcgtcgat cgagagatcg tgaattctta attaatcaat tcatcagcta attatcaagc   1260
gttggttcct agtcaaatga gaggatcgat cgatgggcca ctagctagag gtcgctctct   1320
ctatactatg cctagcgcta gttacctata tgatgcatga cgacgaacct ctccggctcg   1380
tgtggcgttc gttttttgttg atcagtcgct gctggagttt ggacgataac taagtgacca   1440
caggagattg gccggccgac ttattatagt tttcagcagc agcagcagat attatatttg   1500
tacgtatata tggacatatg tatgcgaat cttatcactt tcactatttt aatttaacta    1560
gcatatggca agcaacttga tttttttattt taagcacttt caatctgtag tggtcgatga   1620
taccaccga ctctgcattg tttatttgaa aattttttat gataatctaa gaccaaaaca    1680
acaataagat aaaagcgcat gaatacatag ctaacttttcc catcaaataa aataagcgat   1740
tggttccaat acaaatttag agacaaaaat aagtatttta agattctata ttaa           1794

SEQ ID NO: 41         moltype = DNA   length = 1898
FEATURE               Location/Qualifiers
source                1..1898
                      mol_type = genomic DNA
                      organism = Zea mays
SEQUENCE: 41
aggcgacaac gatcgcaacg gattaaggcg ctgagttgag tttcgtggcc actcataccc     60
ctccaaccac cactagaggt cacacatgag caccaaagta ggaggaggag gtggtaacga    120
cgatggcgat gctagtacg gcaagcatgg cagagcgtga cgccgctgag cgttgcatcg     180
gcaccactca tgaacaccgg cggtggtccg agggtcgctc tagaactact catcaacacc    240
gatggcaatg cacttgaagg caacgtcact tctgagcctg gatctagcaa ggacaacagg    300
tttgttctcc ctattaccac ctcaacagtg ttattgctgc gatcttacaa gccctgcaag    360
gtcattgtgg cccaacttcc tttagtgaag tttgagtatg ctaaacctgt tcctaggaag    420
tttatgtatg tgttggccta aattgcttta cttagggatt atcttattca agatttcgtg    480
gattttgcag catttttacac taagaaatta catttaaggaa atactttacc aatgctagga    540
ggaaaatttt gagctaggat ggcaataggt tattgtgcaa agtgacatta ccaaacataa    600
ataacgtgag agttaagatg acagatgaag gtttgcttat cgagttgggt gtgcctatttt    660
accaggaatc atgttacgaa caagagttca aatagtgagt tcacattgga ttcattcgtt    720
cttttgtatg gacaagctca catagttaaa cttttccaatc tccgcttgac atccaataat    780
gaattgctaa aataattagt gaaaattgct aatttgattt taagggtctt cattcttttac    840
gaaaagtaac caccctatct gaatcactta atcaataagt tgaataaacc taaattaaac    900
cccgttttga atcatatagc gtgccaatat aatctcacta ttcctacttt acatcgatgg    960
gtcagttaaa tgtcatatat caggtgaata tcaaatacga tcatttttgga aaattgcaga   1020
caaacatgtt tagaagtgtg attgaactta ccaaacttga gtcgggttgg ttaatgaggt   1080
tacgacgtat tgtcatattc agtagcataa ttgagtgcag agtggagacg gctgttgtaa   1140
taagaataat gacatatgtt aacacattaa ccggtgctttt tattctcaac agaaattata   1200
acacacatgt tttaaaaaca ttgtggattc caatggaaat cagttataca gtattagtgg   1260
aactgaatta ttggtttaca aaactttagt gactttctag cagatatgta gtttaatctt    1320
atggacaatg atttttaaat acatatagat gttaaagatg tagaaaggaa ctatatcctg    1380
tcactcactc aatcacttaa gtgctttata aaagagtgaa aaacttttgac tcatccttca    1440
tacaagtaca aattggtgat aacatgattt caaaagttat gttaacaaaa atagaactca   1500
tactttttcat tagtgatcta gacaaaagta agaatcaaag atgcaatggt tagtcaagcg   1560
acgattggat ttagatacat ggataaaaga actcccaaca atatatatgt ttatcacata   1620
tggtgatgct tgatatgaaa ctataatcca accgaactaa ttaatctgat gtttgatcta   1680
tacgttttga taaataaaat aaaatgttat aatataataa tatattttgt tttatatagt   1740
atttttattttt ctcgttaaag tttatatatt attttctgtga ttgagttatt tcggtgcaaa   1800
aataatatat tttgtttatc acataatatt ttcataaaat aaaataatga ttgttgtttt    1860
tttacgtatg cttgagtttg tgtgagatat agttggtat                              1898

SEQ ID NO: 42         moltype = DNA   length = 2594
FEATURE               Location/Qualifiers
source                1..2594
                      mol_type = genomic DNA
                      organism = Zea mays
SEQUENCE: 42
gtgtggcccc ttcgttcatt tgcgcgaaag cggcatgatt aggccgagga atacgacccc     60
ggcgagtctt tttaaaatca tcggcggggg cacgctggtg gatttgcttc cgaggcaggc    120
aaggcttgct ttcgtcgcga tccacatgct aatggcctcc ggaaaaggct ggcgtcgctc    180
ccagagcgaa tcataagaca ggcacaggca caggcacctc ctggatggta taatacccct    240
agccttttc ctactttatc ttttttattca ttttttttata taaataact gttgcttttg     300
tttatctttt tagttttcac tagtatttat tatacagtag gacggagtga gtgtattttt    360
aaaacgggt gagtgaacct cgtgacattg accactaccg agagcgggag atgggctggg    420
ccgtgggcgt ggtggcccc accagcggca gcaccggcag ggaagcaca tgcggcgcct     480
gccacaccgc cggccccgc cagcgtggct gctcatcacc gcggcgccca ctctgcacct    540
acgccgtgga agcgcggagc agcacgccag caccgcagcc accaggaca cgagccgcgg    600
aggagaggac ggcgctctgt gcgtgctagt agcatgcagc ggtaccactg tgactgatga    660
```

```
acgaggccca cctggcagcc acgtacggag cgaggggggg cagcattagc attgtgcttg    720
cccgttgttg aaacatggca cgtgcgcaca gtagtggcgg gaaaagggct ctcgccgggc    780
cgcggcgcat gtgatggaga acggactccg tctcccgtgt cagagaggcc gacgttcatg    840
cggagccaaa acagactgcg aagcgaacga ggcgtggcca gtggaatgct tgctttgctt    900
ccctccctgc aactgcaagc catccctcgc catcgccaac gccgaacact gtggatctcg    960
aaacagaaat caagagcggc gcgaggcagc agtacacagt gctgctgctg ctgctgcctg   1020
cctctgcgtc actggctccc gcaatgaatg gaggccgctg cgccgcgctc tgccagtgcc   1080
caccacgcca ccctgcctg aaaaagggcc ctgccgctgc cgctgccgtg cccacgcaaa   1140
accaggcgcg cgcagcagcg gcacgcaggc gcaggcgcac cgtatcccat ctcgttctcg   1200
tctccgccca acggcccacc catcattcag caccccctcc ccttgggcct ttggtttgat   1260
tcgcagggaa aaaaaagaac acacacaaag ctcgatagac ggacggtcac gtggcgcgca   1320
ccctgcctgc cgcctcatgc ttcgccacag ccgtaggatg cggtacgcta ataatccacg   1380
tacgatgcca aaagcttctc gtcaatgacc gtagcggatc aggcacacct gagtgcgtgc   1440
gtacggaacg accaccttga tctcgaactg ccttccgaca agcggccgtc ccgtggtag   1500
tgactgctg cctggctggc tggctggtga caagtggcag ggcgtgcgtg tcgtcacggg   1560
ccgggacggg ggaaagggaa acgaccacag aaccgagatg ccactaccgc tagcacgcac   1620
gcacgtacgt acgtactact actactgcta cttttttcgta cgtgcgaaag tttacactat   1680
tatgtactcg tacaccatgg ctacgacggt acaggtgaca gctactag agctgagcag   1740
cagctagcgc ggcgcgcagc caggaggagg tgctgctgct gcttttgctg tcaccgtcag   1800
tgctgctgag gtgtgcgatg cgtggcactg tacagcgatt cggttttaga gtcgtccggc   1860
ataaaacagg gggcgcgccc aggccagggc acgccggccg tccgcgatcg gcggtcgtgt   1920
cccgtccgca gcaaggggcga ggcgaggcga ggcggccatga gaagtttgcg ttgcgtgccc   1980
gccggatgga tcaccacgct aaccgaatag ggatagaatg gtgtctaata ctgctacggc   2040
cccggatcat ggctcctcac tccccggggt tcaagagaga gcagcagcag cagcagcagc   2100
aggcggagcc gcggaggaaa gaagcattgc agttgcaggc aggccgggtt gcagcacaaa   2160
agctcttcac tgacgaaaac taatgaagca ggaagcatgc aatgcaatgc atgcatgacg   2220
cgcccaaagg tacacaattg ctgcagcaca gcaccagcaa cgccaaaaaa aaaagaggct   2280
cttgtcgtga cgccgagttg ggcccgcacg ggcgggtgtg cggccaccag actagagaga   2340
ggggccgagc ctttgcactt gcagcctttc cacccacgcg gccctcacc aagcgcccgg   2400
ccagaggatc acgttactgt actaggttca tgagaatatg actatagaca agtacgtggg   2460
taacacgaga gctgcccgat gcgggcaacg ggcaacgggc aacggccag gcttttgctc   2520
gcagcctcgc aggttttttt tttaatagtt gcggaggatt tgagaggcgg tgtcctcgat   2580
tctctctatt cccc                                                     2594

SEQ ID NO: 43          moltype = DNA  length = 1814
FEATURE                Location/Qualifiers
source                 1..1814
                       mol_type = genomic DNA
                       organism = Zea mays
SEQUENCE: 43
gtcaactcta taaatcaatt tatagggatg actagaaatc attttccata aatcggggaa     60
aaaaacagta ctacctataa atcataaatc agaccaaaag cagcgtgtct ttaatccgga    120
ttttttgtgc aaattaacta cgcgcgaatg tttcaaggct tgagcgcgtc tcttctaatc    180
attccactct aattctccaa ggtcacttgt gagttgtgac taatatgtag atatacattc    240
cttggagtta gtggttcaaa gcgagcagaa taactacatg catgtttcag ctatgttata    300
tttaccagct accataataa gtagctgcta gctagcctgt ccatgctctt cagacacttt    360
tggaggcaga ctatgacatc actgaccagc tgaagtgttg atgggtggcc acttttcctt    420
tcaacaaagt atcaggtttc cagagttgag ctgaaatgat ggtgaacgac gcggcgaac    480
gtctcctttg cccactttat agataagata tttcttttac cattcaagca ttcatcagga    540
tgagtgacac ttgaactgag cagcaatctg caaaaaaaac atgagttcaa ttggatctct    600
ctctctctct cctatcgaga tggcagctga taaaaaacaa gaaaagcagg aagatacttt    660
tgtagaaata aagtatttcg attgatgaac taaagaccaa gtttaaccaa tctctgcata    720
ttggttggta ggaaaatcga atgatatcaa agcaaaaaat tcagataaga aagtagacag    780
caaatcggta gcttttttg gttagtgttg tcctaatagg cagcatatct gaacctgttt    840
tttcaaaat gccactttac ctgatgcaaa ccgatatgcc tgcctgcttg cttgtgggta    900
tcaaacttgg tcgcaggat gttcctcagt tttcttggcc ctttgacgct ggctaataat    960
agtaccaaca ataatggac cgtatgaatt catcgtccat gttgtggtgg tataggattc   1020
tcaaaattgt ttcagattct gacattttct tgtaatggca aaatgtagca atgtactact   1080
ttacacagct aaggaagtga caatatata tatttttaat ttctttgtct catcctaaaa   1140
tctcctgtct tacaagctct agtgcatata ggcataact actgaaaagc cactacacac   1200
aagaatctgt tccttgtgaa agattgtacc ctactctttc tcatagttgg atgcacacac   1260
caattgcatt tcattagatt ctattaatta gatggtgtac tattaagaac cttcgaccag   1320
tgtatatcat gtactgcatc tattcttcca gaaccaccat gggcagcttc ctgtcaagaa   1380
caccattatt agttactggt aggtgctagc ttcgacattc cacgtgagca gagcaagtag   1440
ttctccatgc tgcatttgtt ccctgccgga gatgctaacg agatcacaag atcaggtgta   1500
atatactgag tataaacgat ttatggttct cagaattttt tcagtgctat ttgaagataa   1560
cgaatggcgt agtctgttg atgtgtcaac agttcatcct atatacaatt cccagttgc   1620
atggacatga taaatgagta ataatgccag ggccataata tgtcatagaa taaactcttt   1680
ttccccttta atgactaaaa gtctatattg tgcacacatt tcattgact gctgattgct   1740
gatcatatat ataaattcgt tgccttttt atttatttag attttctttt atgggaacaa   1800
ctctgtgcat aggc                                                    1814

SEQ ID NO: 44          moltype = DNA  length = 2071
FEATURE                Location/Qualifiers
source                 1..2071
                       mol_type = genomic DNA
                       organism = Zea mays
SEQUENCE: 44
gtctatacat gtcctagttc ttggctccat gcatgcccctt atagttcctg gctcatcata    60
```

```
tactactgat cgatggactc ctggatcgct gaagctgctg cgtgtacgta gttccgtgca    120
gcacgcatgt tacgattacg actttgttag caggtcgttg ttatgcgccg tacgccgcgt    180
ctaagcatat atagtcagcg tcgtcgtccc ccctggcaaa ttatttggtc gttcttctct    240
gacgatgacg aaacacgttc aaaatgcatg cgcgtgttcc gtcgcgcgcg cgttcggtaa    300
acgcgcacgg gaacgacgta cgcgagctcg tgtcccctcg atcattggat ggtctcgtac    360
gtaagtttac tacccgacgt tgcaccgcga aattcaaatg ccagtgccga actaagtttg    420
gctgtcatac atcgtcagaa ggaaaacaga accccccaaaa aaaaacataa tgaggtattc    480
ccatcagagg taagcagctt aggcggctga gttgaatttg actgaataat atccatgctt    540
gtgtgtgcgt gcctaacgca ttgtcgtcgt gttctacgta cgctgctgca tgctactact    600
ttgctactaa aagtcatgca tcgtctcagg tagagctagg ctctaataat gtactagttt    660
atttgaaacg tacgtccggc atacggaaca agtagtaata atgagcatca gatcgcgtgc    720
aatgcagagg atagcagaat atacttgtat gtagctatgt ataggccacg acttgcgtaa    780
agctctaacg gctgttcacg accccaacgt cgtacgagag gccgggaaac aatcgtccag    840
caggccggcg gccggctagc tcggttgccg taagctacga ttcttagcac attaatatta    900
cattacatgc atgcatatcc cgcaccgctg tagcatctat acacagagta ctccacatct    960
acatctcctg gaggtcgatc gacctggcta gtactagtag tacacaggcc gcgggcgcgc   1020
gcgtttggtg cacgtcgtac acaacccect tgaggaataa tcgcatgcct cgacgacgac   1080
gacgtcggag tcagcggcgt ggcaacaatg ttggttagtt gggcaaatta aattgaactc   1140
ccgaagagag acgttgaac tgatgactga gatgagtcgt cgtaaacgtg tgtgccaagg   1200
ttgggcaggg ttgggttggg ttgggccggg cgtacgtata cgtctctgat gcatcgtccc   1260
cctaaggacg gccgacgaca cacatctgtg acagtaactg acaaggactg catcactacg   1320
acgatgcacg cgtcattcgg attgtctgct tcagaataag cgagagctgc gtgccgtacg   1380
tgaccaaatc aaagcacagt cgctaacccc agcccagatg ttctagttga ctaagtgttg   1440
tttacttttt ttccccccctt aagtagatcg agtaacatcg ttatcgcgcg tattgacgga   1500
cagataacca taagctaagt ctatataagt tcggccggtg ctgagctact gcaggtagca   1560
ggatcgatat agcccaagcg atcgagaggg cattaattga ttgtgcttag ttttgtcgtt   1620
tgccgctttg ctctggataa ctacaactac tccagctaga cgtagatcga cctagcgaga   1680
gctgtggact cgagagcgag atttcaactc ctgaacgcgc agtctgtacg tacagctacg   1740
gcctatctaa catgcctttc acttcattcc tcttctggat ttcatctccg caagtcccct   1800
gggatttgct cgttttggtt cagaggattc gctgcttaca cgcacggtcc tggggttaac   1860
ggagctcaac acagtagagt accatctctc attctctctt aatatcatcg gcatgcctta   1920
caactaagag tctgtcgtct tgaggcggtt gatataaaac attcaccatt gttaatagcc   1980
tattactcct gacgacagag gctataccte agtctgtaga gccatggtgt agcctccatc   2040
ttggcatcaa caccgagcac cagtattatt t                                 2071

SEQ ID NO: 45          moltype = DNA  length = 2556
FEATURE                Location/Qualifiers
source                 1..2556
                       mol_type = genomic DNA
                       organism = Zea mays
SEQUENCE: 45
caaattaaat taacgctaac aactgattgt aatcagaata aaacgcacca cacgtaatgc     60
aagtcgacat atgactgaaa tattctagaa tagattccct tttgaacgat tgtcgtgttg    120
ttgcagagtc caccaccaac catatattta ttcagaaatg ctgtcaaatt aagcaatagc    180
acgacgtgtg aacgatcaac atgactatga tgcaaagatc caaggtgcgg tgcgcgcatc    240
ttcctcctca aactggaact cgacacacct gccaactgag atcttattag ttgaactttg    300
agccctgag acgactcatt tggctccaca aggacaatat cgctgctagc ttgttaacaa    360
caagataaga agatcagacc agtgtctgga aagatgcaaa tgttcagtga ctgtgtcgat    420
gaatgatttt ctagatgtga ataataaaac aatttaacct aatcatatca taacaatatt    480
aacaaccgac atgtaggccc agcgccatca tgcatggacc atcggccatg ttgaagtgtt    540
gaagcaattt cattggttaa agtaagctta taggtcaaac acagcaacat ttcaacggtt    600
tgtagtagga ttttttttt ttggcaaagg tgtgtggtgc agaattttg tgccagtacc    660
cttgacgcca ccgcatgcag gtgccatgtg tcggaacgtg gctgcgaaac aaacatacccc    720
caataatccc caaattttca ccaaaatctt tcaataaata cgccttttct tcttactttg    780
ataagagaa tgatccaaat ccaccctcga aattcaacga ttttgccaat ttcacatgta    840
ctctccctcg ttttagtcaa gcaaattatg atacccaacc tgcaattagc tctagcttgc    900
ttgctgtcgg aacatgtcaa agatccgaca aagtatata aaatgttcta tgttgacata    960
gtctatggcc ttcagctgtg ttcttggcta caagcatacg ctcgagagat taattattcc   1020
ctgctttggt ttgtatatag tttcatttct tctagaagcc tttgtttgtt gcatctaaga   1080
cgaagaacca acacgtggcc tctgtagtta tttaggggtga ggcaataaaa aaaaatttat   1140
gcttcgaacc ttcttctgta gcctcccctgc tgcatgccta ttcgtataca aattaacatg   1200
atgccaaagt ctgcataagg ttttccttca aaaagaaaaa aaaaacaagt ccacgtaaga   1260
ttaacagtga cagattggat atattcagac acatttacag gtgtctttgg tttagttgcc   1320
aatgacatga gggtggtgga gaaaacaatc cccgtgatca tactaccaac cctcttttt    1380
cctcacaata attgactttc accgtaccca gtttcggcta aaaataata ttttgaaat    1440
gccagccaaa catcaaacag taaaattcac ccaccaacct aattgtgctt aaacaaatga   1500
cctactaact catagctaga cactacaaaa ggatcatgct gtcgctgttg gcggtatatt   1560
ctccagaagg ggttggacgt ctaagcatct cacatactag accagctagg ctgtaatcac   1620
cgagaggagg aggggtttat ttctttaaac catgcatgcc aagaactgaa gggatgaat   1680
ggaaagtgca tgcatccagt caattaatga ggcacgctac cttatccctg ctacagagat   1740
ttgtttaacc gtctcgatct gtgcaggtta attggtctgc ctctgaatat tcagaatcat   1800
gcaacgacga tgcgtataca gacacacatc atcatgcatg cacaaagaag ctagacagca   1860
ttaaactagt gcaataatga ttccagcata tttttaactgc attattgtgg atccagtacc   1920
gaccttccc aggtgctgct gtggcgagct actatacggt gggtttgaca ctaattaatt   1980
ggatcgagct acgttactcg atcaatacgc atcgtcgtgt ttgtggaggg gttaaataaa   2040
ataaatacgt acggcagtgc catgattggc cgttttatat ataatctctc ccagtcgtaa   2100
catgcacgct ggctggctct acctctacct tgcttgtctg actgaatttt agcatgtgtt   2160
gtggtcaagt agatgatgca agtaattagt agactgtaaa gcttagcata caatgtcgtc   2220
aggtggttag tgtgagagcc tcttacacgc cactgaaagt gccaaacaaa ccttcggaac   2280
```

-continued

```
ctcggcctttt tcgtttggct aaattaaaca aatgtgtggc cttcattaga ttggatcgta  2340
ctacgtgggc gataaaggag acaggtagcg gaaaccaacg acgcctttgg gtaaaaatat  2400
aaacgaactg ccccgaccct tgtttctatc atcgtcttat aagtatatac atgactttgg  2460
ttctttaatt tgggggggtcc aaatcaactg gttgttgcta catctactac taactcgacg  2520
atcaatgcaa tggaattcag tttaaactgg caagcg                            2556

SEQ ID NO: 46           moltype = DNA   length = 1577
FEATURE                 Location/Qualifiers
source                  1..1577
                        mol_type = genomic DNA
                        organism = Zea mays
SEQUENCE: 46
aaggaccaac aacaagccaa aggaactaga tcactgacct cccattgcac tgaggagggc    60
tttgcgaagg gtgctcatgc acatcactct atatctagga atgagtgaaa cacatgaatg   120
tttcaatcaa atgaaaaagg atggagagta ataggatggc aaggagtatt ttttgaaatt   180
tctaggcgtt ttcgaaataa tcataaatgt tggtggttgt gatgccttt atgtaaccgc    240
gtagaagaag agagagagat agctatgctt atgataaaga agatgtgtgt tattgtttgt   300
atatgataat ttttatttac catgtgggta ttgatagtga tgcctacatg atgaatcatt   360
ttgaggagca atgcttgttt tcattattgg ccccaatgtt ttccaagatt ggacattatg   420
gaaggccttg acctcccacc ggtttattag gtaggtctcc tttatcttgc actaagactt   480
ctcatgttca tatccttagg cattggacat atggaccata caaaggtgaa aggaccatca   540
agatcctatt taggtccatt aaatatatat gtagttagaa gtagaagtgg caagtcaaga   600
ggactggtat gtcatacgtc acatgggtgc atgtcacatc ggagtgagct agcgctatca   660
agaagaaaat aaaggtaaat gtagcaatgg gtatattagt ctactatttg tacatgtgat   720
cctgaaagag acattaatat gttggcctag attggacttc ggtcttatag gacatgataa   780
gtaataactg aaactacttt cccgttccgt ttatcttctt tttcttcttc gcttcttcca   840
tctctatccc tatccctatc cctctctctc tcttttaaat tcttccccaa atatacatat   900
atatcccctat tgcatccctg gatcgaaagg gacatgacaa ttcgtatgag atctaggctc   960
ttcatgcagg taattccttt attccctct tggtcttgag tgacaatcat cattaactag   1020
tgttttcatt agacttgcac ttccattcca ggtctgtaat ttgttcattt tggactagag   1080
caattcacca tcacttgtaa ttggtaagca acttattctt tttaatttgc actatcatgg   1140
aggatgtgga agcgtgattg tgcaaattat ttggggacga acactcataa agaattttgg   1200
cggagttgat atgctcaagt aacaaatcat caacatcgac atcaattgta tcgactaggc   1260
catttggatc aaccaagtgc aagcaaagcc ggacttgtca atgtcttttc taggaaattc   1320
tcagcaagaa caacttcatg tcatgcatga tcttaaggag tcccttggtc caagggtagg   1380
acctctagat aaccatggtc cacaattgat gggaccgcct cctcaatttc aacctctacc   1440
atctcattct catatcatgc aggtgaattt acttgcctct tcttaaacaa gtgatttggg   1500
tttttttatt atgcggctgc tgtatgcatt gtgatgcttg ttgggtttac taatgcaagc   1560
tacggtgggc ttgtctt                                                 1577

SEQ ID NO: 47           moltype = DNA   length = 2006
FEATURE                 Location/Qualifiers
source                  1..2006
                        mol_type = genomic DNA
                        organism = Zea mays
SEQUENCE: 47
agagaagtgc acaaacgacc agctctccag ttcctatttg caggaagaat ggtctgaaca    60
gaacctctac aaaacctgca atcaattgaa acagaatcaa gaaccccatcc tttcttccg   120
aaaagacact ttagaacagc aaatgacttt aaaagtttgc caatttgtat cctggacttc   180
caatgtccaa aatatcaata cttccacagc caaacttatt gcagcttata acgacagtta   240
atcacttgaa catctgatag accactgatc tcaataaagt tgttcatcga tacagtgatt   300
tttttgtaag ttgtcaaaag aactcaggtt atagcatttt ccagacaaaa ttctagccat   360
actcgtaagg ggagggggga gggggatcag ccagttggaa ttgatctttc ttcaaacctc   420
aacaggcaga aaactaccaa gtgaatgttt agattttaaa ttacacagat cgaagggagc   480
aatctgaaaa ttgcatggcc aagtagtgta tgatgaagtt ctgtcctaga aggtttctgt   540
gttcgcagag aggaatgggc aaatggctag aactctaagc tacatttaa aagatataaa   600
gttctcagta ttcacacata cattttcaa cagaaactgt ggataaatgc tagagtaaaa   660
tagtatgacc aaatcgtgat ccaaaaaaca gaagttccaa cgaggcatac attttgcaac   720
catcagaagt atatacttcc ttcagattcc gtatcctctg atcaaatgca acagactttc   780
ccgtttcatc atctcgaact aggaccttgtc tctctgcatg gccctgaaat agtgattttt   840
tagcaacatg gtcaagaact aatattaaaa cagaagcatc tgaaccaaaa gaaaggaaca   900
gttattggca tctataaata aagaaattag cgaagtgaac cttgcgcatt acctgatcca   960
ctaacacatt aatatagta ggaattttcg aatgaataac tgaaagtact gttgggtgtg   1020
gcgttgacgg aagcaaatga tctgaatgt caacctatt caaagatgga ataagaattc   1080
agacaaccaa atatgaacaa aatagaagac cttattgtct taccgtggtt tagtgaagtc   1140
atatataata atttgaaggt tgcgatagtt cacttcttc gcacattctc gtaaaacgag   1200
tgaatcctta tgacatgaga caatgaaagc atctaataac ctcccctaatg catattcaat   1260
tgcaacagac caggaatcgc ttgccagttg ctgcatcaaa gcaaataacg caatgagtgg   1320
aacctggagt gaacaagtaa agtaatcaaa agaaatacga caacaatcaa ggatagttat   1380
gccataccag atgatatcct attggaccaa taggagggca tttgaattta ctcatgtgtc   1440
tctctactga tttatagagg ctcggaactc tatctcctcc gaaggccgtt agctgtaaag   1500
gagcatcact agttgctaca attagtttat acaaccaaat agttgttact taaaatgtct   1560
gaaaacacag cattaatata gtagaaatat ttcatgctta atgaagcatt ggatagtact   1620
ttgttttgtt ggcgccgtcg tatatcatca atttgacttc tcagttgatt gatcctacgt   1680
ccatcttctt ctatctgcaa agtacataca acagaatata cagtacaaca ccacaaggat   1740
ccaaaacaaa ggttaacacc ataaacatgg cagcgcggac aaaattacat gttgtgcaga   1800
taattgtgac tactcgaatt attcccctat gctgaagcca tgtcgctaac cagggaggag   1860
tatactactg ggttttggtc agggctaggg gcatctcatt ttttccttgcc cttgggcctc   1920
agcagtcagt agaggtcctc ttttcccctt ggttaggtca aggttgttcg atgttttcaa   1980
```

```
gggcgcgtgt gtaaccaaac acccta                                          2006

SEQ ID NO: 48           moltype = DNA   length = 1795
FEATURE                 Location/Qualifiers
source                  1..1795
                        mol_type = genomic DNA
                        organism = Zea mays
SEQUENCE: 48
ttgtatatat ataaaaaagg aggctttgtg gctgacaccg ccatccccca aataaaatag      60
gcattcgcag ctggctgaag agaggggatg tcgcattaaa aaaaagatga aaatacctct     120
ggctaaaaaa tgagtgtcgg tgtatatata atactaaaca aaaccagatt tttttttacaa    180
tagacttaaa tcaaagaacg tggtgtggga cagacaaaat cactacgtac gactacagag    240
tgtgccatag acaaatggct caaaaaaaaa caaaaaaaaa agaaacaaaa aagaacgagc    300
gttgcgctgt gcaacacccg ttccgcttca atgccctgcc gtccttggct cctccttccg    360
cctgttctgt tctgctctgc tctgtttctc tctccctctc cctcaggcac tgtagcaggg    420
gcgtgtgggg cgagtccctg tgcgcgcgcc tacgacgaac gagaggacac tgccacttcg    480
aactgggaat taaatttgca tggggccttt tggcccgtgc agatgggagg ttggggttgc    540
cgttgccttg gtggaccacc accacgcccc ccgtgcactg tgcgccattc atcaccatat    600
gacctacagt acgtaggagt agggctttac tttgtcatcg caaatccagg ctgcactgca    660
ctcgacgatc atctgctggc ggtttagcaa ctaacgacgt acgggcgaca tcctttgatc    720
aggccgcctt tgtgtagcaa gcacagattt attaattacg tacgtatacg caacagcccg    780
acagatgaca ctgcttctta ctaattattt gatgcacaca tggtgtacca tgcgaaacgg    840
gaaaaaaagg ctgatagatg ccaacgagtt acggacgagt acgtacaatg ttgttgttac    900
acaagctatt cggctctagg taacaaacta gtacagcgag cagaacatcg cattaaggat    960
ggcagtaaaa accaagcgca caactttcat ttcgtctctt atttattcat cgcagtatta   1020
gtagtgtact actgaactag ctagtgttct tcgtaattaa tattttattt gacaatttaa   1080
tcttagatca gctgtgtgtg catcaagaca cggggaccac gccgaaacag ttccggtcg    1140
agaagcccct gtcgccatgc catgcaacgg tcgtgcgtgc gagaggcgaa tcagtggacg   1200
acggccgtag tgtcagcaag agtgagcaag cccctggcgc cggcgtagcc agcggcgcag   1260
gctaaagccg caggggcaggg acgagcgac tagtacgtac tagcaacgaa gcgagcgaac   1320
gcgcgcccca aagtgcaaag cggccaggcc aggcatggtg cgttgggtac gcagggtgta   1380
attgcgagtg ctactccgcc taggactact ctactctact actactcgtc acggctgtac   1440
tagcagtaca ctgtagcaca cctggattac gggctaccca gggctggaca gggggcaggc   1500
agctgtatac taggtgttta acggaacgga aaccgagcga tgattgcctt gattgggttc   1560
ggggggcttt gaccacctgc cacttttctg acttctgtct ctctctctcc cccatagagg   1620
aaccgaggag ggagagaggg acgcgtttgt gtcgcccgcg gcccagtagc ccgttggacg   1680
gatgggctgg tttgggaggg ctgacaccga cgttacgtaa gtccaattgt ctggacctgg   1740
ggcctggggtt aggtttcgac gacaagatta ttcagctttt gttttgttaa gtatc        1795

SEQ ID NO: 49           moltype = DNA   length = 3690
FEATURE                 Location/Qualifiers
source                  1..3690
                        mol_type = genomic DNA
                        organism = Zea mays
SEQUENCE: 49
ggagtagttc ttgatattgt attgtgatgg tgttaaagct atatacaatc atgaagggtg      60
taattattgt gaagacattc actttgacgc tggaaggggtg tgaaaaaaca tgagcttttta   120
tacgtccttc tttctcgcgt cttttaatgg aaaaagattca gactgtagat ctatgcgacg   180
atccgatgat gccgttactc caccacgcac agcagtcggc agagcagagg caggcagtat   240
tgcagcccag cacacacgca ccgctcgttg cgcaggcgtg tggcgtccaa tcaccccgt    300
agtagtgggc cgtaacactc tccgccacag gacaggctca ttaacccggg tcacactgcg   360
cttgcacagc acgggcacgg gcacgggaca gcgcgcggct cgcatcgcat cgcgtcaatc   420
gtttcgacgg gccgggcggg cgacgcccac acgccacgcc cacgccaacg agagccggca   480
gcgtgcgtgc tgtcagccgc gataactctc cattaactaa cccatgcgat ggccagctcg   540
cggctccggt gtcaacctga caaaacccgt ggcccggtcg gcggcccgcc ccgcccccg    600
ccccatcgt ccgtcggttt tggtcgggcg accgagccgt gcccggtatg ggagtaggcc    660
cggccgaggc tgcgtgcgag acaagggcgc gctcggcctc cggcctctgg ctccggctgc    720
gcgacctgac gcggataggc agccaaaggc gtgcgtagcc gcgtagggct gtttggattt    780
ttcatggtag tagcttgtct gtctgaggta gccaggggtg tagatggaag atggtccgtc    840
cgatccacaa gggatgatga tgatgacgaa ttgatgagct caaatgtcta gctacctacc    900
tacctaccta gctagccggg tctgctggag cctgcacatt gcatgcaggg tcgaggggaa    960
ccgtgccgcc gcacgtaccg ggtgtacatt gttgaccaaa acatgggctg cctgcctgcc   1020
tgccacgtac tatcgtgagc ttagcgaaac ttgttcctcg aatcaatgcc agtgcctgtg   1080
cctgcactgc gactgcgagg gagcgagcga gcagcagtac cccctcgtc acagtacgtg   1140
tcgtatgcc gtatgcgtgc tagtgctaaa aaaacactgg cagcgcatat aactactgca   1200
ctgtaacttc tttcgtctgg aatagttagg tacctactgt gcacagaatc tgcatctgca   1260
tgcgcgcgtc cttgtttttt gatgggtaag tataaagcat tggtacactg gaaacactaa   1320
tcaatcgatg agcaccggtc cagtgatgac atcttgaatt ttttttcctc cctccaaaag   1380
gacggataac tcctgctcgt ttactgtacg tagatgctgt agatacaatg gaatcgtaga   1440
gcatttgatc agacagacgg tcctccacac gcgccgccgc ggttttgagt tgactcctgc   1500
ccccccccggc agaagccacg aggcccatcc acgccacggc catcgagtcc cgccggcatt   1560
ggcagttgga tcgatggcac ggcgtcccac tcgctcccac tcattcatcc agtgtcagcg   1620
tgcgtgcccc catccggcca acaccaacaa acaacccaag gcaaacaaaa ccaccctcca   1680
cccccag ctctgaacct ctcccatcca tccgccgacg agggacaaag ccccaccacc     1740
gagccagaca gccccacggg cgggcaggct gcgggcgcta ggcgatatat atcccactgc   1800
gcacccgcac agcctgcctg ccccccgcgcg cgcaacaaca tccgccgtgc ccaggagacg   1860
ccgaggcacc gctccggcgc tccgcctccg ctccgcaagt ccgcagtccc cacaccacac   1920
gtggtagggg cgccacaaca actgctccgc tggctcgcct cctcctcctc gtgcgcccgt   1980
tctgccactg ccaggccggc gcccgccagg gacaggacag catgtggtca gtgtacagaa   2040
```

```
ttcacttctc cgtgccttct cctctcctcc ggggctacct gggcactgga ccagaacatt   2100
ctgaagccca gcctgtcctg gcccaggcct ccaacggaac cggacccgga gcggcctact   2160
tggcctagcg ttaatttgtt ttttttttgtt tgggctccgg taaatcggat aagaaaaatt   2220
accatcctgg atttaaaaaa aatactatcc ctgatttcgg atactcggta attaaaattt   2280
tactactgta gttcgatgta ccccgagttc gcataaaccg aaacttgcat ggaattgcag   2340
cagtaattta tgtcatgaa tttatgtgcg ctaccaggtc atgaagttcc tctcctgtgc    2400
aaaaggaagc aaaccgtacg tacgtacgtg tgtggcgcgt ggcaccgcta cgctagcgc    2460
tagccctgtc cggcgtcaca tgatgcaaac gaagtggccg taactacact acagacccct   2520
cgatcggcac tgttctttcc atccccacct ccgcgtgcca cgccgcactt ggcaaaacgg   2580
aatgctgccc tgccggctgc cggtacctgt atttactacc gccaccattc caccaacaca   2640
ggccacagca cagcacagca gcatggcgcg tcgctgtgca ctgtaccgct acgccccct    2700
gcggcctgcg tacaccacca tcgagggcat gccacgccga aagcggtgc tctgctagta    2760
aggaacgggc atctgatccg acggccgggc ggggcggtgt gcccggtacc cgtgtcgccg   2820
catgcacgta gagcgcttgc gcttccttcc aaccagcaac caccgccaca tcagggagta   2880
aatgccatc  acccgcgctc tcacctcttt cacggtcgcg gaccggaggc ctacccgtat    2940
cggcgtacta gtgcgtctca caaaggtgtc cgggcgcgcc cgcaggccta gagcgagggc   3000
ctcgtaacgc tgccccgaaa ccgaaacgtg ggcgtgtatc cctccagtcc agcgggattg   3060
catcacctgc gccggcgccg cgccatgcat ggcatggcag caccagctgc tgctgcccgc   3120
catgcatgca tggttgattg gcagcttgtt ttgttcgtgc ggtcgtgcct gtgtgtgctg   3180
atgtcgtcgt ctacgcaata cagtacgacg gagctagcta agctaccagt agactagagt   3240
actccgctcc gctgcacatt gacgattttt gattttggat cgaatattcg aatggcattg   3300
gcatggtgtc gagtacgtag tgtacgtagt acttcttttc ttgaggatag gctgctctgg   3360
ctctctcccg aataagctcg tgtatggatg gcagcagggc accccatcg atcacctgcg    3420
gtgcggaggt acgggcgggg ctgacttttt ccgcagaacg aaccggcacc aagatttatt    3480
acagaattta cagcaagtca acactttcac tgtgatcgca ctgtccgtga attaacgcgg   3540
cagctgtacg agcgttcctt tccgtttccg tttccgtttc ggctgcacgc ggcactgtga   3600
catgcgtatt caaggtctgc tagctgtcgt cgtcccttc cgtttcaaat tgcaaatcta    3660
gtctatatat acaagtcaga cggaatatat                                    3690

SEQ ID NO: 50          moltype = DNA  length = 1742
FEATURE                Location/Qualifiers
source                 1..1742
                       mol_type = genomic DNA
                       organism = Zea mays
SEQUENCE: 50
ccgaactgag agagtaatta atagcatcac agtgtaatat acgagtataa atgaaaactg     60
cgcgtgggca gatctaatca tctaatacgc ttaggcagaa ggtggttaaa cagaagcatg    120
atgtgcatgt taccgaccct gctgcgcaga atgggccttc gagatttaag gaaatccccc    180
atgtaatcaa tccatcatca aactgaggat tttggagcct tgtgaaacca gcatctaccc    240
aacagcaagg aagcaagcag gctagctagg gagtagcagt agctagcagt agcccttctg    300
gttgctggtg cagcatcagc gtccacagta gtccaggttg ggtctggcaa catggcatta    360
tatgtcggcc gtgaaacatt cttggggtgt taatgtgtta tatcccaggc acaagcacaa    420
cacacgaacg aggttgccgc gtactacgta caacctggca aatggcttgc cgttgtggac    480
acgcgtagta ataacgcgga gcaagctctt gtaatggaca gctgtaaact gtaatggaac    540
tgttcaaatt gcactacaaa tggaacccgg ccgaggtcgt ccaggcagga tgcctggaac    600
agatagatac atgcagagta cgtaagtgag tactaaacaa atctgaacaa aggaaagctt    660
tcctgaaagt cgccaggcgc aggcgaagta ctgatgaatg cgaacacgc aagtgcttgc     720
tcccacagac ccacactccc agctgatcgg cagccatcag ctcagaggct caggcgttcc    780
ctaaaaaaaa tctgccaact atatgggaat ccaaggcctc gctgcattgg agagcatgga    840
tctcatctgt gacaccgaca ccgaccgact ggcagccgcg cgctggtgtt ttgatgtcga    900
acgcgcaag gccggtgcat ttgctcgcgt cgtcgtatcg tacgccccg gcggggcgat      960
acgcccatac ctgccgcgca ttaaaaatcc tccacgtacg tggtcggccg acgggccatg   1020
cgcctgccac tccacgccgc ggcacggcgt ggcactggca atgttagcac gacaagggcg   1080
ccactccgcg ctggcacacg cgacgtgctg gcgccggcc cgcggcgcgc tgccgcacgc    1140
ggcttcacgt tgcttggtct gccgctgctg gcgctcgctc gacgacaccg gggcggcggg   1200
cgggcggcac ggcaggactc cggcaccct ctggctctac tatccgttcg gctttatcca    1260
cctgcgacgg ccctacgttc gtctacgtgc cgtggagagc acaggggcgcc acggcgccgt  1320
gtttcttcgg tgcttgtctg gccgtttggg caacggtggt tccttaaaat gcagatccgc   1380
tcgctgaaga gtgaagaccg accgactcgg ggatgcgtga gagagaaaat ggtgatgagg   1440
ccaagatcga gtcaatatac acgacaagat ggaaggtacg attggatccc gcccgtcgaa   1500
actcaagcca gactacattg atagctagct gatgcctgac gtgtattttg gttgcagtga   1560
caggatgagg ccgatttagg attttgtttt agcgtaggta tgccatagta attaataatt   1620
tatccaccaa aatctggtat actctttgat atattataac tcggtgtagt ctatataatg   1680
tggtaagcaa ttttaaaaca ggtcaaaaca ggtaaaaatt atagatcaag tagcattcat   1740
ag                                                                 1742

SEQ ID NO: 51          moltype = DNA  length = 1636
FEATURE                Location/Qualifiers
source                 1..1636
                       mol_type = genomic DNA
                       organism = Zea mays
SEQUENCE: 51
tgggaatgag ggctaaagct agctaataga agaaacaaaa aacgtgttat ccaaaggctt     60
cagtaacaag tctcgtgata tccaaagtaa tggatatcga tcgtgctctc gttgcacgat    120
tgtgcaattc caactctgac catgaatcag aattcagaaa gctcggaact gaaacccgac    180
ggacgaattc tcggtgtttt cgtataatcc gtgcaagaat ctgactggtt gagcagtgca    240
ggtcctgcac gatgtggtgc cctagcttcg cgtgccagaa aagcaggacc agcccgccgc    300
cccagtcacc gggcggggccc accctcgacc gcagccgcgc tttcaactgt tcaagtaccg    360
acccaaccgt cgccggtacg tcgtccgtcc aggctaccca gtagccctca tcggcggggcg  420
```

```
gcggccagca ccaccgccac ggcccccaga cccgaacgtc gccattcaat gcggcgcacc    480
tacaatttcg caacgaccgg ccgggtacgt acgcgacccc gcaggcccct gcagtggtgc    540
cgctctgcag ccctcgttgg ctgtctgccg gtcgccgtcg tcgggagcgc ttgggatggt    600
gggggggcca aaccggcggg gtagccgccc aggctaggtc gaccagagcc ggcccatgtg    660
gcccttcgct tggtcgggca gcaacgctac gctgtgtggc ctgtggctgc ctgtctgccg    720
tccccggctt gggttgcacc gagcagcaga gctgcagcag agacgtgacg tcgagcctgc    780
aatttgcgca tcaggacaca gccaccggct gggcacgtga acgcaacgca cagctcaacc    840
gagagggtcg tggcgatcac gtgactgctg cacccaaatt ggctgcggcg tgttgtgttt    900
aagcttccag ctggatctga aatcgatgtg aatgatttgc cgcgaactgt aatgaaccgt    960
atttaactct tgtgtagctc gcgggggatga tgggttgcag cacaggtgtt gggccgaaat   1020
cctatgcccc atcgctggtg aaacagggac tgctcactgg cttccacaca cacacacaca   1080
gaggaatgtt cggtgcgaat tgtgatcctg gacctgaggg gagggagagg gggtgcaaat   1140
atcctgactc ctgagagcgt aataaatttt ggtcagatca acgacgttct tcagaaacgt   1200
aggtgcatca tggcgaaaga aaaatgctgg cgcgacgttc atggcaggta gacacgacac   1260
acaaaggatt actctatctt gtgaaagatc tcttgtatac tgtcatcaca tttactgctg   1320
tagatagagc tatgtgtaat ggatgttcag acaggcgtga aggactctgc aacttccttt   1380
gtcattggct cgttgattct tctcaataat ggaattgaga tccctgggcc ctggggtggt   1440
aagacaacgt gataatggag tgcatgtatc ctagcctcct agtagggaga tcgagaccgg   1500
aataaagact attattcctc tgaatagctg tacagctata tacgtataat ctgcaaagct   1560
atatcttaat cttgttctga tggcctacat tgcgtcatta tctgctttgc tttggtcttc   1620
ccctcccctc aatgca                                                   1636

SEQ ID NO: 52          moltype = DNA  length = 2937
FEATURE                Location/Qualifiers
source                 1..2937
                       mol_type = genomic DNA
                       organism = Zea mays
SEQUENCE: 52
cagagccgag cacatcgtag tagataaaag gaaggaacac gcggtccttt ttctagaagt     60
ttcggaaccc aattgcacga gtcagcagct catgttaatg ttagcttttt tttccaagcc    120
gaaccgagag cttgcaagcc gccagccaca ccaagtcgaa gtggagtttc agcccacttt    180
cgtcgggaac ggaggccgcg gcccaatgga tccgacaggg tgatctgagc tcctgtcggc    240
gggccgctgg gagcagagtt cctttgcgac aagcccacaa ggaactcagg tccggagtct    300
gaaacagtgg cccaacgaac cggattttcc gtagcgtaga caactgttcc acggaaacgt    360
aggcgtggac ctccgtgggc tggtggtagc cgacacgagg aatagtagga cacctgcgtg    420
actgaagagg aacagccacg gttggtggtg ttcgagtttg cgtcattctg aagcctgaac    480
agctagcatc ggctttgact gctctcgcaa cagcaagtca gcgacccagc ttattaccta    540
cgtctacatg ccaattgaca tgacttctca tggctaccct ttttatgact gcgccttaag    600
actagtaaaa ctcacgaaag ggggagactg tgaaacgatc cagttcggcc cgtccccgac    660
cgctcccgct cccgctcctg catgtggtgc caaaagggtc aatggagcta gctagatact    720
cgtgagaact gattatgtct cctaatcatt taatcaatca tgagattgtt tatgctcgtg    780
gttatgatta ggccaagaga cgaagacaag cggcgcacac tcaagtgatg cccccccagag   840
ccttcttgcc atgcactact actactacgg cgccaccgaa caggctgtcc ccgctttgca    900
cgtccaggaa atcaaaactc cggtatagaa gtagaaggac ggcagctgca gcgcatgtaa    960
tggccgacca gggcggcagt agaaaaaaaa aggtcgagga attcggttcc tttcctccag   1020
gcagcccttg ggctagcatc gttggcaact cgctatcctg ctctaggacc tcagtcagtg   1080
caaatcttcc actagccatt tgttaatggc gaccagcgct agtagctagc tagctatcta   1140
ctcgacacag tgagcgtcgc ccgagcgaga actcaacgcg ccgaggcacc aggggcccgg   1200
ggtcctgttc ctgtagccta gtccacacaa gctgcaggtg cgtgacacgc acaaaccacg   1260
ccacgcttaa ttaaccacgt cattccacga tctgttcgtt tggcgcaatg attgtctcag   1320
caacgaaaca aacaagggtt cggctcatca tcagggggag taatgcatgg aggcgaccac   1380
ctaacgagag gtcttaccct tgaccacacc ggccggccgg acggggcct gatcctggct    1440
aaaacgtgct aacaacggtt ctcataccaa ctgttggtcg tgtggatgta cataaccaac   1500
tgttgcagca cacgtgcagc aaggatttct agacacgtct atatagtacg aaaggagaca   1560
cgtatggacg aagcagtttt ataagaagag aagaaaaaaa aacccaagcg attctgccat   1620
cataattgtg ccgctgcagt cgcgccttaa tagaatacgc taatggagac gaaaagcctg   1680
gttgttgtag gttgagatgt caggacgcgg ctatagaggg agctgaggag aactttagta   1740
cagttcggtt tcttggttcc taatgaacaa tgatatgcat gcatgcgtag ctaataaggg   1800
gggtgcccca gctgcccttg aattcaggct gggggcggg ctccacggcg tctgcatacc    1860
acaaccgaca ggaacgggat aatattatta ttctctccac cggactcatt agcgtttatt   1920
aggaaccaaa cgtcccctca caagacaaca aaagtagtcg agtagatggc gcttatatta   1980
actttaagat aaccctacat acgttagggt ttttgttttt cttcctttt ttaacaaata    2040
aagtacacat tttatttgca ctggttagca ggaactgccc cctttcacac gctcttgatt   2100
tcaggacaat tttttgaggc attacgtacc gatgtaatat atcaacacga gatacatagt   2160
aataactaat ttttagtttt accattatac aaatataatc atcatattcg aacatgttat   2220
gccctcacct taagagctaa caaaaccctc ggtgttaatc ccaatagcca attgtaatcg   2280
gttgcaccgt cgggaacata aaaaccacat cggccgccaa tcataaaacc ttgccaacga   2340
attgtcgaca actcactaga accctaggca acaaaaaaaa atgcagttct agtagtatga   2400
acagattgta gataggccat cttcgtgctg gagcttcttt cccccctgaa taattaagat   2460
ttatctcatg atatattcgc agcttaatac atgtatcatg tatgtacact gttgcttgtc   2520
gtctggtgga ctggtgggcc tatagactat agtataagca ggcactctgg catggcagcc   2580
aaaatcagag agacagtagt ctcacaacat agtcccgaat catttaatta ccagggggac   2640
ccaacaatct gcgagcagga gtgtcgtatt gccacaaaca aagtgctcgt ggcgtcgtat   2700
aaaagaaaaa taggggacaa aatttcatta ttcggaactt tctctcgcac actatggcag   2760
aataaagcga acactactac agatcctacg accactggat cagcaaccgg caaagggagt   2820
actactgtat gtcaaagtgc aagctccagt ctatatctag ttgttgcgag tagcaaattt   2880
tgcaaccgca ctcaagggac agagagcggg ccatatttct gaaacataaa tatgacg      2937

SEQ ID NO: 53          moltype = DNA  length = 1941
```

```
FEATURE                 Location/Qualifiers
source                  1..1941
                        mol_type = genomic DNA
                        organism = Zea mays
SEQUENCE: 53
gaaggaaaaa aaaacatgcc atgcaacatg catgcatgcg tgtatgtgtg tgtgttgcac    60
tgcacgcgct gcctgtgtgt aggcaccttt gccttcgctg gcaataaaaa agcatacgga   120
aacagtactg ttaactagta gatctggaga gatcgagtgg gtggactgga cgagctgtgg   180
catctgcatt tggcgtacct atactataca gatccaatcc acggggggaaa aaggtataga   240
tcaggagaga acgcactggg ctgggctcga aacgaagtgg ccaagaattg tccttatttg   300
cagcggcggt gaaaatgaaa tcctcttgga tcttttgatc gggagaaaag cgggcctgca   360
tctgcatgcg tgacgcaccc agccacgtga cagaggatgc ctgatccgac ggtcgtatct   420
gtccgcggca tctttgcgca aaaaaaaaaa aaaatcatgg agggcagata cgccggtgt    480
gccagccagc cagccagcct tgggggaggg gggccgtcag gatcaggact caggatttgg   540
accacggcaa agggcctggg accctcgccc ttgttcaatc atttgcacga gcgaatgctg   600
cgctgcgccc tgcaggattc atccgactgg aggccgaggg tgcatgcacg tcagtcgcat   660
tgcacggcca tggacacgta caacgcaagc ttgtgactct gtgactggga gcggtgagca   720
tgtgagggtg ttagactgga ggaggactcg agtgacgacg aatcgttgca gactgctggc   780
ttagttgcca ctgtgtgtga ctgtggtaag tacagcagga catgtggcat tggcatgcat   840
ggcggtgaat taagaccagc gtagtaatca tgcatgcatg gccagttcat ctcgtctcgc   900
tcgcgttact gcagagtctc gctgtagtat atctgtactg tacccgggcc gggcggacgg   960
acacacagca cacacagaca tccatcaatg ccgttgtact actacacaca cagctacgca  1020
ctcagtgcat gcatggagag actggagagt atagtagtac tctacataca cacacacgac  1080
acgagggtac atcaacagct catcgccttc atcaggtcag tcattcgccg agtcaccagc  1140
agcctggccg ccctttttgct tctgcactgc cacaggagta gtactactgt actagctagc  1200
aaggccatcg atcgctagct gtacgcgctt gcgccttttct ttgtggctgg ctccgtcgt   1260
tttccccccct tttccgagaa acgggtcggg cgggttcggg caggcggaca cgacggacat  1320
cctgtccacg agaagaattt ctggacgggg ttttttttttct ctctctctct ctctcccaaa 1380
ctcagccgca aaagtttctc aggtccacgg cgggcgccga ggcagacgct ttcagtcgt   1440
tcagattcag atagatgaac gcccgcggta ccggcttcca gacaaacatg cctttttttt  1500
tttgaacgag tatgatgagg agaaaacaag gcggaattgt tccaggaaag acggatgcgt  1560
cttgactgcg tttcggtgaa atttgaaaaa ggtcgcgaaa aaagtgatc cttcagggtg   1620
ggcccgccgg agcacggcag atggacgaaa tccacacatg acgctgtgtt gtttgactac  1680
catgtactag tagtgtttag ttataatgca ctctccctga gccctgactt accacgtcac  1740
tttaaaaaat gctcagacat atataaacgc gatgcattta actttctact cctggtttga  1800
atggaaagac agacaaagat aatagtataa tactagcaca ccacatagat cagggtcaga  1860
gaggaataat tacgcgcgct cgcgcggtct gggcaacgtc tgcgtgcctc gagtttgatt  1920
tgaccaaaaa aaaaaaagaa a                                            1941

SEQ ID NO: 54           moltype = DNA   length = 1560
FEATURE                 Location/Qualifiers
source                  1..1560
                        mol_type = genomic DNA
                        organism = Zea mays
SEQUENCE: 54
tagtactact gtctactcct acgtacgtac gtacgaccgg ccgttttgc acgctctgga    60
actggtagtt cgctagctag tacgtgcgga gagccggaga cgaagcgacg gatccgttga   120
tcgagcgcgt cggtcccgat ggcgacagga gcgcactagt acgtgctagt cgcgcgcgtt   180
gtttcggcac atcttccatc gatcgcccgg ccggccgttg acgacacgcg cgcactgcac   240
atacgtacca cagcgtcgtc gcgcagccgt ccgtttctg caaccagcta tagctgccta   300
gctacctagc tagtctacca gcagacagac gccaacctga cccttgactt gcgcgttgtt   360
tgcgcgcgcg cggggccggg cacacgctct cgcgtacgta cccgtccact tcctcacgtg   420
agaataaacg gcttggcctt agcttggcgt ggcccggagg agtcgttatt attattgcca   480
catgcagctc tggagacgag acagcatctg ccgtgtgtct tcgcgcggaa ggaaagaatc   540
cagagcgtgg ccgcgccgcg caggcagtag gcgacgaagc gtacggaggc cgcggccgaa   600
agcgagaggt cgggtcgggt cgtcgccgcg gaccgacgac gagctagcga ggttgccccc   660
gtgacgcgtc ggcaataacg cccgcgcgcg cgcgtatata tatatatatg cccagatcga   720
cacacgctc gtcgaaataa ttagccggca ggcgtttgtg ggcgcggtgc gcgcgtacgt    780
gcacacgcat gaggtcgagg gccgaccgat cgccccggcg gcgactgacg acccatcgtc   840
gcgccgtgga cgattcgaat ttgggggatcc ggacgccgcc atgggtcgat ctgcatgccg   900
gtcaaatgaa aaccgtgtgg atgggagatgg gggatgggga tgggttgctc cgatccggcg   960
tcgctagcta gctactacct gtgctagcta gtggtggcgt ccacgcgcc acccacctcc   1020
actcaggcgt attcgttgct agtacaagta cgagaaccac ttgctacgac tcgtcgtcct  1080
gctaggtgct agctcgtcca tgcatgctag ctagacgcca ctgggtgcat gagtgggtgg  1140
cgtggcatgc aggaaatatg agctagctag agagcgaaat taggacgacg ggttaattag  1200
agagatagca gctgctatct atatagttag tagcctatta ttactagggc taggacgagc  1260
tgatgaggga ccgacaggga gagagattct ctttgtttgc tgctaacccc gtgctcctgc  1320
tcgtgaagga aaggacggcc gatcagggga gaaagagaga gagagagaga aagctgtatg  1380
tatgcggtgt aggattatta cagtttagct tctctctctt gcaagtaga gtaaacaaac   1440
aaatcaatcc actagatggg acgactggac gagaaagggga gagagagagg aacaattcaa  1500
gggccgccgg agtgcgtgac tgactgatta tatatcggaa atggacgacc gaccggatgg  1560

SEQ ID NO: 55           moltype = DNA   length = 2113
FEATURE                 Location/Qualifiers
source                  1..2113
                        mol_type = genomic DNA
                        organism = Zea mays
SEQUENCE: 55
acggtcatgg gggcacgtga aagcgtacgc gtgcgcggcg ggcgcagcgt gcgcacgttg    60
```

```
gaccgagcgc ggaacggaag gcccgaaccc gaagcggcca aacccgcgc ggaaaacgta    120
cgagcggga aggaggcgtg ggcgcccatg ctgctggggc cgccgttagc ctcgccggcg    180
cgcgatcgta ccgcgcggcg gcggcttttt tccatgggcg gtgccgcccc gccggcgggc   240
cctccgtccc tatagtcccg tcgcaagcgg ccgctggttt ggttggtcgc ttcgctcggc   300
aggaagcgag cactgttgac gggttggcgc ggcgcggggg gctcgctttt cttgccgtcg   360
actcgtggct ggctgcacca cctgactggc ggcgggccca ccgaggcggg gaagtgggag   420
gagacaggcc ggatccgcga ccgcgaccgg ggcgggagg gcccccacc ccacgtctgt    480
ctgctctggg aagtgaaacc aaaccagcag acgaggacga gacaagccag cagccagctc   540
ccgtgttgct gccgccggcc gctctctgcc cgcagcccgc agcccacaga caggagggc    600
gtgggggcc cgggccggag agagccacct cgccgactcgc gccgtcgccg ctcgcaacga   660
cttaactgc cacatttatg gccctgctat aaaacaaact gccgcattta ataggctacc   720
ggccaggcct gagagagatt cgggcagaat ggggaatgca gatgcatcag tggtgcagca   780
gtgctacagt accagcgtat tgcattgcat cgccggaacg cgacgcaagat tccttcgtcg  840
tgaccgctcc aaaacgaccc ttgccttggc ttgcactgtc aggtggaagc attgttcact   900
gtcggataca tacatgagat catgtgtgcg acagactgta cagcaaacag ctagctcaca   960
tcacaaaaca tgtggccggg gcgcacacag actaataagc tctcgttaat ttagtgtacg  1020
ccgaccgcgc gcgtcggtct cactttgctg ctttgcatca gatcaggtag gtaggtaggt  1080
tatatatgtc attttgttaa gaaccatttg ctaattaaca acctgcgccg ttttggcgcc  1140
aaagtttttca gacagagtta ggtcaaacca atcctctctt ctattttatt catcaacgcg  1200
tattaacaca accaaccacg tatagaacga ctcctaaaaa gaggctcttt cttctgcagt   1260
tgtttttttt ttctcataat gtatgagctt cgaaaagttc agcaattgct tgctgcactt   1320
ggattacaca tgttcattgg tcgagtacgt gtcgtttcag ctggatttga tgctgcgatg   1380
tagtaaccag ctatagtgca cgcgtgggc cttttttatca ccccaaacc caccttttaag   1440
gaaatcgtaa aggagatacg tacatctcta tctagcttca acgaaggtg cgtgccaaaa    1500
acaatggcag atgactagat tttgtgattg gatgatatgg aaagcaatta ttaatcatct   1560
tttgatatct cgccggtcgga ttcatttgat tgatagagag ccggcgttcc acttttcata  1620
tttttgcccc tactagcaga cagtggctct gtaacttcca atatggatt gtgggactga   1680
agggttaatt attatctgta ttctgtataa tcggtggctg tatgtacgat ataatcattt   1740
tgaaacataa cggtacatta tttctcattc ctgtccaaga agcttaagtc atgtatggat   1800
ctaactaaca acaggctaac taacttctta gtctatgatg atccaaatat acaaactaaa   1860
atatgagtcc gctagttaat aggactagta gttgttagtt tcatatatca atccagttgt   1920
tactctctgg taacatcaat ctaacaagag ttcagtccat gctgtttgtc tcacgcaaat   1980
atatgtgtta cgttgaacgc cattcgatag tggtatatta tcaacttatc ttgtggttaa   2040
tatgattagc aaaagaataa caccatttgt cactatattt tacttctata gtataagtag   2100
ttttttaggaa tac                                                    2113

SEQ ID NO: 56           moltype = DNA  length = 1580
FEATURE                 Location/Qualifiers
source                  1..1580
                        mol_type = genomic DNA
                        organism = Zea mays
SEQUENCE: 56
gttccgtccg catctgcaca agtgatcgaa cggcacaccg cacacgcaac cggccggggc    60
cgtgaatagt ttcctgaaga cgattcccca acgacgacga cgacgacgcg cacagccacg   120
cggcacagtg ctcatcaagt acacagtagc acacacagcg tgcgtgcggc tgcaattaat   180
catatatacg ggttatttaa gggcaggcaa agcaaggcga ggcaagcagg aggccgacgg   240
cgaggtcacc cacccagcgg cggcgtacca gcacacgcta cgccagtcgg gcagtcgtgt   300
gttttttat gatagaattt tcttcgtaga catatagatg ctggtattga ttgagatgtg   360
gctagagtga tcggccggca tgcatgcgat gcgatgcgtt gcgacggagg ggagatcctt   420
ctcctgctat ctcgtctcgt ctctatacta gctccgcgcc aagaacgtcg tcacagaacg   480
tacttactac cagcaggggg ccgggccccgg gagggggctct ggccggtcga cagatcgttg   540
gcaaccaccg ccggccactc attgagcgag atgcatgggc tagtaggcta atcctatatt   600
ttttttaaca cgcatgcata tgctgatcaa tgcgaacaga cggactgaac tcgacccatc   660
tggatgtagc agtagtggtg gctgctgttt ggctggcatg gcatggcatg cgtccggcag   720
gcacgcatga cagcatccat ccagtaccct atttgtctaca tcgaatattt tgaaaattt    780
aaattcgctg gttttcgtcg actggctata tatagcgcat ggaaatgaat ttaatttagc   840
tgcagatgga aggttgttag aggacgaagg agctcaaatc gagcttttgc atggaataat   900
ttatacgttc ccagcatata tatgcataca tagacatga gctgaaccgg cgcatgtcta    960
cctactacat acaaacgagg cagatgaggt tgctagtagc tcgacgatca tgcccttgtt  1020
ctttcttatt ccccatttaa tagcaaatag agagagagga agattaaaaa aagggaatt   1080
gttcagtcag gagtcaaatt ccttctctat ctagaggcaa tacacgcagt atatatacac  1140
atatctctgt caccggatta ttgaaacttt tgtttaagta gtatagtagt atatagcaag  1200
caagatttta aaattttggg tgccctcaac tatacataca aaattcacca ttcacatggc   1260
ctgcttgcca ctccttcggt ccttaagagc tgctgtgccc tgccgtgccg agactgcatg   1320
agcgcgcgca agaatgttca gaaggcaaca gaacaggtcg tgcagaaatt aaattaaaat   1380
agaagaatcc atgtgagcta agctaagcat gcagcagccg ctccgtcaaa tatgtcaatg  1440
catcaaggag agtagagctc ccaatcctgc tgcttgccac ccgtcgtgga cgcacacgca   1500
tggatccgtg ttgcatatgg ccagctcgat cggagcagcg gcaggcgtca tcatccgtga  1560
cagcaacggc gcaaccaccg                                              1580

SEQ ID NO: 57           moltype = DNA  length = 1967
FEATURE                 Location/Qualifiers
source                  1..1967
                        mol_type = genomic DNA
                        organism = Zea mays
SEQUENCE: 57
gctggtgcgc gtctcaaagg tgctcgagga cttccgcgcc tccaacgccg agggttcgca    60
ccattcgcct ccctttattt tggctcctgt ttttgaactt cggagcggca aatttggtgc   120
gttcgaacga gtgtagcagt agtgttgatg caccgctcag tggactttgc gcctggggct   180
```

-continued

```
agagtttgag cgtatccttt ccaattcttg ccgcatttgg tccttttgct tttctgttct      240
ttttttttca actccattag aacagtgtat tttttgtcct gtgatcctgc cgtccttagt      300
cctgagtgca tttgtattac aacctgcgtc gtggtttgct ttgatgtttc tgttgtgtac      360
tgatcacaat agtgctgctg tttctcatcc acatcgtgct tttatcaaca tgtctgttca      420
catttgcagt tacatataac ttgcacatcg gctctctgat gctaatatcg tcacacaaag      480
tttgaacgtt ttcttaggtt tgacatgtgc taagtggtgc attcagtgtt tgtaatgtag      540
ctttccagtg atatattttg gaatctccca atcttaggtt atagaatgca atcgtctttc      600
cacaaactta taactgttta ccattgggtt gcatcttgca attttagaca tgattgttgt      660
tagatacctg tacgcctcct agatatatag taaaattgcc ttgcaaaagt ctttgcatgt      720
tttcatggct gtatattagt gggagtacca gcacattgag cacaagcaca gacccaatta      780
attgtttgat ataattattt gatggtagaa ttcagttac gcgcataagg gtcagtgtag       840
cagtagatct tattttgatg gcattctttt tctcgtatat tggctggccc tacttcagtt      900
gaagcctcac ccatctatat tatgtagtaa tgcattgaga ttattgctct cttcctttgg      960
tgctgtgago tgaataaact gatacttaga ctattttacc ttgcagtgta cacatttgaa     1020
cctgatatat ccaaacaaga gcgagctgca atccatgaa tgtgtaggaa atgggcatg       1080
atatccaaaa gttctgggtg agtaagataa ctaggattca ttgagcaaaa ttgtttcatc     1140
gaagagttgt aaggaatcta tggttttgct tgcgccatcc taatgttatc tttacaaaag     1200
ttacttgtta aatgtctatt ctgagttcta tttgacttca ggaacggga acgtcgacgc      1260
ctttctgttt ataaaagaaa acagaagcgg gggcctgaat tggaacaagg ccctagctac     1320
cttgggtttt ctgaagaggc taggcatgtt ttgcaggatt tatttatgca ttatcctcct     1380
ggtgatgctg atttaagtgg ggatgttgac cagaattcta gtgataaggc tgcaaacatc     1440
aaatggagaa cagatagtgc gttttgcagg cccacaatga gtaaacttga tataacgaag     1500
aaagttgaga tgctcgcctc aaaaataaat ggatccgaac agttgagaaa ggtctcacat     1560
tctggcttga taataaatatc ttcctctctt tgcttagttg ctgctactta ttagttttat    1620
ttatgagaca atcttattga tagctaaagc ctaaaggttt acttttgaac aggtcatgga     1680
agataganca aaacttccta tttcatcctt caaggatgtc atcacttcaa ctttggaaaa     1740
tcaccaggta tagttttag ctccaaaggt ttctcacatt tgctagacca catcttcaac      1800
tcacatggtg cactggtgct agttttcct ctcagatgtg cagggaaact gtttttttttt     1860
cattaaagaa gcatagcata atacaacaat ccccaatccc caaggcccca accaaaaaac     1920
agaaaggaaa aactgggttt ccatcgtgaa ttttagaaca tgcatac                   1967

SEQ ID NO: 58           moltype = DNA  length = 1606
FEATURE                 Location/Qualifiers
source                  1..1606
                        mol_type = genomic DNA
                        organism = Zea mays
SEQUENCE: 58
tcgcgttcta cgcgaaccac agtctaagcg agagagttta cccggtccat ttcgtttatc       60
cgttacaaat gttggctgac agctgtataa atccatcagc tttgcacagtc acagtaagga    120
cgtttacatg gtcaagtact ggtcaagaat acgaacgcca gaacacgtat gaaagaacac      180
ccccaatcat atatatgtac atgccgccgg ctggcgggcc ttaataattc tgtaaaaagg     240
tttaacataa ttggccgtaa aaaatttca ctggcagata gctagggcgt ggcgatcgag      300
tgtggtgtgt gtgtcagctg gcaagttgcg agtgctcagc gtctactacg atccacgagg    360
catgtacgta tcccggtgga tctatcccat gcaatgccaa cgcactggtc gcgctagtac    420
gtgccacttt attatttatt ttgagaccgg cccggcccgg cccggtcatg catatgtgtg    480
gcgcttgtag aaggctgctt gcctgctctg cttgtcatca tcacacacgg ttgagacctg    540
tcgacttgag atcaatcaac taacaagcta gtgtagtgta gtgttgcgtt ttgattgaga     600
aaaacgaacc tgatgtattc actaaaacgg ccacacatta ttgtcgcttc gttgggcaat    660
catatcggat gtttacggtc gaggtacaat gcatggctat atgtgcacaa aaagaaaagc    720
tgatgaaccg gccagcagca tcgtcgtccg tatccatgca atttatcgta ctgccagaaa    780
cgtgaagaca cagcaggact tgcacattct ttgactgatt tgtttttaagc cgatgcgtct   840
tcgtaagtag tatctcggtt agttgtcctt cagtggttgt caggcgccca accaacagga    900
tggcatgcgg gagatgcggc gtcacctggt tgcttcttcg cctcttcttt ttgcccaagt    960
ttcttggtca ctttagctca cttttggact actgcgaaat ttacccggcc ggttctgcgt   1020
atacaccaca gggtcgtgat actttttttta ctttccaggtc gcacttgcat cactgcatgg  1080
ttcctccgga agcagatagt cttaaagtta cgtttggtaa aggtgtggaa cgaccgaacg   1140
agtaaactga ttggtgcgcc gcttgtactt gtgatcttct gaaccagagt tcagtccacc   1200
taccacggta tgtgtggtgg gaatacccat tcgcaacaag gggacaggta acttgtttct    1260
gatttatagc attgccgtgt gaaaggttgg aaccaaagta tgtcgtgtgt accagtgtat    1320
gtggagaccg tgtcttaggt gaggacaaga aaattgtttt aaaagatttt ccatttgctc    1380
aagaataaaa tttcacatat ccctagtgtg atacagaaat aactgaataa ggtctaagtt   1440
ggtatgcaaa cttgttccgg caaatccgag actaaaaaaa catgtggtgc ccacatgtat    1500
cagtcttgta aaccaagagt tcaatatgcc taccacaata tgtatgaaag ctactcccta   1560
tagagattca cttgcctcag atttaccatc actacagcaa gagagc                   1606

SEQ ID NO: 59           moltype = DNA  length = 2765
FEATURE                 Location/Qualifiers
source                  1..2765
                        mol_type = genomic DNA
                        organism = Zea mays
SEQUENCE: 59
tgcatacaat tacgctaaat ggtgcttcgc tgagaatatt gtagtacctg cagtttgtca       60
gtagtccccct tggagtacat aaaggaaacc ctccagtcat atgcatgtaa gacctttggc    120
tcatcctcaa tactaagttt taagtacaaa tcttgtccgg ccctgtttgt gaatgttata     180
tacgggcgta catggataac ctgttgttgc ataacatgaa gtcaactgat tgacacttta    240
atatgaagtt gtagattaac atgcagctac ctttgttgga acagcttgat acgaggatgg    300
ctttgaacaa agaagaatat gcatgcattt tccatcatca tcataggcag aaagatcaac    360
tgctccatcc tgaatatgga atcagtacta tttaattgta gtggtagaaa acaagaaaaa   420
gaagaaaaga agatccaaac taccatatc gccaagaggc gacaattctt tcacagatcc    480
```

```
aaaccgtcca ccatgtccaa cagatgatag aagtcctaat cccttaaaat ttaatccaga    540
cgctatagtg tatccctcaa ccaattcatc gtgttttata tcatagagtt gcttctcacc    600
cctttccaga tgtgaacgtg aaagaaggcg cctcttctct ttccttccag aaatatcaat    660
gagacgcaga gtaagtggag gcaatctaga aaaagatatc caatagggaa catatattct    720
gataagcctt gccatcaaat agtcactatc actgcttttgt tcaagcagaa tctgtacaac    780
cctacagaag aatgaaagac aaacaggata aaagatgatt agtgaaaggt tatggcattt    840
tatccaccat aattttttca tgtttgtgtt gttaccttcc tgataaagag cttcttagat    900
tgataaattt ggaaggtgct tgggttggat gtgatataac aacaggctcc taggaccaga    960
aaatcatttc aatagtatgt agaaaaaaaa tagaaaagca aggcatctat aaaaggaagt   1020
aattttatcc atacatgcat cagttcccat cctccatgtg gaaccaggga taagtacaaa   1080
gggtttcttg gatcaacatt gtgaaccttt acagcctcac ccggacttaa ggtgccaagg   1140
gagcaacttg aatcttcatt atcgaggtgg ctagaactga cagtataatg tgcagcaatg   1200
ggaagatagt atgtcaaaca caacgggac ttaataatga tgcaccaatc atatattggt    1260
tccatctgta catctttgcc tatttccttg ccttctatgt tcaagcaaaa ccacagtcca   1320
tgacaagaat tcgaggtgcc atctacctgt gagcagaata gcaagttttc cgattcatac   1380
agatctgata cacataaatc taggatctcc tcctttctaa actcggtttg actgcgcctc   1440
tcctggacat cactccagga gtaattttca tgatcatgat gttttgccgg ccttaactgc   1500
aacatatagg gcataagagg atgtgagagg cctgatagtg ggactggaat agtagaattg   1560
ggctccagcg ttccaatcag gatttgatcc tctttaccaa aactgtctcc ctgttcatct   1620
gcccgtgcac tttgagaaat tcttcctttt agacgtaaat caacaatgaa attggttgta   1680
ttagtaactg acacaaggga acgtatgcta acgtatctgt tgccttcctt gactgttgct   1740
tcactagcaa tcacacaatt accaaacctc caacatgctc caggtacagc atagttcaac   1800
ttcatgcttg tccatggccc ttctttgaa gggctaatct gaatatatcc agtcttgctt    1860
tcaggactgg ctctgttccc ttgttgtaca ctagctctac cagaaacaag taccgcaaat   1920
cttatttttc cactaggttt aacagtttcc tgttcctgca agaattgtc aatataattt    1980
tataaaatat tgtaagtata tttcgcagaa gcacacttgt tgtgactctc attttgcaaa   2040
agtgactcaa tacatgattc tccaaatgtc agagttctca ccactgtctt agttgacata   2100
aggtctccta aagccaaatc aaatttgaca gagtccggat tagaggtagg agggagcttt   2160
tgcacaactg gctccaatgg agcagagtat ataccaactg gttgacctgt tctcaacata   2220
aactataaac tagagttggg aaaaaacaaa aaaaaaggca tttgttgtga actaaaatca   2280
cgaacccttta ccagcatcaa gcacaagaag ctctagagta tagctgtcct gaaacattgc   2340
agtgaaaatg aaatgttact taaatgaaag catgcctctt ggaaaattca ccattaataa   2400
cagtagagaa caatttccat ggatatctaa accaaagaga gtaaaagtgt tccagaatgt   2460
tttgcgttta cataccacac gttcgacttt gaaaaagaac atttcgttcc agttcacctt   2520
tctggtgttc tgtgacaagt gttctccaat agcagcacaa gtacgggcac tctgttgttg   2580
aacagatatg gaatggtttt ctgaaaagag ccgcacagca gtcatatatt caccagtttc   2640
taatccttca tcatccttga cctgggatgg gaacctaagt ttagaacagc caaaaaagtc   2700
cttcgcaaca acttacttag caggcaagtt aactgcaata caaggttcag aattcggtgt   2760
aaaac                                                               2765

SEQ ID NO: 60           moltype = DNA  length = 1725
FEATURE                 Location/Qualifiers
source                  1..1725
                        mol_type = genomic DNA
                        organism = Zea mays
SEQUENCE: 60
ccttttactt tcctccagac taagcgatcg gaacctgctt attatgccgc acaatctgct     60
attttttcact tctgattact tgtagtggtt caatgaaaaa agaagagtac ttatagtggt    120
tgcatgtacg tgatgaccga ggtacacaag tgttctacgt gaagtgttat agatcaagca    180
cttgtgctga ttggaattgt tattttgttt gaactggcca ccatgtcatg tagttctatg    240
attacattga tggaaaataa atgccttttac ccttttctga aaaataaaat taggtatcca    300
tttaagaagg aacgggcttg tgtatttcca gttgcttgtt gccttgttga cttaaggagg    360
tcaagccatg cataacttta atgctgcccc tttacattat ttttttggggta ggttgtggtt   420
gaattggtga tatgtgtggt gtggtgtagc gaaaggtgct gcaggagagg tctgattatt    480
gtttttgaac ttaccccctt gttagggatg caacagttga aatttctaa ttgccaaata    540
ttcattattg ttttgagaaa acttctaatt tggtaatctt tccttgatct attattattg    600
tttaaaaaa tataataatt ttgttgtaaa cgaacatata gtaggcacaa gaagctagtg    660
attctctttg tttacttgat catatagttt tcaagattat gttggtacac aagttcaaaa    720
attcacattg gccgcgcata gcataattga tcatctacga gtggcaatgt ggcataattg    780
aagaaggcta actggcttaag acaggcaaat cgacttgttt cactaataac caataatgga    840
aacttagaca cactagaacc caccatttag aaatctagta ttcatttatt gtcatctaaa    900
taaccttcta ttgaaagcca tctcccttag agtttccaaa gctttgccca ttggatttgc    960
cctagattc caatttagtt ttggttacgt tactaggaga aggagaatag gagatgtcgc   1020
ttgcagagaa aggggttgc ggttatgtgt gagaagctca acaatctaga tcagttgtgg   1080
tcttgtgaaa gtaggaggtt gtgatcgcca agatcaacat catgcacatg aagatctatt    1140
gttgtaaacg agtttcgaac cctaaaccta accttccata cttcatactt gcattccgtt   1200
ttgccaaaca actagaactc gaccagaatt ttagtacaat agaaagttgc caatttggtt   1260
tcttttccta taggtttgtt tagatacttg cttatgacc tttttcccac caaaagattg   1320
cctaagcatt gtgttatttt tgaaggaaat aattggaacg acttaagccc ttaggctatt    1380
ggctgtgctt attatatatt ttgtttatgt ctacggggtg gaggaccagg attccttagg   1440
tggtggtcgt ggactcgtgg tccgtttcag gccgaggttt gacaccccctt cacccctgtag  1500
tggaagagaa ggattaggca gaagggagag gtaggagaag actattgcac ttcttgatcc   1560
cactaagtac attggcttcg tttacaagga catatgccaa tacaagcaag gggctagttt   1620
ccctctatta gacccctatac cttcctagcc tctattgcta atcatctagc tacttgcctt   1680
tcgtgcctct cactgatat gcctttccca cataacatat gggc                    1725

SEQ ID NO: 61           moltype = DNA  length = 1584
FEATURE                 Location/Qualifiers
source                  1..1584
```

```
                        mol_type = genomic DNA
                        organism = Zea mays
SEQUENCE: 61
gctctagtaa aattgtattt cctctggctg gcgagcggag gacgcacggag cagaagcagc    60
tggcctcagc cgctggacag tgggcctcga ctagcagcag ataggaaacc gggatagagc   120
tgccttcccc ttccggctcc gtcagtcag gcctcagatc ggtcgaatcc agcacccct    180
ccagatttgc gtcaccaatc ttcttcttct tccgccgccg ccgccgctcc cccacaagga   240
ggttagctgc tatccccaaa tcgattcatc aatcatccgt gtccttccat ttcattccag   300
tcggtcgccg cagcacggac cgagaacaga gcatccgtc acatcaaact aacctaacca   360
gcctcgtccc tcgctgcgta tctgctgcac tttcatcaac accagtcttt ctcctcctgg   420
attgcattgc ccaggcaaga gaacgcacgc acaccgaccg gaatagccat gatcttctga   480
tccaatccaa gatgggcctc aaggagcagc agctagacgc cactgaccaa actcgtgatg   540
ccgccaactc cctcgcttct gtttctgacg agcaccacga gggaccccgt gtctcaagct   600
gcagcaccga caaggattct ggccttccaa gttgccgagc ctgccattgc gtggaaccgg   660
atctaagagg cgagtccgcc ctcggattct tgggcatcgt gcccccttcc cctcccagga   720
ctgacactgg ggggccaaag gatgatgctg ccaccagccc aaggggggag atattcgtgt   780
gcgctactga cgtcgaattg cagcagcagc aggaccatct tgtggatcta gggtgttgtt   840
gcaagaacga gcttgccctt gcgcactatg cctgtgcgtt gaagtggttc atcagccatg   900
gatccaccgc ctgcgagatc tgtgaactg ttgctgcaaa tgtaaggcct gacgatttca   960
acaaggttct cgcgtccctc aaggattacc aagctctcag ggaaagtaca tccacatact  1020
ggtggttgca gcagcatagt ggtgttgatc cagacgctgt tgcagcaata cgaaggcacg  1080
agatctcatc ctggttcaat cctcacgtgc ctatctccca aggccacatt gatcaaccgc  1140
atccctcaac caataattct tctgttcttg agcagcatac tagtgttgtg gcaaacacaa  1200
gatggagttt ggagagtact ggagttttta ttgctatctg cctggttgtc attattcttg  1260
catggttggt cgctccacat gttggcaagg tatgctgcaa cttctgctaa agagtagtta  1320
gtactacgta cttgtccttt acaaatcata aagcggagga gcattttcg tgcagaaagc  1380
tgctgtaatc tgtcttcata tgcttcttgg aggtctatgc atattgactg tagtaatatc  1440
cctgagattt gtaagtaggc ggtgacatat ttcattttc ctttagcca gatttttcac  1500
ctctgactga gttaaatgt caaaaaaata aataaatatg caggttttcc cgagaatcca  1560
gtatgggtct atgcaatatt gggc                                         1584

SEQ ID NO: 62           moltype = DNA   length = 2420
FEATURE                 Location/Qualifiers
source                  1..2420
                        mol_type = genomic DNA
                        organism = Zea mays
SEQUENCE: 62
cggttgtact tgtaaatcta gctgcttgta cgatagttat atgatgtgtt ttttttatcca    60
tagcgaccac cacgacaatc tagacctagc tagtgcgact gatttttaca tcaatacatc   120
gcaaaagcta cgcacttaga gagaaaaata aacattggaa tttagagggt acagtattta   180
gcacttcgtt acagatgtgt gaaaatccgg agccgatttt gcaatagccg tggatcgctg   240
aaatcagacc ttccttgtgc tgtctaaaat aaataaatgt tttgtgttct tcgtcggaac   300
aagaacaagc accggttgct cggacctgg agaaaactgg ttgggctgtg ccgagaaaca   360
atgagcgggc tgggctgcgt cttgacggcg ggccaccaaa ctgtcccgcc gtgcgcgcag   420
ggcaacaacc acaacgtcat gtgcggcttg cttaactggg cccgttagac gcgggcttcg   480
tgtggccttg gaacacggcc gttcgacctg gcttcacgtg acgtgaacca gagcggagcg   540
gggccatcga tttcggccgc gcgaaacgcg tgcgcgaagg ccgctggatg   600
aagctccctt tgattgaagc ccgtgtgggc cgcaccgcat ggtccggccg gcgatcgtga   660
ccgttggagt acgattatt cgatgcgtat gtactcagct cgatccatat acgatatgat   720
agtacgtaga catcttagac gtaagttgtt taaggaactc tctctctctc tctctctctc   780
tctcggtttt ctgtgttcat ctcaaagttt tttcagttca aaaaccaatt cgaaaacaaa   840
tcggcttaaa attcaggtaa tcaggtcaag cgacttact ctggtctgaa taacttgaga   900
catccgggtt gccatggccg actctagaca gcggccataa acacggtggt ttctttttct   960
tattgggata gtaggtcact ccaaataaag gctattgcca tatgctaagg agacggaatt  1020
tgtgacgcca tcgccaccgg gttaacgtta atattctact actagagaat ctagcttacg  1080
tttcggttcc ggccggccag tagaaaactc tctctgaacc gaccggtcag aatccccgc  1140
tcggtgctcg gttgcttgga ccgcacgcac gcacccctat atcgtcagtg cctgtaacag  1200
ttcttattcg gtgattatta ttataatatt attccacgtt tgcacacacc gcacatccgc  1260
ccgtttgtaa aactgtgagt tgatcgtcga gacgaaaggt ggagctggag tatatggctg  1320
ggcttcgatt gccgctcgca ggtcggtgtc ggtcccgaac ttttttactc gcgctccatc  1380
accacatagc ctggcgatcc tatcgtctgc ctacggggcc gcagcggcgc tcctccatct  1440
cctgggtctc gttgtagcca catatagagt agtagattgt tcgtcctcgc aatgatccgt  1500
agtgcacaat gcccagtcga atagtcgatg aatagcacat acacatatat gcgtgtgtgt  1560
ggtcttgtca aggttaactg ctgcagagat gagatgccaa agaaaaaaca catattctaa  1620
ttaataaagc tttgtgtgcc gcgacaagct agctaggcta ctgtctcgta cgttcacgcg  1680
gtctaaatca cgggcgcagc acaaattcga tggcagcctg gactaaacga ggccgtggcc  1740
gtcgtcacca ttcaccgatc cacaggattc acccggggc aaaaccagcg cacattacct  1800
ttgcaggaca ggagttagag gcgccttttt cctggtccct ctctctgctg agcacatgca  1860
gcagctagct agctcacgct actagtcact cgcgaagaac gaatcccgag ccggcgccac  1920
tagttgtggc tagctctcgc gtctttacat tcgcagctgc agcgtccatt tcacaggcag  1980
tatacatgca tgtgatcgag tggaaggagg agaggccacc gctggccgct gccgctgct  2040
tttcacgtac aggcgccggc agtgcaattt ggcgacgatg cgaggtgttc gccagtatgt  2100
ctcgctgaaa gggtgaagcc ggagaaaggg ggaagaatgt ttgctgcggc ggatggagat  2160
aagatcgcat ctcgatggga attagaacgg ccgccggacg agtgtgttg ttggactgt  2220
ggatcgaaca ttccgccgcg cgcctgaaag gactgtcgaa gcattgtgac atctgtcagt  2280
cgatcgatcg tgtggttaac ttaacggatg ctaaccctag cttctttttt ctcttcagtc  2340
tagctagctt tctatcttgg gagacaggga cagcattttt ctttttgttt tttagtggt  2400
accttttaatt ttgctggtgt                                             2420
```

| SEQ ID NO: 63 | moltype = DNA length = 2011 |
| --- | --- |
| FEATURE | Location/Qualifiers |
| source | 1..2011 |
| | mol_type = genomic DNA |
| | organism = Zea mays |

SEQUENCE: 63

```
gcggctagtg gatggatcac acatgtttcg aactatcttc ttttccctgt atgaggtaca    60
gtagtagctt acgacgaag ggatagatat atacatacca tgctatgcgc gtctcacttg    120
tgtacctaca gctacagatg tgcatctcta tcctatctct tcactctggc cacctttct    180
tctagctcgg aaggaaaaaa aaaagcatgt attattgcat cacttttttt tttgcaaggg    240
atacggtgca gcagtactac tactgccacg cgaatgttca ttcacgccgc gtacgatagg    300
caccgctgca tgtacccacc ggcacagtac taacggttta gatgtctact acttattaat    360
tcaatcacgc gtctgcgaga aagcaagccg acgggcatct tctgcccgag tctctccgcg    420
tttctgtaac tagaattgtc atagtcaggg ttgccaaaca tcagcatccc gaggcagttt    480
ctttaattct gcttttttt atatatgtaa gtttgcttac cgaatgagct agttctaaac    540
aaactcaaaa acaaaacagg gcaactgggg gtcccttgac attgcacaga tggacctgac    600
cactttgaga ttcccccggc ttctatctcc ttttccctcc ccttggatca aatgaacaaa    660
ggagcgcatt ctctctctct ctctctctct ctctctcaaaa gattaaaaaa    720
aagcctgcat gtagtgttct ttgacaagga caaggaagcc cttttacatc aatacatcat    780
tcgtatgttg ttgttttctg tgttctttgc gttccttttt ttttccctcc ctcgccctta    840
ttttttctac ttgattgttg ccaagatctg gagcacctga tctgatcgtg tgcgctggtt    900
tactgaacct tgggagggct atacgcttcg tacgggacat accaatttca ggaattcag    960
ttatcaggta ggtggttcaa tcattcctcc ttgtggattt gtgggaagtc agagctcgca    1020
agcatcgcca aaacttagag aaaaaataga cctgaacctg agaggatgat gatccgggac    1080
gcagctttcg tatcatattc gccgctggtt tcctcactgc aaggtgtgta aagtgtaatc    1140
ctcaaagttt agacgaagca gtaccaatca taggctcaca acgacactgt aaactgtact    1200
gcacagcaga gcagctggat gatgaactaa cagcttctcg ttttttttac gcatcatatt    1260
ttttgtatcc actggtcttt atcactcacc ttctcatttt tttatgcatc atattttttg    1320
ttcccttctc cttaattccc atgcggtgaa ggagagatgc gaactaacag tttggcgctg    1380
cactgttcga ccggctaaac acggggccaa tgctctctgt acgtgcagat ggataggata    1440
gtctttgatt cttgtttcaa gatgacgtgg atagtctata atagctaaat gtttgcctcg    1500
actactaact tgccgatatg ggcgagggta actttaaatt aaatttttaa agcatttgac    1560
ttgttaaaaa aaaataaaag cctatattct ttgttgatgg agggagcaag tggctgaaaa    1620
gccgttgcca tttctgggcg ctccctaaac tacgcggcaa gcagctatt gggagccctt    1680
gtcgctgtcg acgcgatgtg cggcctcttt cttcgtcctc ttggttaggt cttatctaca    1740
tggtcacgca tccagtttat tcattaggta cgctatctgt gtgatcgtat gttcagttta    1800
atttatatgt gttagagtat aaaaaaattt atgtaaattt tacattagct tgagtcagtc    1860
agtcagagca aattaattta gcggctagac cgctagaggc tagtcgcgtg cgtgcgtcgc    1920
tgatactcac cgtcagtccg tcaccgacac ttggcctggg cggcgtgtag cagcagcacg    1980
gatacgggca atacggccgg gtgcatggtc t    2011
```

| SEQ ID NO: 64 | moltype = DNA length = 1766 |
| --- | --- |
| FEATURE | Location/Qualifiers |
| source | 1..1766 |
| | mol_type = genomic DNA |
| | organism = Zea mays |

SEQUENCE: 64

```
gctggacttc agcgccatag gtatttcgt caagctcgtt gccaaggttt atgacattga    60
ggtcagcgcc ataggtcatg gtgttaccat atcgttacgt cacttctacg ctaacatctt    120
gtcgatggtc tcaaactatg taacctcgac gctatagaac atgaaataga cctagagtct    180
cgaatcgatt gtagttttgt ctcaagtcta aacatgtgat gttgccctct tgttttgtat    240
tttgttcttt tttttgttac gagagaagag atttaaaaaa aacacaagaa ttgacgtatc    300
tgtaacgagc agagtacaca cgtgggctag ctctccgctg aaaagaatac gatttacata    360
cgtgtaaaga ttgtgcccac tcggcagaaa tttggtgatg cgggtccagg tcgttagcct    420
cggatgcagc ctgcaggcag cctgtggtgt ggtgtggtgt ggtccaaaaa gggcgggaac    480
agaaacgagg ggctgacgc ctggacccat ggatcaggtg gactggtggt ccgtgtgggc    540
gcaagcacca gtacagtaca gtacttaccc ccgctcctgc atgcatcgtc ctctgtaaac    600
acaaagcaca aggctttacc cgaaagcaca agctcaccta attaagctca tgtacgcttc    660
tggcgcgcac aatagacacg cccgtacgca ggagcacatg gcaccaaccg aatgatttga    720
gcaaccgtct ccgcatctgg aatccattcc actcacccaa acagagctcc agctccccct    780
ctatccagcg agctggacgg acgggacgga gcgtagacta gcagaacaga agccaggcag    840
gtcgtccggt cggggtcctt tccctctttc tctccgtttt ctccgctggg gaaaaagaaa    900
atcggaaaat gacgctccac ggaagaagcg cgcgagccga tggcaatgct tcccgtcagc    960
gtcgagcggc gagggtcccc gagactttt ccccccctccc cccctgcgtg ccgcacacgg    1020
ccagaacggt ccttgctgtt gcggcttcct atcttggaac agcgccgcc ggttgaatcc    1080
gccgtggagt cgagagccgt agtgattcct agtgcaagtt gcagagcgga gcaaagcaag    1140
ggaccttgcc gcaaaaaccg tggcgggtgt cgtctaactt tgtccgtcaa gggtcgccgt    1200
cggccttgac aaaacggaca gctgctgacc gtgacgagtt agaagagaga gagagaggga    1260
gatagaagaa aaatcaccca cctccggacc tccccacacg aaacgaaaag ctacgacccta    1320
cctctcttcc agacgtaacg taagcatgaa acagaaagca ctgcctgccg gaaaaacaaa    1380
aacaaaaaca aaaaaaaccc gaaagactaa taaataattc accgctcctc tttcgcattt    1440
ctccggatct tgtatgcatg atgtgtgtgt gtgtgcctgt ggataattgg acgcactcca    1500
ccctacagtc tcctctctca gcttcgttcc tgcgccccg tatcgtatcc taatgcatgc    1560
tcacggctgg gtcccgtggg ccaccaggtt tttaatgtgc ccttctgtag ccacacgcgg    1620
agaggaaaag gaacccgcaa gaaacgggag tggaatagaa ggcgtctatt tttgcacgat    1680
ggtataggaa gcctgctggc gggctcggcg gtgcctcaga gtcggcgcgt acaaaatgaa    1740
gatgcgaagc tgttggagtt gaccta    1766
```

| SEQ ID NO: 65 | moltype = DNA length = 1600 |
| --- | --- |

```
FEATURE                 Location/Qualifiers
source                  1..1600
                        mol_type = genomic DNA
                        organism = Zea mays
SEQUENCE: 65
ttcgtaataa taatgcaata ctgatggaga cgtcgacgac tggacacaga ttcatatata    60
ataatgcaat actaatgggg cgccctcagt ttcagtcttt gcgctggaaa tggccgatca   120
ttaaaaaaat ttcttttgtc gaaattcata gacttgcgaa acgatcttga aatatactta   180
cttcaccatg ttcctgcacc caaaaaaaaa agttctccca ttcccatcct cttccaggaa   240
caaaagcaca gctacccta ccaggtgagg gctgagggat gtgtagtagt actgtccatc    300
cctgcatggc tgcatggcgg aatgggcgcc ggagtcggcg gcgcttcgag aatcatgcgt   360
ggcaggcagc gagaactcca atgcaaggca gcttgctgcc atcgattgcc atgactgaaa   420
cacgcatgca tgcatgcatg cagagttcta gtgtctgcaa tggacaatga tgaatcctcc   480
tctccccctgc attgcaattg caaagcagca tgcaatgcaa tgctctagat cttccggcga   540
ctgggcgccg cgcaccacgc ccgcccgccc accaccaacc atacgcatga attttaagct   600
gcccctcatc aaccagtcat gagtcatcat tgccatgcac cccccccccc ccccccccc    660
ccccccggcc gcgtcgtccg ccgtgcctgc catgccatcg ccggaccaga cacaatgatt   720
cgcccatgat catcgccgga ccggctagtc gatgtggatc gaagcaacgt acgcactgta   780
cgctgtgctg cagtggcacc accactgtat gtatccactg caccgcttgt tgcgcccaca   840
ccaagcactt ggtagtttgc atgccccgca gagggtgcag gccggccatg cctgcaggct   900
ggctgcagcc ggctgcatgc atcggccaag cttggctgca gagctagcga tgcatactgg   960
gctactggcg tcgcaggcgg cggtgatgcg tagtgcggca gtggtcgcgg tcgcggtcgc  1020
agccggccag cgggaagcgc cactgggagtt ttggagagac gtgcatgcg ctttctccgg  1080
gcgctagcta gcttagctcg agattgactg gcaggctgca tgggcaggca gtgcgcctgc  1140
ccgcgcctga cgacggctgt gcctcggcta gcttgctgcc agtgccagtg ccaggcaagc  1200
tgacgccgcg ttcctccac caccggccac cgccatccag gatcaggttc agaagacgag   1260
aggaaagtgt gcatgatgga gaaatatact gtgagcttca gtttgcccga tgtcacagca  1320
gcgcgcgcgg tgggcgaggg aacaggagga catgtgctca gctccatgac ccggccctcc  1380
aactgtttac ggtcttcgtg gccctctaac ggttacagtg tgaggatagc gtgcgctccg  1440
tcaggccaag tcaaccggat gagtggacgc agcaaaacag tgttgcatgt cacacatgaa  1500
tagaaatttt ttttcccctt cgcggacccc tttttattca ccggtggtgc cagtaactct   1560
ttcctcccta cgcttacgta tcaatgtgca gatagctaga                         1600

SEQ ID NO: 66           moltype = DNA   length = 2367
FEATURE                 Location/Qualifiers
source                  1..2367
                        mol_type = genomic DNA
                        organism = Zea mays
SEQUENCE: 66
tatggataaa taaatccgga catagtaagt gtcacatatg ttatgctaga taggacaggg    60
tagccgcaaa tactttatga acaacggtgt tacggagtca gaatagtata tcaatgtata   120
ttcatttttcc tcttatgatg actacttcac ggacttgtat tgtattatta aaaatcaaat   180
tagggggataa aaaaattgtga ttatatcaat caaaactaaa ggcaatatta gaaacataca   240
aaaatacatg atacatgaca cttcttagtt cttacatcct catgtcataa taccaaaact   300
aagggtcata atatatccat aattgttctt gattagcaaa aaaatcataa ttgttattag   360
aataatcatg ttggtacaaa ggcttgatta tgtcctataa atgaattata gcccaaaagt   420
taaaagaaac tcaaaacaaa acataaaaga tattaacaaa ctacaagtaa atagttgata   480
aactatatta aattgttggc atagtgtcac tgctgcatgt gcaaacatct gctgctgctg   540
tatccgccgg gttcttacgc atgtatgaga cagtgatttc atgagaaaga ttattgacac   600
gaaatcagaa tccagaaaac aataacttaa acagcacaaa gggagcagca gtgtccttgt   660
tggatacctt cgtcgggaag gtgatagatc acataagaat cactaatcta aaaaacaaaa   720
cagtaagttt aagagcaaaa cagcactagt accttggcta gactgtacat tgtacttgaa   780
tactctgggt gaccaacccc cagaacacgt ccttctatct acagatggca attaaaaaaa   840
gataaattgc atacttcaac aagtgaatta caagcacatt tacatttcca ttgttttgct   900
accatgcttt gatgctttca ttgaatgggt acaggtgtta agcagcagag tgacagaaga   960
tgacaacata tattcgtata gttctgaaag gttatatttt aacctatttg tatgcgatca  1020
accaaaaatg gacaattata agtatggtca gtaagatga tagtatagca taactcaaat  1080
attgttattg tggaatatca cattggtatc aattatgaca gaggcacaaa atttcaagaa  1140
taatgttaa acataaataa gcaagagcac aaaaagttga ggtggtggtac cttcaaagca  1200
cgctgcaaaa gggggaaac aacaaacaga aaagggtata agaagcaagt tcaaatcttc   1260
gaatgaaaaa aattaagttc aagacttgga atgaaaaat taagtgcaga agtatagca   1320
gcagttgaca caaagggtat aatgctacaa tggaaacagt tcaattagcc tttcacaact  1380
tcatgagaaa aatacatcaa ggatctcccc tactgtgact tcgttactaa atttcattct  1440
gtgtatcatg ataatgatgc atatagtgag gactagcatg cctcaaacaa aaagctgctt  1500
acaaaaatgt ccattcgctc acttgcagct tgaacagagt attagcatgc aaaattttgc  1560
acagatttac aaatttctta gattatgatt cccatcaaag gtaacagata ttgtcattcc  1620
tacaaactat tgcatgcggt ctgttttcaa actgtttaat gatattcacc aaaaaagaca  1680
aaaacaaact tttcaaactg tgttgcatag caaaattaca gaagaaacta taaaatctaa  1740
acaaagaaga ataactcatg aggcaacaaa acgttacctc ataacatgtc tgggcttgag  1800
caagcttgag ttgaagatga tagcatattc caagactatg cacagttctt ccaaccctac  1860
attaaaaaat atataatttg atgaattgcc aaatttagga taccatgcat ttggtgtttc  1920
aacagttcaa cacataggat caagcataga acacattga gatagatagg aaattcatt    1980
agaatgttca tgtaggtgta gcaacgactt acatctgcag ctttatccct gaacttagc   2040
atttgaaatg ttggctgtat cgtgctaaaa tgttataagt ttgtcaaacc tataacttct  2100
atggcactgt gctccagttc acttgtgtgt gcgacgggcc tacaactgta atagcactat  2160
gctacaaaca attttttgtaa atatgtactg aacctaatct atgactatca aatggtaccc  2220
ctttattggt aggtacatg tcataaaatg tccctgggc aagctgccat gtcccttcag   2280
aaaaggggga gagctgaaa agcatcaagc agaatcagag caaattatcg aacacgacat  2340
tcagggttca tcttccgatt ggaaacc                                      2367
```

```
SEQ ID NO: 67          moltype = DNA  length = 2071
FEATURE                Location/Qualifiers
source                 1..2071
                       mol_type = genomic DNA
                       organism = Zea mays
SEQUENCE: 67
gtctatacat gtcctagttc ttggctccat gcatgccctt atagttcctg gctcatcata   60
tactactgat cgatggactc ctggatcgct gaagctgctg cgtgtacgta gttccgtgca  120
gcacgcatgt tacgattacg actttgttag caggtcgttg ttatgcgccg tacgccgcgt  180
ctaagcatat atagtcagcg tcgtcgtccc ccctggcaaa ttatttggtc gttcttctct  240
gacgatgacg aaaacacgtt caaaatgcat gcgcgtgttc ctcgcgcgcg cgttcggtaa  300
acgcgcacgg gaacgacgta cgcgagctcg tgtcccctcg atcattggat ggtctcgtac  360
gtaagtttac tacccgacgt tgcaccgcga aattcaaatg ccagtgcgga actaagtttg  420
gctgtcatac atcgtcagaa ggaaaacaga accccaaaa aaaaacataa tgaggtattc  480
ccatcagagg taagcagctt aggcggctga gttgaatttg actgaataat atccatgctt  540
gtgtgtgcgt gcctaacgca ttgtcgtcgt gttctacgta cgctgctgca tgctactact  600
ttgctactaa aagtcatgca tcgtctcagg tagagctagg ctctaataat gtactagttt  660
atttgaaacg tacgtccggc atacggaaca agtagtaata atgagcatca gatcgcgtgc  720
aatgcagagg atagcagaat atacttgtat gtagctatgt ataggccacg acttgcgtaa  780
agctctaacg gctgttcacg accccaacgt cgtacgagag gccgggaaac aatcgtccag  840
caggccgggg gccggctagc tcggttgccg taagctacga ttcttagcac attaatatta  900
cattacatgc atgcatatcc cgcaccgctg tagcatctat acacagagta ctccacatct  960
acatctcctg gaggtcgatc gacctggcta gtactagtag tacacaggcc gcgggcgcgc 1020
gcgtttggtg cacgtcgtac acaacccct tgaggaataa tcgcatgcct cgacgacgac 1080
gacgtcggag tcagcggcgt ggcaacaatg ttggttagtt gggcaaatta aattgaactc 1140
ccgaagagag acggttgaac tgatgactga gatgagtcgt cgtaaacgtg tgtgccaagg 1200
ttgggcaggg ttgggttggg ttgggccggg cgtacgtata cgtctctgat gcatcgtccc 1260
cctaaggacg gccgacgaca cacatctgtg acagtaactg acaaggactg catcactacg 1320
acgatgcacg cgtcattcgg attgtctgct tcagaataag cgagagctcc gtgccgtacg 1380
tgaccaaatc aaagcacagt cgctaaccc agcccagatg ttctagttga ctaagtgttg 1440
tttacttttt ttcccccctt aagtagatcg agtaacatcg ttatcgcgcg tattgacgga 1500
cagataacca taagctaagt ctatataagt tcggccggtg ctgagctact gcaggtagca 1560
ggatcgatat agcccaagcg atcgagaggg cattaattga ttgtgcttag ttttgtcggt 1620
tgccgctttg ctctggataa ctacaactac tccagctaga cgtagatcga cctagcgaga 1680
gctgtggact cgagagcgag attcaactc ctgaacgcgc agtctgtacg tacagctacg 1740
gcctatctaa catgccttc acttcattcc tcttctggat ttcatctccg caagtccct 1800
gggatttgct cgttttggtt cagaggattc gctgcttaca cgcacggtcc tggggttaac 1860
ggagctcaac acagtagagt accatctctc attctctctt aatatcatcg gcatgccta 1920
caactaagag tctgtcgtct tgaggcggtt gatataaac attcaccatt gttaatagcc 1980
tattactcct gacgacagag gctataccc agtctgtaga gccatggtgt agcctccatc 2040
ttggcatcaa caccgagcac cagtattatt t                                2071

SEQ ID NO: 68          moltype = DNA  length = 1577
FEATURE                Location/Qualifiers
source                 1..1577
                       mol_type = genomic DNA
                       organism = Zea mays
SEQUENCE: 68
aaggaccaac aacaagccaa aggaactaga tcactgacct cccattgcac tgaggagggc   60
tttgcgaagg gtgctcatgc acatcactct atatctagga atgagatgaa cacatgaggt  120
tttcaatcaa atgaaaaagg atggagagta ataggatggc aaggagtatt ttttgaaatt  180
tctaggcgtt ttcgaaataa tcataaatgt tggtggttgt gatgcctttt atgtaaccgc  240
gtagaagaag agagagagat agctatgctt atgataaaga agatgtgtgt tattgtttgt  300
atatgataat ttttatttac catgtgggta ttgatagtga tgcctacatg atgaatcatt  360
ttgaggagca atgcttgttt tcattattgg ccccaatgtt ttccaagatt ggacattatg  420
gaaggccttg acctcccacc ggtttattag gtaggtctcc tttatcttgc actaagactt  480
ctcatgttca tatccttagg cattggacat atggaccata caaaggtgaa aggaccatca  540
agatcctatt taggtccatt aaatatatat gtagttagaa gtagaagtgg caagtcaaga  600
ggactggtat gtcatacgtc acatgggtgc atgtcacatc ggagtgagct agcgctatca  660
agaagaaaat aaaggtaaat gtagcaatgg gtatattagt ctactatttg tacatgtgat  720
cctgaaagag acattaatat gttggcctag attggacttc ggtcttatag gacatgataa  780
gtaataactg aaactacttt cccgttccgt ttatcttatt ttcttcttc gcttcttcca  840
tctctatccc catccctatc cctctctctc tcttttaaat cctcccaaa atatacatat  900
atatccctat tgcatccctg gatcgaaagg gacatgacaa ttcgtatgag atctaggctc  960
ttcatgcagg taattccttt attacccctt tggtcttgag tgacaatcat cattaactag 1020
tgttttcatt agacttgcac ttccattcca ggtctgtaat ctagtcattt tggactagag 1080
caattcacca tcacttgtaa ttggtaagca acttattctt tttaatttgc actatcatgg 1140
aggatgtgga agcgtgattg tgcaaattat ttggggacga acactcataa agaattttgg 1200
cggagttgat atgctcaagt aacaaatcat caacatcgac atcaattgta tcgactaggc 1260
catttggatc aaccaagtgc aagcaaagcc ggacttgtca atgtcttttc taggaaattc 1320
tcagcaagaa caacttcatg tcatgcatga tcttaaggag tcccttggtc caagggtagg 1380
acctctagat aaccatggtc cacaattgat gggaccgcct cctcaatttc aacctctacc 1440
atctcattct catatcgtca aggtgaattt acttgcctct tctaaacaa gtgatttggg 1500
tttttttatt atgcggctgc tgtatgcatt gtgatgcttg ttgggtttac taatgcaagc 1560
tacggtgggc ttgtctt                                                 1577

SEQ ID NO: 69          moltype = DNA  length = 2098
FEATURE                Location/Qualifiers
```

| source | 1..2098 |
| --- | --- |
| | mol_type = genomic DNA |
| | organism = Zea mays |

SEQUENCE: 69

```
acggtcatgg gggcacgtga aagcgtacgc gtgcgcggcg ggcgcaccgt gcgcacgttg   60
gaccgagcgc ggaacggaag gcccgaaccc gaagcggcca aacccgccgc ggaaaacgta  120
cgagcgggga aggaggcgtg ggcgcccatg ctgctgggcc cgccgttagc ctcgccggcg  180
cgcgatcgta ccgcgcggcg gcggcttttt tccatgggcg gtgccgcccc gccggcgggc  240
cctccctagt cccgtcgcaa gcggccgctg gtttggttgg tcgcttcgct cggcagaaag  300
cgagcactgt tgacgggttg gcgcggcgcg gggggctcgc ttttcttgcc gtcgactcgt  360
ggctggctgc accacctgac tggcggcggg cccaccgagg cggggaagtg ggaggagaca  420
ggccggatcc gcgaccgggg cggggagggc ccccgcccc acgtctgtct gctctgggaa  480
gtgaaaccaa accagcagac gaggacgaga caagccagcc agccagcccc cgtgttgctg  540
ccgccggccg ctctcctgcc gcagcccaca gacaggaggg gcgtggggg cccgggccgg  600
agagagccac ctcgcgactc gcgccgtcgc cgctcgcaac gactttaact gccacatttg  660
tggccctgct ataaaacaaa ctgccgcatt aagacgcta ccggcctgag agagattcgg  720
gcagaatggg gaatgcagat gcatcagtgg tgcagcagtg ctacagtacc agcgtattgc  780
attgcatgtt gcatcgccgg aacgcgagca agattccttc gtcgtgaccg ctccacaacg  840
acccttgcct tggcttgcac tgtcaggtgg aagcattgtt cactgtcgga tacgtacatg  900
agatcatgtg tgcgacagac tgtacagcaa acagctagct cacatcacaa acatgtggc  960
cgggcgcaca cagactaata agctctcgtt aatttagtgt acgccgaccg cgcgtcgg  1020
tctcactttg ctgctttgca tcagatcagg taggtaggta ggttatatat gtcatttgt  1080
taagaaccat ttgctaatta acaacctgcg ccgttttggc gccaaagttt tcagacagag  1140
ttaggtcaaa ccaatcctct cttctatttt attcatcaac gcgtattaac acaaccaacc  1200
acgtatagaa cgactcctaa aaagaggctc tttcttctgc agttgtttc tttctttctc  1260
ataatgtatg agcttcgaaa agttcagcaa tgcttgctg cacttggatt acacatgttc  1320
attggtcgag tacgtgtcgt ttcagctgga tttgatgctg cgatgtagta accagctata  1380
gtgcacgcgt gggcccttttt tatcaccccc aaacccacct ttaaggaaat cgtaaaggag  1440
atacgtacat ctctatctag cttcaacgaa aggtgcgtgc caaaaacaat ggcagatgac  1500
tagattttgt gattggatga tatggaaagc aattattaat catctttga tatctcgcgg  1560
tcggattcat ttgattgata gagagccggc gttccacttt tcatattttt gcccctacta  1620
gcagacagtg gctcctgtaac ttccaatatg gatttgtggg actgaagggt taattattat  1680
ctgtattctg tataatcggt ggctgtatgt acgatataat cattttgaaa cataacggta  1740
cattatttct cattcctgtc caagaagctt aagtcatga tggatctaac taacaacagg  1800
ctaactaact tcttagtcta tgatgatcca aatatacaaa ctaaatatg agtccgctag  1860
ttaataggac tagtagttgt tagtttcata tatcaatcca gttgttactc tctggtaaca  1920
tcaatctaac aagagttcag tccatgctgt ttgtctcacg caaatatatg tgttacgttg  1980
aacgccattc gatagtggta tattatcaac ttatcttgtg gttaatatga ttagcaaaag  2040
aataacacca tttgtcacta tattttactt ctatagtata agtagttttt aggaatac    2098
```

| SEQ ID NO: 70 | moltype = DNA length = 1580 |
| --- | --- |
| FEATURE | Location/Qualifiers |
| source | 1..1580 |
| | mol_type = genomic DNA |
| | organism = Zea mays |

SEQUENCE: 70

```
gttccgtccg catctgcaca agtgatcgaa cggcacaccg cacacgcaac cggccggggc   60
cgtgaatagt ttcctgaaga cgattcccca acgacgacga cgacgacgcg cacagccacg  120
cggcacagtg ctcatcaagt acacagtagc acacacagcg tgcgtgcggc tgcaattaat  180
catatatacg ggttatttaa gggcaggcaa agcaaggcga ggcaagcagg aggccgacgg  240
cgaggtcacc cacccagcgg cggcgtacca gcacacgcta cgccagtgcg gcagtcgtg  300
gttttttat gatagaattt tcttcgtaga catatagatg ctggtattga ttgagtatgtg  360
gctagagtga tcgccggca tgcatgcgat gcgatgcgtt gcgacggagg ggagatcctt  420
ctcctgctat ctcgtctcgt ctctatacta gctccgcgcc aagaacgtcg tcacagaacg  480
tacttactac cagcagggg ccgggccccgg gaggggctct ggccggtcga cagatcgttg  540
gcaaccaccg ccggccactc attgagcgag atgcatgggc tagtaggcta atcctatatt  600
ttttttaaca cgcatgcata tgctgatcaa tgcgaacaga cggactgaac tcgacccatc  660
tggatgtagc agtagtggtg gctgctgttt ggctggcatg gcatggcatg cgtccggcag  720
gcacgcatga cagcatccat ccagtacctt attgtctaca tcgaatattt tgaaaatttt  780
aaattcgctg gttttcgtcg actggctata tagcgcat ggaaatgaat ttaatttagc  840
tgcagatgga aggttgttag aggacgaagg agctcaaatc gagcttttgc atggaataat  900
ttatacgttc ccagcatata tatgcataca tagacataga gctgaaccgg cgcatgtcta  960
cctactacat acaaacgagg cagatgaggt tgctagtagc tcgacgatca tgcccttgtt 1020
cttctttatt ccccatttaa tagcaaatag agagaagat aagttaaaaa aagggaaatt 1080
gttcagtcag gagtcaaatt ccttctctat ctagaggcaa tacacgcagt atatataca  1140
atatctctgt caccggatta ttgaaacttt tgtttaagta gtatagtagt atatagcaag 1200
caagatttta aaattttggg tgccctcaac tatacataca aaattcacca ttcacatggc 1260
ctgcttgcca ctccttcggt ccttaagagc tgctgtgccc tgccctgcgc agactgcatg 1320
agcgcgcgca agaatgttca gaaggcaaca gaacagtcg tgcagaaatt aaattaaat  1380
agaagaatcc atgtgagcta agctaagcat gcagcagccg ctccgtcaaa tatgtcaatg 1440
catcaaggag agtagagctc ccaatcctgc tgcttgccac ccgtcgtgga cgcacacgca 1500
tggatccgtg ttgcatatgg ccagctcgat cggagcagcg gcaggcgtca tcatccgtga 1560
cagcaacggc gcaaccaccg                                             1580
```

| SEQ ID NO: 71 | moltype = DNA length = 1972 |
| --- | --- |
| FEATURE | Location/Qualifiers |
| source | 1..1972 |
| | mol_type = genomic DNA |
| | organism = Zea mays |

SEQUENCE: 71
```
gctggtgcgc gtctcaaagg cgctcgagga cttccgcgcc tccaacgccg agggttcgca    60
ccattcgcct ccctttattt tggctcctgt ttttgaactt cggagcggca aatttggtgc   120
gttcgaacga gtgtagcagt agtgttgatg cgccgctcag tggactttgc gcctggggct   180
agagtttgag cgtatcccttc ccaattcttg ccccatttgg tccttgtgct tttctgttct   240
ttttttccaa ctccattaga acagtgtatt ttttgtcctg tgatcctgtc gtccttagtc   300
ctgagtgcat ttgcattaca acctgctttg tggtttgctt tgatgtttct gttgtgtact   360
gatcacaata gtgctgctgt ttctcatcca cattgtgctt ttatcaacat gtctgttcac   420
acttgcagtt acatataatt tgcacatcgg ctctctgatg ctaatattgt cacacaaagt   480
ttgaacgttt tcttaggttt gacatgtgct aagtggtgca ttcagtgttt gtaatgtagc   540
tttccagtga tatattttgg aattggccaa tcttaggtta tagaatgcaa tcgtctttcc   600
acaaacttat aactgttttc cattgggttg catcttgcaa ttttagacat gattgttgtg   660
agatagctgt acgcctccta gataatatag taaaattgcc ttgcaaaagt ctttgcatgt   720
tttcatgget gtatattagt gggagtacca gcacattgaa cacaagcaca gacccaatta   780
attgtttgat ataatttatt gatggtagaa ttcagttac gcgcataagg gtcagttgtag   840
cagtagatct tctctattttg atggcatttt tttttctcgt atattggctg ccctacttc   900
agtttaagcc tcacccatct atattatgta gtaatgcatt gagattattg ctctcttcct   960
ttggtgctgt gagctgaata aactgatact tagactattt taccttgcag tgtacacatt  1020
tgaacctgat atatccaaac aagagcgagc tgcaatccat gagatgtgta ggaaaatggg  1080
catgatatcc aaaagttctg ggtgagtaag ataactagga ttcattgagc aaaattgttt  1140
catcgaagag ttgtaaggaa tctatggtta tgcttgcgcc atcctaatgt tatctttaca  1200
aaagttactt gttaaatgtc tattctgagt tctatttaac ttcaggaacg gggaacgtcg  1260
acgcctttct gtttataaaa gaaaacagaa gcggggcct gaattggaac aaggccctag  1320
ctaccttggg ttttctgaag aggctaggca tgttttgcag gatttattta tgcattatcc  1380
tcctggtgat gctgatttaa gtgggatgt tgaccagagt tctagtgata aggctgcaaa  1440
catcaaatgg agaacagata atgcgttttg caggcccgca atgagtaaac ttgatataac  1500
gaagaaagtt gagatgcttg cctcaaaaat aaatggatcc gaacagttga gaaaggtctc  1560
acattctggc ttgacaatag tatcttcctc tctttgctta gttgctgcta cttattagtt  1620
ttattttatga gacaatctta tttatagcta aagcttaaag gtttacttttt gaacaggtca  1680
tggaagatag aacaaaactt cctatttcat cttttcaagga tgtcatcact tcaactttgg  1740
aaaatcacca ggtatagttt ttagctccaa aggtttctca catttgctag accacatctt  1800
caactcacat ggtgcactgg tgctattttt tcctctcaga tgtgcaggga aactgttttt  1860
ttttcatta aagaagcata gcataataca acaatcccca atccccaagg ccccaaccaa  1920
aaaacagaaa ggaaaaactg ggtttccact gtgaattttg gaacatgcat ac          1972
```

```
SEQ ID NO: 72           moltype = DNA    length = 20
FEATURE                 Location/Qualifiers
source                  1..20
                        mol_type = other DNA
                        organism = Zea mays
```
SEQUENCE: 72
```
agcaccggtt gctcggaccg                                                 20
```

```
SEQ ID NO: 73           moltype = DNA    length = 20
FEATURE                 Location/Qualifiers
source                  1..20
                        mol_type = other DNA
                        organism = Zea mays
```
SEQUENCE: 73
```
tacagaaacg cggagagact                                                 20
```

```
SEQ ID NO: 74           moltype = DNA    length = 20
FEATURE                 Location/Qualifiers
source                  1..20
                        mol_type = other DNA
                        organism = Zea mays
```
SEQUENCE: 74
```
taacgagcag agtacacacg                                                 20
```

```
SEQ ID NO: 75           moltype = DNA    length = 20
FEATURE                 Location/Qualifiers
source                  1..20
                        mol_type = other DNA
                        organism = Zea mays
```
SEQUENCE: 75
```
tgaaagcgat gcggtttaga                                                 20
```

```
SEQ ID NO: 76           moltype = DNA    length = 20
FEATURE                 Location/Qualifiers
source                  1..20
                        mol_type = other DNA
                        organism = Zea mays
```
SEQUENCE: 76
```
tacaatgtac agtctagcca                                                 20
```

```
SEQ ID NO: 77           moltype = DNA    length = 20
FEATURE                 Location/Qualifiers
source                  1..20
                        mol_type = other DNA
```

```
                              organism = Zea mays
SEQUENCE: 77
acgagaccat ccaatgatcg                                                       20

SEQ ID NO: 78         moltype = DNA  length = 20
FEATURE               Location/Qualifiers
source                1..20
                      mol_type = other DNA
                      organism = Zea mays
SEQUENCE: 78
tggagagtaa taggatggca                                                       20

SEQ ID NO: 79         moltype = DNA  length = 20
FEATURE               Location/Qualifiers
source                1..20
                      mol_type = other DNA
                      organism = Zea mays
SEQUENCE: 79
tgaaaccaaa ccagcagacg                                                       20

SEQ ID NO: 80         moltype = DNA  length = 20
FEATURE               Location/Qualifiers
source                1..20
                      mol_type = other DNA
                      organism = Zea mays
SEQUENCE: 80
taggtttgac atgtgctaag                                                       20

SEQ ID NO: 81         moltype = DNA  length = 20
FEATURE               Location/Qualifiers
source                1..20
                      mol_type = genomic DNA
                      organism = Zea mays
SEQUENCE: 81
cttcgtagac atatagatgc                                                       20

SEQ ID NO: 82         moltype = DNA  length = 988
FEATURE               Location/Qualifiers
source                1..988
                      mol_type = other DNA
                      organism = Zea mays
SEQUENCE: 82
ccgtggagaa aactggttgg gctgtgccga gaaacaatga gcgggctggg ctgcgtcttg           60
acggcgggcc accaaactgt cccgccgtgc gcgcagggca acaaccacaa cgtcatgtgc          120
ggcttgctta actgggcccg ttagacgcgg gcttcgtgtg gccttggaac acggccgttc          180
gacctggctt cacgtgacgt gaaccagagc ggagcggggc catcgatttc ggccgcgcga          240
aacgcgtgcg cgaggcctgc gaaaggccgc tggatgaagc tcccttttgat tgaagcccgt         300
gtgggccgca ccgcatggtc cggccggcga tcgtgaccgt tggagtacga tttattcgat          360
gcgtatgtac tcagctcgat ccatatacga tatgatagta cgtagacatc ttagacgtaa          420
gttgtttaag gaactctctc tctctctctc tctctctctc gggtttctgt gttcatctca          480
aagtttttc agttcaaaaa ccaattcgaa aacaaatcag cttaaaattc aggtaatcag           540
gtcaagcgac tttactctgg tctgaataac ttgagacatc cgggttgcca tggccgactc          600
tagacagcgg ccataaacac ggtggtttct ttttcttatt gggatagtag gtcactccaa          660
ataaaggcta ttgccatatg ctaaggagac ggaatttgtg acgccatcgc caccgggtta          720
acgttaatat tctactacta gagaatctag cttacgtttc ggttccggcc ggccagtaga          780
aaactctctc tgaaccgacc ggtcagaatc ccctgctcgg tgctcggttg cttggaccgc          840
acgcacgcac ccctatatcg tcagtgcctg taacagttct tattcggtga ttattattat          900
aatattattc cacgtttgca cacaccgcac atccgcccgt tgtaaaact gtgagttgat           960
cgtcgagacg aaaggtggag ctggagta                                             988

SEQ ID NO: 83         moltype = DNA  length = 1001
FEATURE               Location/Qualifiers
source                1..1001
                      mol_type = other DNA
                      organism = Zea mays
SEQUENCE: 83
ctctccgcgt ttctgtaact agaattgtca tagtcagggt tgccaaacat cagcatcccg           60
aggcagtttc tttaattctg cttttttta tatgtaag tttgcttacc gaatgagcta             120
gttctaaaca aactcaaaaa caaaacaggg caactgggtt tccttgaca ttgcacagat           180
ggacctgacc acttgagat tccccggct tctatctcct tttccctccc cttggatcaa            240
atgaacaaag gagcgcattc tctctctctc tctctctcta aaagattaaa aaaaagcctg          300
catgtagtgt tctttgacaa ggacaaggaa gcccttttac atcaatacat cattcgtatg          360
ttgttgtttt ctgtgttctt tgcgttcctt ttttcccct ccctccgcct ttttctact            420
tgattgttgc caagatctgg agcacctgct ctgatctgat tgtgtgcgct ggtttactga          480
acctttcgga gggctatacg cttcgtacgg ggacatacca attcaaga attcagtcat            540
caggtaggtg gttcaatcat accgatggtt tcctcactgc atcactcacc ttctcattt           600
tacgcatcat aattttttgt tcccttctcc ttaattccca tgcggtgaag gagagatgtg          660
aactaacagt ttggcgctgc actgttcgac cggctaaaca cggggccaat gctctctgta          720
cgtgcagatg gataggatag tctttgattc ttgtttcaag atgacgtgga tagtctataa          780
```

```
tagctaaatg tttgcctcga ctactaactt gccgatatgg gcagggtaa ctttaaatta    840
aattttttaaa gcatttgact tgttaaaaaa aataaaagcc tatattcttt gttgatggag    900
ggagcaagtg gctgaaaagc cgttgccatt tctgggcgct ccctaaacta cgcggcaagc    960
aggctattgg gagcccttgt cgctgtcgac gcgatgtgcg g                       1001

SEQ ID NO: 84           moltype = DNA   length = 1000
FEATURE                 Location/Qualifiers
source                  1..1000
                        mol_type = other DNA
                        organism = Zea mays
SEQUENCE: 84
acgtgggcta gctctccgct gaaaagaata cgatttacat acgtgtaaag gttgtgccca     60
ctcggcagaa atttggtgat gcggggccag gtcgttagcc tcggatgcag cctgcaggca    120
gcctgtggtg tggtgtggtc caaaaagggc gggaacagaa acgaggggct ggacgcctga    180
acccatggat caggtggtgg tggtccgtgt gggcgcaagc accagtacag tacagtacag    240
tacttccccc cccgctcctg catgcatcgt cctctgtaaa cacaaggctt tacccgaaag    300
cacaagctca cctaattaag ctcatgtacg cttctggcgc gcacaataga cacgcccgta    360
cgcaggagca catggcacca accgaatgat ttgagcaacc gtctccgcat ctggaatcca    420
ttccactcac ccaaacagag ctccagctcc ccctctatcc agcgagctgg acgggacggg    480
acggagcgta gactagcaga acagaagcca ggcaggtcgt ccggtcgggg tcctttccct    540
cttctctcc gttttctccg ctgggaaaa agaaaatcgg aaaatgacgc tccacggaag     600
aagcgcgcga gccgatggca atggttcccg tcagcgtcga gcgcgatgg tccccgagac    660
ttttcccccc cctcctcccc tgcgtgccgc acacggccgg aacggtcctt gctgttgcgg    720
ctttctatct tggaacagcg ccggccggtt gaatccgccg tgttcctagt gcaagttgca    780
gagcggagca aagcaaggga ccttgccgca aaaaccgtgg cggggtgtcg tctaactttg    840
tccgtcaagg gtcgccgtcg gccttgacaa aacggacagc tgctgaccgt gacgagttag    900
aagagagaga gagagggaga tagaagaaaa atcacccacc tccggacctc cccacacgaa    960
acgaaaagct acgacctacc tctcttccag acgtaacgta                        1000

SEQ ID NO: 85           moltype = DNA   length = 990
FEATURE                 Location/Qualifiers
source                  1..990
                        mol_type = other DNA
                        organism = Zea mays
SEQUENCE: 85
aaaccgcatc gctttcaggc tttatttaat ctctgcgtca aggaaaggag caatcttctg     60
cgagaaaaga agaaggtctc gcgtccatgt atgcagttga actgtttact catgagaatg    120
agagggggga gagagacatc agacatccca gtgaaggttt cagagacgcg actgttgatc    180
cgatgccccc ggcccctcat cagcaataat cagctgacc gaaaaagata ccgtactgg    240
gattttccat gtacccccca aaaacaatat tagctcatgc atgaactggg cgattatatc    300
gtcatttaat ttgtgggtta catgttgttt atgcgtagag agaagataga gttggtagca    360
agtcccggtt tgtgcatagc aagatgtgat ttttgtccat taattcgtca gtaggtgatg    420
attgactctg acgatgagac cgacaggcgg acgcatatat tatgcatcga tgtgcattct    480
gtgtgtgatt tgtgactcaa tattattcct ctggctagtc ttgttccgg ccatttctcc     540
ctgaattccc ctctgatctt ttttaatat tttatgtaaa gaaagaaaaa aacactgaag    600
gccgacgata tgcgcgtgag gacgacaatc gcacacgtgt ttgcatttga taacatttta    660
tcttgtctag cagacattag tttgattaac ttgtttcatg ccaatcatta atttggagta    720
tatatgattg atatcttatt atcctgtccg tttgtatatt atttaagtag catggattgg    780
agtactacac cgttaacaat acattccaca aataccttttc cctccatcca aattaaggct    840
taattttaga taatgacgca tcttcttcct atagcccacc ctatgcacag gtaagcctca    900
caaggtacgt agttttttaca ctaattatta gctttgcaaa ttgcaatata gctacaagtt    960
ttgcatcggc tgattttttt gattaattgg                                    990

SEQ ID NO: 86           moltype = DNA   length = 993
FEATURE                 Location/Qualifiers
source                  1..993
                        mol_type = other DNA
                        organism = Zea mays
SEQUENCE: 86
ctagactgta cattgtactt gaatactctg ggtgaccaac ccccagaaca cgtccttcta     60
tctacagatg gcaattaaaa aaagataaat tgcatacttc aacaagtgaa ttacaagcac    120
atttacattt ccattgtttt gctaccatgc tttgatgctt tcattgaatg ggtacaggtg    180
ttaagcagca gagtgacaga agatgacaac atatattcgt atagttctga aaggttatat    240
tttaacctat ttgtatgcga tcaaccaaaa atggacaatt ataagtatgg tcaagtaaga    300
tgatagtata gcataactca aatattgtta ttgtggaata tcacattggt atcaattatg    360
acagaggcac aaaatttcaa gaataaatgt taaacataaa taagcaagag cacaaaaagt    420
tgaggtgtgg taccttcaaa gcacgctgca aagggggga acaacaaac agaaaagggt    480
ataagaagca agttcaaatc ttcgaatgaa aaaaattaag ttcaagactt ggaatgaaaa    540
aattaagtgc agaaagtata gcagcagttg acacaaagga tataatgcta caatggaaac    600
agttcaatta gccttttcaca acttcatgag aaaaatacat caaggatctc ccctactgtg    660
acttcgttac taaatttcat tctgtgtatc atgataatga tgcatatagt gaggactagc    720
atgcctcaaa caaaaagctg cctacaaaaa tgtccattcg ctcacttgca gcttgaacag    780
agtattgcag tgcaaaattt tgcacagatt tacaaatttc ttagattatg attcccatca    840
aaggtaacag atatggtcat tcctacaaac tattgcatgc ggtctgtttt caaactgttt    900
aatgatattc accaaaaaag acaaaaacaa acttttcaaa ctgtgttgca tagcaaaatt    960
acagaagaaa ctataaaatc taaacaaaga aga                                 993

SEQ ID NO: 87           moltype = DNA   length = 998
FEATURE                 Location/Qualifiers
```

| source | 1..998 |
| --- | --- |
| | mol_type = other DNA |
| | organism = Zea mays |

SEQUENCE: 87

```
tcattggatg gtctcgtacg taagtttact acccgacgtt gcaccgcgaa attcaaatgc    60
cagtgccgaa ctaagtttgg ctgtcataca tcgtcagaag gaaaacagaa ccccaaaaa   120
aaaacataat gaggtattcc catcagaggt aagcagctta ggcggctgag ttgaatttga   180
ctgaataata tccatgcttg tgtgtgcgtg cctaacgcat tgtcgtcgtg ttctacgtac   240
gctgctgcat gctactactt tgctactaaa agtcatgcat cgtctcaggt agagctaggc   300
tctaataatg tactagttta tttgaaacgt acgtccggca tacggaacaa gtagtaataa   360
tgagcatcag atcgcgtgca atgcagagga tagcagaata tacttgtatg tagctatgta   420
taggccacga cttgcgtaaa gctctaacgg ctgttcacga ccccaacgtc gtacgagagg   480
ccgggaaaca atcgtccagc aggccggcgg ccggctagct cggttgccgt aagctacgat   540
tcttagcaca ttaatattac attacatgca tgcatatccc gcaccgctgt agcatctata   600
cacagagtac tccacatcta catctcctgg aggtcgatcg acctggctag tactagtagt   660
acacaggccg cgggcgcgcg cgtttggtgc acgtcgtaca caaccccctt gaggaataat   720
cgcatgcctc gacgacgacg acgtcggagt cagcggcgtg gcaacaatgt tggttagttg   780
ggcaaattaa attgaactcc cgaagagaga cggttgaact gatgactgag atgagtcgtc   840
gtaaacgtgt gtgccaaggt tgggcagggt tgggttgggt tgggccgggc gtacgtatac   900
gtctctgatg catcgtcccc ctaaggacgg ccgacgacac acatctgtga cagtaactga   960
caaggactgc atcactacga cgatgcacgc gtcattcg                           998
```

| SEQ ID NO: 88 | moltype = DNA  length = 999 |
| --- | --- |
| FEATURE | Location/Qualifiers |
| source | 1..999 |
| | mol_type = other DNA |
| | organism = Zea mays |

SEQUENCE: 88

```
gcaaggagta ttttttgaaa tttctaggcg ttttcgaaat aatcataaat gttggtggtt    60
gtgatgcctt ttatgtaacc gcgtagaaga agagagagaa atagctatgc ttatgataaa   120
gaagatgtgt gttattgttt gtatatgata attttttattt accatgtggg tattgatagt   180
gatgcctaca tgatgaatca ttttgaggag caatgcttgt tttcattatt ggccccaatg   240
ttttccaaga ttggacatta tggaaggcct tgacctccca ccggtttatt aggtaggtct   300
cctttatctt gcactaagac ttctcatgtt catatcctta ggcattggac atatggacca   360
tacaaaggtg aaaggaccat caagatccta tttaggtcca ttaaatatat atgtagttag   420
aagtagaagt ggcaagtcaa gaggactggt atgtcatacg tcacatgggt gcatgtcaca   480
tcggagtgag ctagcgctat caagaagaaa ataaaggtaa atgtagcaat gggtatatta   540
gtctactatt tgtacatgtg atcctgaaag agacattaat atgttggcct agattggact   600
tcggtcttat aggacatgat aagtaataac tgaaactact ttcccgttcc gtttatctta   660
tttttcttct tcgcttcttc catctctatc cctatcccta tccctctctc tctcttttaa   720
attcttcccc aaatatacat atatatccct attgcatccc tggatcgaaa gggacatgac   780
aattcgtatg agatctaggc tcttcatgca ggtaattcct ttattaccct cttggtcttg   840
agtgacaatc atcattaact agtgttttca ttagacttgc acttccattc caggtctgta   900
atctagtcat tttggactag agcaattcac catcacttgt aattggtaag caacttattc   960
ttttaatt gcactatcat ggaggatgtg gaagcgtga                            999
```

| SEQ ID NO: 89 | moltype = DNA  length = 997 |
| --- | --- |
| FEATURE | Location/Qualifiers |
| source | 1..997 |
| | mol_type = other DNA |
| | organism = Zea mays |

SEQUENCE: 89

```
acgaggacga gacaagccag cagccagctc ccgtgttgct gccgccggcc gctctctgcc    60
cgcagcccgc agcccacaga caggagggc gtgggggcc cgggccggag agagccacct    120
cgccgactcgc gccgtcgccg ctcgcaacga ctttaactgc cacattatg gccctgctat   180
aaaacaaact gccgcattta ataggctacc ggccaggcct gagagagatt cgggcagaat   240
ggggaatgca gatgcatcag tggtgcagca gtgctacagt accagcgtat tgcattgcat   300
cgccggaacg cgagcaagat tccttcgtcg tgaccgctcc aaaacgaccc ttgccttggc   360
ttgcactgtc aggtggaagc attgttcact gtcggataca tacatgagat catgtgtgcg   420
acagactgta cagcaaacag ctagctcaca tcacaaaaca tgtgccgggg gcgcacacag   480
actaataagc tctcgttaat ttagtgtacg ccgaccgcgc gcgtcggtct cactttgctg   540
cttttgcatca gatcaggtag gtaggtaggt tatatatgtc attttgttaa gaaccatttg   600
ctaattaaca acctgcgccg ttttggcgcc aaagttttca gacagagtta ggtcaaacca   660
atcctctctt ctattttatt catcaacgcg tattaacaca acaaccacg tatagaacga   720
ctcctaaaaa gaggctcttt cttctgcagt tgttttttttt ttctcataat gtatgagctt   780
cgaaagttc agcaattgct tgctgcactt ggattacaca tgttcattgg tcgagtacgt   840
gtcgtttcag ctgatttga tgctgcgatg tagtaaccag ctatagtgca cgcgtgggcc   900
ctttttatca cccccaaacc caccttaag gaaatcgtaa aggagatacg tacatctcta   960
tctagcttca acgaaaggtg cgtgccaaaa acaatgg                            997
```

| SEQ ID NO: 90 | moltype = DNA  length = 999 |
| --- | --- |
| FEATURE | Location/Qualifiers |
| source | 1..999 |
| | mol_type = other DNA |
| | organism = Zea mays |

SEQUENCE: 90

```
aagtggtgca ttcagtgttt gtaatgtagc tttccagtga tatattttgg aatctcccaa    60
tcttaggtta tagaatgcaa tcgtctttcc acaaacttat aactgtttac cattgggttg   120
catccttgcaa ttttagacat gattgttgtt agataccgtg acgcctccta gatatatagt   180
```

```
aaaattgcct tgcaaaagtc tttgcatgtt ttcatggctg tatattagtg ggagtaccag    240
cacattgagc acaagcacag acccaattaa ttgtttgata taattattg atggtagaat    300
tctagttacg cgcataaggg tcagtgtagc agtagatctt attttgatgg cattcttttt    360
ctcgtatatt ggctggccct acttcagttg aagcctcacc catctatatt atgtagtaat    420
gcattgagat tattgctctc ttcctttggt gctgtgagct gaataaactg atacttagac    480
tattttacct tgcagtgtac acatttgaac ctgatatatc caaacaagag cgagctgcaa    540
tccatgagat gtgtaggaaa atgggcatga tatccaaaag ttctgggtga gtaagataac    600
taggattcat tgagcaaaat tgtttcatcg aagagttgta aggaatctat ggttttgctt    660
gcgccatcct aatgttatct ttacaaaagt tacttgttaa atgtctattc tgagttctat    720
ttgacttcag gaacggggaa cgtcgacgcc tttctgttta taaagaaaa cagaagcggg    780
ggcctgaatt ggaacaaggc cctagctacc ttgggttttc tgaagaggct aggcatgttt    840
tgcaggattt atttatgcat tatcctcctg gtgatgctga tttaagtggg gatgttgacc    900
agaattctag tgataaggct gcaaacatca aatggagaac agatagtgcg ttttgcaggc    960
ccacaatgag taaacttgat ataacgaaga aagttgaga                         999

SEQ ID NO: 91            moltype = DNA   length = 986
FEATURE                  Location/Qualifiers
source                   1..986
                         mol_type = other DNA
                         organism = Zea mays
SEQUENCE: 91
tgctggtatt gattgagatg tggctagagt gatcggccgg catgcatgcg atgcgatgcg     60
ttgcgacgga ggggagatcc ttctcctgct atctcgtctc gtctctatac tagctccgcg    120
ccaagaacgt cgtcacagaa cgtacttact accagcaggg ggccgggccc gggaggggct    180
ctggccggtc gacagatcgt tggcaaccac cgccggccac tcattgagcg agatgcatgg    240
gctagtaggc taatcctata tttttttaa cacgcatgca tatgctgatc aatgcgaaca    300
gacggactga actcgaccca tctggatgta gcagtagtgg tggctgctgt ttggctggca    360
tggcatggca tgcgtccggc aggcacgcat gacagcatcc atccagtacc ttattgtcta    420
catcgaatat tttgaaaatt ttaaattcgc tggttttcgt cgactggcta tatatagcgc    480
atggaaatga atttaattta gctgcagatg gaaggttgtt agaggacgaa ggagctcaaa    540
tcgagctttt gcatggaata atttatacgt tcccagcata tatatgcata catgacata     600
gagctgaacc ggcgcatgtc tacctactac atacaaacga ggcagatgag gttgctagta    660
gctcgacgat catgccctgt tcttctttta ttccccattt aatagcaaat agagagagag    720
agagattaaa aaaagggaaa ttgttcagtc aggagtcaaa ttccttctct atctagaggc    780
aatacacgca gtatatatac acatatctct gtcaccggat tattgaaact tttgtttaag    840
tagtatagta gtatatagca agcaagattt taaaattttg ggtgccctca actatacata    900
caaaattcac cattcacatg gcctgcttgc cactccttcg gtccttaaga gctgctgtgc    960
cctgccctgc gcagactgca tgagcg                                         986

SEQ ID NO: 92            moltype = DNA   length = 22
FEATURE                  Location/Qualifiers
source                   1..22
                         mol_type = other DNA
                         organism = Zea mays
SEQUENCE: 92
tgacaagacc acacacacgc at                                              22

SEQ ID NO: 93            moltype = DNA   length = 23
FEATURE                  Location/Qualifiers
source                   1..23
                         mol_type = other DNA
                         organism = Zea mays
SEQUENCE: 93
gtgacggact gacggtgagt atc                                             23

SEQ ID NO: 94            moltype = DNA   length = 23
FEATURE                  Location/Qualifiers
source                   1..23
                         mol_type = other DNA
                         organism = Zea mays
SEQUENCE: 94
atgatgtgtg tgtgtgtgcc tgt                                             23

SEQ ID NO: 95            moltype = DNA   length = 21
FEATURE                  Location/Qualifiers
source                   1..21
                         mol_type = other DNA
                         organism = Zea mays
SEQUENCE: 95
tgcccacttt tgctttcaca t                                               21

SEQ ID NO: 96            moltype = DNA   length = 23
FEATURE                  Location/Qualifiers
source                   1..23
                         mol_type = other DNA
                         organism = Zea mays
SEQUENCE: 96
tgaactgttg aaacaccaaa tgc                                             23
```

```
SEQ ID NO: 97           moltype = DNA   length = 20
FEATURE                 Location/Qualifiers
source                  1..20
                        mol_type = other DNA
                        organism = Zea mays
SEQUENCE: 97
tcagcaccgg ccgaacttat                                                       20

SEQ ID NO: 98           moltype = DNA   length = 22
FEATURE                 Location/Qualifiers
source                  1..22
                        mol_type = other DNA
                        organism = Zea mays
SEQUENCE: 98
gctttgcttg cacttggttg at                                                    22

SEQ ID NO: 99           moltype = DNA   length = 25
FEATURE                 Location/Qualifiers
source                  1..25
                        mol_type = other DNA
                        organism = Zea mays
SEQUENCE: 99
gcttcttgga caggaatgag aaata                                                 25

SEQ ID NO: 100          moltype = DNA   length = 24
FEATURE                 Location/Qualifiers
source                  1..24
                        mol_type = other DNA
                        organism = Zea mays
SEQUENCE: 100
agcagcaact aagcaaagag agga                                                  24

SEQ ID NO: 101          moltype = DNA   length = 19
FEATURE                 Location/Qualifiers
source                  1..19
                        mol_type = other DNA
                        organism = Zea mays
SEQUENCE: 101
aagcagcagg attgggagc                                                        19

SEQ ID NO: 102          moltype = DNA   length = 21
FEATURE                 Location/Qualifiers
source                  1..21
                        mol_type = other DNA
                        organism = Zea mays
SEQUENCE: 102
tgtgctgcaa ggcgattaag t                                                     21

SEQ ID NO: 103          moltype = DNA   length = 21
FEATURE                 Location/Qualifiers
source                  1..21
                        mol_type = other DNA
                        organism = Zea mays
SEQUENCE: 103
tgtgctgcaa ggcgattaag t                                                     21

SEQ ID NO: 104          moltype = DNA   length = 21
FEATURE                 Location/Qualifiers
source                  1..21
                        mol_type = other DNA
                        organism = Zea mays
SEQUENCE: 104
tgtgctgcaa ggcgattaag t                                                     21

SEQ ID NO: 105          moltype = DNA   length = 20
FEATURE                 Location/Qualifiers
source                  1..20
                        mol_type = other DNA
                        organism = Zea mays
SEQUENCE: 105
ccgggtgaat cagcgtttat                                                       20
```

TARGETED INSERTION SITES IN THE MAIZE GENOME

RELATED APPLICATIONS

This application claims benefit of application Ser. No. 16/757,815 filed Apr. 21, 2020, which is a 371 of International Application No. PCT/US2018/065114, filed Dec. 12, 2018, which claims the benefit of U.S. provisional Application No. 62/599,831, filed Dec. 18, 2017, the contents of which are incorporated herein by reference.

STATEMENT REGARDING ELECTRONIC SUBMISSION OF A SEQUENCE LISTING

A sequence listing in ST26 format, submitted under 37 C.F.R. § 1.821, entitled "81487seqlisting.xml", 238 kilobytes in size, generated on Aug. 26, 2022 and filed via EFS-Web is provided in lieu of a paper copy. This sequence listing is hereby incorporated by reference into the specification for its disclosures.

BACKGROUND OF THE INVENTION

Recent advances in the field of targeted genomic modifications have made it so that routine targeted modifications for agrobiotechnological approaches may soon be possible. Significant advances include the development of methods and compositions to target and cleave genomic DNA by site specific nucleases (e.g., Zinc Finger Nucleases (ZFNs), Meganucleases, Transcription Activator-Like Effector Nucleases (TALENS) and Clustered Regularly Interspaced Short Palindromic Repeats/CRISPR-associated nucleases (CRISPR/Cas) with an engineered crRNA/tracr RNA), to induce targeted mutagenesis, to induce targeted deletions of DNA sequences, and to facilitate targeted recombination of an exogenous donor DNA polynucleotide, such as a transgene, within a predetermined genomic locus. However, this predetermined genomic locus is not obvious. Many sites in the genome are non-ideal for targeted genomic modifications, particularly for targeted insertion of a DNA of interest, due a number of factors, including highly repetitive nucleotide sequences, methylation, chromatin structure, epigenetic modifications such as acetylation, and other characteristics that result in a high level of recombination or a poor level of expression of introduced coding sequences. Therefore, there is a need in the art to identify ideal target sites within a genome for targeted modifications such as transgene insertion. The present invention addresses these shortcomings in the art by providing ideal target sites for a maize genome.

SUMMARY OF THE INVENTION

The present invention provides a method of integrating a DNA of interest into a target maize genomic locus, wherein the target maize genomic locus comprises a nucleic acid sequence of at least 100, at least 500, at least 750, at least 1,000, at least 1,250, or at least 1,500 contiguous nucleotides having at least 70%, at least 75%, at least 80%, at least 85%, at least 90%, at least 93%, at least 95%, at least 96%, at least 97%, at least 98%, at least 99%, or 100% identity to at least 100, at least 500, at least 750, at least 1,000, at least 1,250, or at least 1,500 contiguous nucleotides of SEQ ID NO: 1 through SEQ ID NO: 71, or a complement thereof, comprising introducing into a maize cell: (a) a first nucleic acid molecule comprising at least 50, at least 60, at least 70, at least 80, at least 90, at least 100, at least 110, at least 120, at least 130, at least 140, or at least 150 contiguous nucleotides, wherein said contiguous nucleotides have at least 80% identity to at least 100, at least 110, at least 120, at least 130, at least 140, or at least a 150 contiguous nucleotides of SEQ ID NO: 1 through SEQ ID NO: 71, or a complement thereof, and further comprising a DNA of interest; and (b) a second nucleic acid molecule comprising a nucleotide sequence encoding a nuclease for site-directed cleavage at a genomic nuclease cleavage site of, adjacent to, or proximal to the genomic nucleotide sequence of SEQ ID NO: 1 through SEQ ID NO: 71, or a complement thereof, that corresponds to the contiguous nucleotides of (a), under conditions wherein expression of the second nucleic acid molecule can occur to produce the nuclease and the nuclease can cleave the nucleotide sequence at the genomic nuclease cleavage site, whereby the DNA of interest is integrated at the genomic nuclease target cleavage site in the maize genome.

In some embodiments, the first nucleic acid molecule and the second nucleic acid molecule can be introduced into the maize cell by biolistic nucleic acid delivery, via an *Agrobacterium*, by co-transformation, and/or with a T-DNA vector in any combination and/or order. In some embodiments, the first nucleic acid molecule and the second nucleic acid molecule can be present on a single nucleic acid construct or on separate nucleic acid constructs.

In some embodiments, the first nucleic acid molecule and/or the second nucleic acid molecule can be transiently expressed in the maize cell or can be stably integrated into the maize genome of the maize cell.

In some embodiments, the DNA of interest comprises at least one expression cassette. In some embodiments, the DNA of interest comprises a transgene.

In another embodiment, the present invention provides a method of making a maize plant cell comprising a DNA of interest, said method comprising: (a) selecting a target maize genomic locus, wherein the target maize genomic locus comprises a nucleic acid sequence of at least 100, at least 500, at least 750, at least 1,000, at least 1,250, or at least 1,500 contiguous nucleotides having at least 70%, at least 75%, at least 80%, at least 85%, at least 90%, at least 93%, at least 95%, at least 96%, at least 97%, at least 98%, at least 99%, or 100% identity to at least 100, at least 500, at least 750, at least 1,000, at least 1,250, or at least 1,500 contiguous nucleotides contiguous nucleotides of SEQ ID NO: 1-71 or a complement thereof; (b) selecting a site specific nuclease that specifically binds to and cleaves a genomic nuclease cleavage site within said target maize genomic locus; (c) introducing said site specific nuclease and a DNA of interest into the maize plant cell; (d) allowing the DNA of interest to insert into the target maize genomic locus; and (e) selecting maize plant cells that comprise the DNA of interest inserted into the target maize genomic locus.

The site specific nuclease of the method described above may be introduced into the maize plant cell either as a polypeptide or as nucleic acid molecule, which is transcribed and/or translated in the plant cell to produce the site specific nuclease. The site specific nuclease may be transiently expressed in the plant cell. The site specific nuclease may not be expressed in the maize cell, and may only be present in the maize cell as an active nuclease. The site specific nuclease and the DNA of interest may be introduced into the cell simultaneously or not simultaneously.

In some embodiments of the methods of the invention, the site specific nuclease is a CRISPR-associated nuclease, a zinc finger nuclease, a TALEN, or a meganuclease, singly or in combination. In some embodiments of the methods of the invention, the site specific nuclease is a CRISPR-associated nuclease, such as Cas9 or Cpf1, and the method includes at least one additional nucleic acid molecule encoding a guide RNA, which is also introduced into the maize cell. The guide RNA may be a single guide RNA or a dual guide RNA. The additional nucleic acid molecule(s) may be DNA molecule(s) that can be expressed in the maize cell to produce the guide RNA, or it may be RNA molecule(s), the guide RNA itself, which is introduced into the maize cell.

The present invention further provides a method of producing a maize plant, plant part, or progeny thereof comprising a DNA of interest, such as a transgene, integrated into the genomic nuclease cleavage site in the maize genome, comprising regenerating a maize plant from the maize cell produced by the method described herein. Accordingly, the present invention provides a maize plant, plant part, or progeny thereof comprising the transgene integrated into the genomic nuclease cleavage site in the maize genome, produced by the method of this invention.

The present invention also provides a maize recombinant polynucleotide, wherein the recombinant polynucleotide comprises a nucleic acid sequence of at least 50 nucleotides, at least 60, 70, 80, 90, 100, 150, 200, 250, 300, 250, 400, 450, 500, 600, 700, 800, 900, 1000, 1500, 2000, 2500, 3000, 3500, 4000, 4500, 5000, 7500, 10000, 15,000 or at least 20,000 nucleotides, and has at least 70%, at least 75%, at least 80%, at least 85%, at least 90%, at least 93%, at least 95%, at least 96%, at least 97%, at least 98%, at least 99%, or 100% identity to at least 50 contiguous nucleotides, 60, 70, 80, 90, 100, 150, 200, 250, 300, 250, 400, 450, 500, 600, 700, 800, 900, 1000, 1500, 2000, 2500, 2750, 2900, or at least 3000 contiguous nucleotides of SEQ ID NO: 1-71 or a complement thereof, and wherein the recombinant polynucleotide further comprises a DNA of interest, wherein the DNA of interest is inserted into the nucleic acid sequence to produce said recombinant polynucleotide.

In some embodiments, the recombinant polynucleotide comprises a DNA of interest which is a transgene. In some embodiments, the DNA of interest comprises at least one gene of interest. In some embodiments, the DNA of interest comprises at least one expression cassette. In some embodiments, the DNA of interest comprises two or more expression cassettes. In some embodiments, the DNA of interest does not encode a polypeptide. In some embodiments, the DNA of interest comprises regulatory sequences.

The present invention also provides a maize plant, plant part, or plant cell comprising the recombinant polynucleotide described above.

BRIEF DESCRIPTION OF THE SEQUENCES IN THE SEQUENCE LISTING

The nucleic acid sequences listed in the accompanying sequence listing are shown using standard letter abbreviations for nucleotide bases, as defined in 37 C.F.R. § 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence reference to the nucleic acid sequence, unless it is explicitly stated to be otherwise (or it is clear to be otherwise from the context in which the sequence appears). Furthermore, as it is understood in the art that the nucleotide sequence of an RNA strand is determined by the sequence of the DNA from which it was transcribed (but for the substitution of uracil (U) nucleobases for thymine (T)), an RNA sequence is included by any reference to the DNA sequence encoding it. In the accompanying sequence listing:

SEQ ID NOs: 1 to 61 are nucleotide sequences of identified safe harbor sites, ideal for targeted integration, within the genome of the maize elite inbred line AX5707.

SEQ ID NOs: 62 to 71 are nucleotide sequences of identified safe harbor sites, ideal for targeted integration, within the genome of the maize variety B73.

SEQ ID NOs: 72 to 81 are nucleotide sequences of target maize genomic loci for targeted insertion of a DNA of interest using the CRISPR-Cas9 system SEQ ID NOs: 82 to 91 are nucleotide sequences of maize genomic fragments from the elite inbred line AX5707 which can be used as homologous arms for recombination into a safe harbor site.

SEQ ID NOs: 92 to 105 are primers useful to the invention.

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

As used in the description of the embodiments of the invention and the appended claims, the singular forms "a," "an," and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The terms "comprise," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

The following definitions and methods are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in Rieger et al., *Glossary of Genetics: Classical and Molecular*, 5$^{th}$ edition, Springer-Verlag: New York, 1994.

The terms "nucleotide sequence" "nucleic acid," "nucleic acid sequence," "nucleic acid molecule," "oligonucleotide" and "polynucleotide" are used interchangeably herein to refer to a heteropolymer of nucleotides and encompass both RNA and DNA, including cDNA, genomic DNA, mRNA, synthetic (e.g., chemically synthesized) DNA or RNA and chimeras of RNA and DNA. The term nucleic acid molecule refers to a chain of nucleotides without regard to length of the chain. The nucleotides contain a sugar, phosphate and a base which is either a purine or pyrimidine. A nucleic acid molecule can be double-stranded or single-stranded. Where single-stranded, the nucleic acid molecule can be a sense strand or an antisense strand. A nucleic acid molecule can be synthesized using oligonucleotide analogs or derivatives (e.g., inosine or phosphorothioate nucleotides). Such oligonucleotides can be used, for example, to prepare nucleic acid molecules that have altered base-pairing abilities or increased resistance to nucleases. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism. Unless otherwise indicated, a particular nucleic acid sequence of this invention also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid molecule is used interchangeably with gene, cDNA, and mRNA encoded by a gene.

The term "derived from" in the context of a molecule refers to a molecule isolated or made using a parent molecule or information from that parent molecule. For example, a Cas9 single mutant nickase and a Cas9 double mutant null-nuclease are derived from a wild-type Cas9 protein.

A "coding sequence" is a nucleic acid sequence that is transcribed into RNA such as mRNA, rRNA, tRNA, snRNA, sense RNA or antisense RNA. In some embodiments, the RNA is then translated in an organism to produce a protein.

By the term "express" or "expression" of a polynucleotide coding sequence, it is meant that the sequence is transcribed, and optionally translated.

"Expression cassette" as used herein means a nucleic acid molecule capable of directing expression of a particular nucleotide sequence in an appropriate host cell, comprising a promoter operably linked to the nucleotide sequence of interest, typically a coding region, which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). In some embodiments, a gene refers to only the coding region. A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

The term "native gene" refers to a gene as found in nature. The term "chimeric gene" refers to any gene that contains 1) DNA sequences, including regulatory and coding sequences that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Promoter" refers to a nucleotide sequence, usually upstream (5') to its coding sequence, which controls the expression of the coding sequence by providing the recognition for RNA polymerase and other factors required for proper transcription. "Promoter regulatory sequences" consist of proximal and more distal upstream elements. Promoter regulatory sequences influence the transcription, RNA processing or stability, or translation of the associated coding sequence. Regulatory sequences include enhancers, promoters, untranslated leader sequences, introns, and polyadenylation signal sequences. They include natural and synthetic sequences as well as sequences that may be a combination of synthetic and natural sequences. An "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. The meaning of the term "promoter" includes "promoter regulatory sequences."

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. For purposes of the present invention, the definition of the term "intron" includes modifications to the nucleotide sequence of an intron derived from a target gene, provided the modified intron does not significantly reduce the activity of its associated 5' regulatory sequence.

"Exon" refers to a section of DNA which carries the coding sequence for a protein or part of it. Exons are separated by intervening, non-coding sequences (introns). For purposes of the present invention, the definition of the term "exon" includes modifications to the nucleotide sequence of an exon derived from a target gene, provided the modified exon does not significantly reduce the activity of its associated 5' regulatory sequence.

A "transgene" refers to a nucleic acid molecule that has been introduced into the genome by transformation and is stably maintained. A transgene may comprise at least one expression cassette, typically comprises at least two expression cassettes, and may comprise ten or more expression cassettes. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but one that is introduced into the organism by gene transfer.

As used herein the term transgenic "event" refers to a recombinant plant produced by transformation and regeneration of a single plant cell with heterologous DNA, for example, an expression cassette that includes one or more genes of interest (e.g., transgenes). The term "event" refers to the original transformant and/or progeny of the transformant that include the heterologous DNA. The term "event" also refers to progeny produced by a sexual outcross between the transformant and another line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. For example, "event MIR604," "MIR604" or "MIR604 event" as used herein, means the original MIR604 transformant and/or progeny of the MIR604 transformant (U.S. Pat. Nos. 7,361,813, 7,897,748, 8,354,519, and 8,884,102, incorporated by references herein).

As used herein, "heterologous" refers to a nucleic acid molecule or nucleotide sequence not naturally associated with a host cell into which it is introduced, that either originates from another species or is from the same species or organism but is modified from either its original form or the form primarily expressed in the cell, including non-naturally occurring multiple copies of a naturally occurring nucleic acid sequence. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g., present in a different copy number, and/or under the control of different regulatory sequences than that found in the native state of the nucleic acid molecule. A nucleic acid sequence can also be heterologous to other nucleic acid sequences with which it may be associated, for example in a nucleic acid construct, such as e.g., an expression vector. As one nonlimiting example, a promoter may be present in a nucleic acid construct in combination with one or more regulatory element and/or coding sequences that do not naturally occur in association with that particular promoter, i.e., they are heterologous to the promoter.

An "isolated" nucleic acid molecule or nucleotide sequence or an "isolated" polypeptide is a nucleic acid molecule, nucleotide sequence or polypeptide that, by the hand of man, exists apart from its native environment and/or has a function that is different, modified, modulated and/or altered as compared to its function in its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid sequence molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid sequence that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid sequence that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

"Wild-type" nucleotide sequence or amino acid sequence refers to a naturally occurring ("native") or endogenous nucleotide sequence or amino acid sequence. Thus, for example, a "wild-type mRNA" is an mRNA that is naturally occurring in or endogenous to the organism.

As used herein, the phrases "operably linked," "operatively linked," "operatively associated" or "in operative association" and the like, mean that elements of a nucleic acid construct such as an expression cassette or nucleic acid molecule are configured so as to perform their usual function. Thus, regulatory or control sequences (e.g., promoters) operatively associated with a nucleotide sequence are capable of effecting expression of the nucleotide sequence. For example, a promoter is operably linked with a coding sequence or functional RNA when it is capable of affecting the expression of that coding sequence or functional RNA (i.e., the coding sequence or functional RNA is under the transcriptional control of the promoter). Coding sequences in sense or antisense orientation can be operably-linked to regulatory sequences. The control sequences need not be contiguous with the nucleotide sequence of interest, as long as they function to direct the expression thereof. Thus, for example, intervening untranslated, yet transcribed, sequences can be present between a promoter and a coding sequence, and the promoter sequence can still be considered "operably linked" to the coding sequence.

"Primers" as used herein are isolated nucleic acids that are annealed to a complementary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other nucleic-acid amplification methods.

A "probe" is an isolated nucleic acid molecule that is complementary to a portion of a target nucleic acid molecule and is typically used to detect and/or quantify the target nucleic acid molecule. Thus, in some embodiments, a probe can be an isolated nucleic acid molecule to which is attached a detectable moiety or reporter molecule, such as a radioactive isotope, ligand, chemiluminescent agent, fluorescence agent or enzyme. Probes according to the present invention can include not only deoxyribonucleic or ribonucleic acids but also polyamides and other probe materials that bind specifically to a target nucleic acid sequence and can be used to detect the presence of and/or quantify the amount of, that target nucleic acid sequence.

A TaqMan probe is designed such that it anneals within a DNA region amplified by a specific set of primers. As the Taq polymerase extends the primer and synthesizes the nascent strand from a single-strand template from 3' to 5' of the complementary strand, the 5' to 3' exonuclease of the polymerase extends the nascent strand through the probe and consequently degrades the probe that has annealed to the template. Degradation of the probe releases the fluorophore from it and breaks the close proximity to the quencher, thus relieving the quenching effect and allowing fluorescence of the fluorophore. Hence, fluorescence detected in the quantitative PCR thermal cycler is directly proportional to the fluorophore released and the amount of DNA template present in the PCR.

Primers and probes are generally between 5 and 100 nucleotides or more in length. In some embodiments, primers and probes can be at least 20 nucleotides or more in length, or at least 25 nucleotides or more, or at least 30 nucleotides or more in length. Such primers and probes hybridize specifically to a target sequence under optimum hybridization conditions as are known in the art. Primers and probes according to the present invention may have complete sequence complementarity with the target sequence, although probes differing from the target sequence and which retain the ability to hybridize to target sequences may be designed by conventional methods according to the invention.

Methods for preparing and using probes and primers are described, for example, in *Molecular Cloning: A Laboratory Manual*, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

The polymerase chain reaction (PCR) is a technique for "amplifying" a particular piece of DNA. In order to perform PCR, at least a portion of the nucleotide sequence of the DNA molecule to be replicated must be known. In general, primers or short oligonucleotides are used that are complementary (e.g., substantially complementary or fully complementary) to the nucleotide sequence at the 3' end of each strand of the DNA to be amplified (known sequence). The DNA sample is heated to separate its strands and is mixed with the primers. The primers hybridize to their complementary sequences in the DNA sample. Synthesis begins (5' to 3' direction) using the original DNA strand as the template. The reaction mixture must contain all four deoxynucleotide triphosphates (dATP, dCTP, dGTP, dTTP) and a DNA polymerase. Polymerization continues until each newly-synthesized strand has proceeded far enough to contain the sequence recognized by the other primer. Once this occurs, two DNA molecules are created that are identical to the original molecule. These two molecules are heated to separate their strands and the process is repeated. Each cycle doubles the number of DNA molecules. Using automated equipment, each cycle of replication can be completed in less than 5 minutes. After 30 cycles, what began as a single molecule of DNA has been amplified into more than a billion copies ($2^{30}=1.02\times10^9$).

The oligonucleotides of an oligonucleotide primer pair are complementary to DNA sequences located on opposite DNA strands and flanking the region to be amplified. The annealed primers hybridize to the newly synthesized DNA strands. The first amplification cycle will result in two new DNA strands whose 5' end is fixed by the position of the oligonucleotide primer but whose 3' end is variable ('ragged' 3' ends). The two new strands can serve in turn as templates for synthesis of complementary strands of the desired length (the 5' ends are defined by the primer and the 3' ends are fixed because synthesis cannot proceed past the terminus of the opposing primer). After a few cycles, the desired fixed length product begins to predominate.

"Detection kit" as used herein refers to a kit used to detect target DNA from the events of interest in a sample comprising nucleic acid probes and primers of the present invention, which will be processed specifically under optimum conditions to a target DNA sequence, and other materials necessary to enable nucleic acid hybridization and/or amplification methods.

As used herein, the terms "transformed" and "transgenic" refer to any plant, plant cell, callus, plant tissue, or plant part that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

The term "transformation" as used herein refers to the transfer of a nucleic acid molecule into the genome of a host cell, resulting in genetically stable inheritance. In some embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or any combination thereof.

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in *Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell Mol Biol Lett* 7:849-858 (2002)).

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. 1993, *Plant Cell* 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hdfgen and Willmitzer 1988, *Nucleic Acids Res* 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle.

Biologically active particles (e.g., dried yeast cells, dried bacteria or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

The term "introducing" or "introduce" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, a transgenic plant cell, plant and/or plant part of the invention can be stably transformed or transiently transformed.

As used herein, "stably introducing," "stably introduced," "stable transformation" or "stably transformed" in the context of a polynucleotide introduced into a cell, means that the introduced polynucleotide is stably integrated into the genome of the cell, and thus the cell is stably transformed with the polynucleotide. As such, the integrated polynucleotide is capable of being inherited by the progeny thereof, more particularly, by the progeny of multiple successive generations. "Genome" as used herein includes the nuclear and/or plastid genome, and therefore includes integration of a polynucleotide into, for example, the chloroplast genome. Stable transformation as used herein can also refer to a polynucleotide that is maintained extrachromasomally, for example, as a minichromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

"Primary transformant" and "TO generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part. Regeneration methods from a transformed plant cell, for example a transformed maize cell, are well-known in the art.

"Transient transformation" in the context of a polynucleotide means that a polynucleotide is introduced into the cell and does not integrate into the genome of the cell.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods. Transformation can also be detected by direct sequencing and/or hybridization protocols well known in the art.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences or protein sequences, refers to two or more sequences or subsequences that have at least about 70%, least about 75%, at least about 80%, least about 85%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of this invention, the substantial identity exists over a region of the sequences that is at least about 50, about 60, about 70, about 80, about 90, about 100, about 110, about 120, about 130, about 140, about 150, or more residues in length. In some particular embodiments, the sequences are substantially identical over at least about 150 residues. In a further embodiment, the sequences are substantially identical over the entire length of the coding regions. Furthermore, in representative embodiments, substantially identical nucleotide or protein sequences perform substantially the same function (e.g., conferring increased resistance to a nematode plant parasite, reducing the growth of a nematode plant parasite, reducing cyst development).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package@(Accelrys Inc., San Diego, CA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2×(or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the present invention. In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M $NaPO_4$, 1 mM EDTA at 50° C. with washing in 1×SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

In the current state of the art, introducing a DNA of interest into a maize cell is typically done using *Agrobacterium*-mediated transformation or biolistic bombardment. These methods rely on the random insertion of the DNA of interest, such as a transgene, into the maize genome. The expression of foreign genes in plants can be influenced by their chromosomal position, for example due to chromatin structure and/or the proximity of transcriptional regulation elements close to the integration site (See for example, Weising et al., 1988, "Foreign Genes in Plants," Ann. Rev. Genet. 22:421-477). A high-quality transgenic event is preferred to not be in a promoter or gene region of the genome. A high-quality transgenic event also must not have negative effects on the agronomic performance of the transgenic plant. Additionally, a high-quality transgenic event is the result of a single, intact, transgene insertion, with little or no transgene rearrangement, and without contamination by extraneous heterologous DNA, such as DNA from the backbone of a vector used during the transformation process. A high-quality transgenic event also is preferred to lack introduced ORFs, which potentially may be expressed in the transgenic plant.

It is common to produce hundreds of different events and screen those events for a single event that has desired molecular qualities and transgene expression levels and patterns for commercial purposes. The identified event which satisfies all criteria required for a high-quality event which may be used for commercial purposes is considered an elite event. The elite event is characterized by its exact genomic location, as it is that location which is responsible for the molecular qualities, transgene expression levels, and agronomic performance of the event. The effort required to identify an elite event is on the scale of a large research program. Therefore, there is a desire in the art for novel, more efficient methods of introducing a DNA of interest into a maize cell to produce a high-quality transgenic event.

The recent development of methods and compositions which make targeted genomic insertion relatively less labor intensive provide a critical piece for the technical solution for improved methods of insertion of heterologous nucleic acids into a genome of interest. The present invention includes ideal genomic locations, or loci, for methods for targeted genomic insertion. Successful targeted insertion into any one of these genomic loci can produce a high-quality transgenic event.

Ideal target sites for genomic modifications, in particular for targeted insertion of a DNA of interest into a maize genome, must satisfy a number of criteria. These desirable genomic target sites may also be referred to as "ideal genomic loci", "target genomic loci", "safe harbor sites", or "safe harbors", and refer to regions of contiguous nucleic acids in the genome that are the selected or preferred site for insertion of a nucleotide sequence of interest (for example, a donor sequence) into the genome. Based on the current knowledge of plant genome organization, gene structure and expression, DNA recombination, genome engineering and GM product regulatory requirements, the following artificially defined criteria were used to identify ideal genomic loci that are suitable for targeted integration and stable expression: (1) regions that contain mostly unique sequences and may be suitable for targeted integration mediated by homologous recombination; (2) regions that are not part of a known functional gene, including those encoding for miRNAs; ideally, these regions should be at least 2 Kb upstream of any known open reading frame or 1 Kb downstream from the 3'-untranslated region (3'-UTR) of a gene, so that integration of a DNA of interest may not interrupt endogenous gene sequences or affect function of neighboring endogenous genes; (3) regions that are not close to heterochromatic regions with highly repetitive sequences such as pericentromeric regions that may result in unstable expression of transgenes or potential silencing of inserted transgenes; (4) regions that do not contain known cis-acting elements such as enhancers or repressors so that transgene expression pattern and level is not altered unexpectedly when inserted; (5) regions that have empirical data showing good transgene expression, if possible. An example of a target maize genomic locus may comprise a nucleic acid sequence of at least 10 nucleotides, at least 20, 25, 30, 40, 50, 60, 70, 75, 80, 90, 100, 150, 200, 250, 300, 250, 400, 450, 500, 600, 700, 800, 900, 1000, 1500, 2000, 2500, 3000, 3500, 4000, 4500, or at least 5000 nucleotides, and have at least 70%, at least 75%, at least 80%, at least 85%, at least 90%, at least 93%, at least 95%, at least 96%, at least 97%, at least 98%, at least 99%, or 100% identity to at least 10 nucleotides, at least 20, 25, 30, 40, 50, 60, 70, 75, 80, 90, 100, 150, 200, 250, 300, 250, 400, 450, 500, 600, 700, 800, 900, 1000, 1500, 2000, 2500, 2750, 2900, or at least 3000 nucleotides of any one of SEQ ID NO: 1-71 or a complement thereof.

Targeting insertion of a DNA of interest into safe harbors identified by this criteria is likely to result in a transgenic plant which has minimal issues regarding stable expression levels. Targeting the DNA of interest to a safe harbor also eliminates significant screening required to identify events produced by random genomic insertion which satisfy the "safe harbor" criteria. Additionally, the identification of safe harbor sites which are highly conserved in more than one maize variety indicates that the safe harbor in one maize variety is likely to be a safe harbor in a different maize variety. This is important for introgression of the DNA of interest into multiple varieties for commercial agricultural use.

As used herein a "DNA of interest", "nucleic acid of interest", or "nucleotide sequence of interest", is defined as a nucleic acid/DNA sequence that has been selected for site directed, targeted insertion into the maize genome. A nucleic acid of interest can be of any length, for example between 2 and 50,000 nucleotides in length (or any integer value there between or there above), preferably between about 1,000 and 5,000 nucleotides in length (or any integer value there between). A DNA of interest may comprise one or more gene expression cassettes that further comprise actively transcribed and/or translated gene sequences. Conversely, the DNA of interest may comprise a polynucleotide sequence which does not comprise a functional gene expression cassette or an entire gene (e.g., may simply comprise regulatory sequences such as a promoter), or may not contain any identifiable gene expression elements or any actively transcribed gene sequence. The DNA of interest may optionally contain an analytical domain, such as a domain that may contain specifically designed restriction enzyme sites, zinc finger binding sites, engineered landing pads, or engineered transgene integration platforms. Upon insertion of the nucleic acid of interest into the maize genome, the inserted sequences may be referred to, for example, as the "inserted DNA of interest". Further, the nucleic acid of interest can be DNA or RNA, can be linear or circular, and can be single-stranded or double-stranded. It can be delivered to the cell as naked nucleic acid, as a complex with one or more delivery agents (e.g., liposomes, poloxamers, T-strand encapsulated with proteins, a Feldan Shuttle (U.S. Patent Publication No. 20160298078, herein incorporated by reference) etc.) or contained in a bacterial or viral delivery vehicle, such as, for example, Agrobacterium tumefaciens or an adenovirus.

A DNA of interest may further comprise a "gene of interest". "Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "donor", "donor molecule", or "donor sequence" as used herein comprises a DNA of interest. The donor molecule may further comprise homologous arms or other nucleic acid sequences useful for recombination of the nucleic acid of interest into the target site of the host genome. The donor sequence may comprise one or more transgenes, expression cassettes, or other nucleotide sequences of interest. A donor molecule may be single stranded, partially double-stranded, or double-stranded. The donor molecule may be a natural or a modified polynucleotide, a RNA-DNA chimera, or a DNA fragment, either single- or at least partially double-stranded, or a fully double-stranded DNA molecule, or a PGR amplified ssDNA or at least partially dsDNA fragment. In some embodiments, the donor DNA molecule is part of a circularized DNA molecule. A fully double-stranded donor DNA is advantageous since it might provide an increased stability, since dsDNA fragments are generally more resistant than ssDNA to nuclease degradation. In some embodiments, the donor polynucleotide molecule can comprise at least about 100, 150, 200, 250, 300, 250, 400, 450, 500, 600, 700, 800, 900, 1000, 1500, 2000, 2500, 3000, 3500, 4000, 4500, 5000, 7500, 10000, 15,000 or at least about 20,000 nucleotides, including any value within this range not explicitly recited herein. In some embodiments, the donor DNA molecule comprises a heterologous nucleic acid sequence. In some embodiments, the donor DNA molecule comprises at least one expression cassette. In some embodiments, the donor DNA molecule may comprise a transgene. In some embodiments, the donor DNA molecule comprises an allelic modification of a gene which is native to the target genome. The allelic modification may comprise at least one nucleotide insertion, at least one nucleotide deletion, and/or at least one nucleotide substitution. In some embodiments, the allelic modification may comprise an INDEL. In some embodiments, the donor DNA molecule comprises at least 50 nucleotides, at least 60, 70, 80, 90, 100, 150, 200, 250, 300, 250, 400, 450, 500, 600, 700, 800, 900, 1000, 1500, 2000, 2500, 3000, 3500, 4000, 4500, 5000, 7500, 10000, 15,000 or at least 20,000 nucleotides, which have at least 70%, at least 75%, at least 80%, at least 85%, at least 90%, at least 93%, at least 95%, at least 96%, at least 97%, at least 98%, at least 99%, or 100% identity to at least 50 contiguous nucleotides, 60, 70, 80, 90, 100, 150, 200, 250, 300, 250, 400, 450, 500, 600, 700, 800, 900, 1000, 1500, 2000, 2500, 2750, 2900, or at least 3000 contiguous nucleotides of SEQ ID NO: 1-71 or a complement thereof, and wherein the donor molecule further comprises a DNA of interest. In some embodiments, the donor DNA molecule comprises at least 100 contiguous nucleotides at least 90% identical to a genomic nucleic acid sequence, and optionally may further comprise a heterologous nucleic acid sequence such as a transgene.

A "homologous" nucleic acid sequence is a nucleic acid sequence naturally associated with a host cell into which it is introduced. A homologous nucleic acid sequence can also be a nucleic acid sequence that is naturally associated with other nucleic acid sequences that may be present, e.g., in a nucleic acid construct. As one nonlimiting example, a promoter may be present in a nucleic acid construct in combination with one or more regulatory elements and/or coding sequences that naturally occur in association with that particular promoter, i.e., they are homologous to the promoter.

In some instances "homologous" may be used to refer to the relationship of a first gene to a second gene by descent from a common ancestral DNA sequence. In such instances, the term "homolog" indicates a relationship between genes separated by the event of speciation (or an "ortholog") or to the relationship between genes separated by the event of genetic duplication (or a "paralog"). In other instances "homologous" may be used to refer to the level of sequence identity between one or more polynucleotide sequences, in such instances the one or more polynucelotide sequences do not necessarily descend from a common ancestral DNA sequence. Those with skill in the art are aware of the interchangeably of the term "homologous" and appreciate the proper application of the term.

Targeted genomic insertion methods of the invention require a site-directed nuclease and a nucleic acid molecule comprising the DNA of insertion as well as at least one homologous arm which is important for homologous recombination of the nucleic acid molecule into the target genomic locus. The target genomic locus comprises a nuclease cleavage site, which may be a targeted site for a site-directed nuclease.

A "nuclease cleavage site" or "genomic nuclease cleavage site" is a region of nucleotides that comprise a nuclease cleavage sequence that is recognized by a specific nuclease, which acts to cleave the nucleotide sequence of the DNA of the genomic nuclease cleavage site in one or both strands. Such cleavage by the nuclease enzyme initiates DNA repair mechanisms within the cell, which establishes an environment for homologous recombination to occur. In the methods herein wherein a first nucleic acid molecule comprises, for example, at least about 100 contiguous nucleotides having, for example, at least 90% identity with a target site in the genome of the cell, the first nucleic acid molecule may be integrated into the genome of the cell via homologous recombination, thereby integrating the one or more DNAs of interest into the genome of the cell.

The term "cleavage" or "cleaving" refers to breaking of the covalent phosphodiester linkage in the ribosylphosphodiester backbone of a polynucleotide. The terms "cleavage" or "cleaving" encompass both single-stranded breaks and double-stranded breaks. Double-stranded cleavage can occur as a result of two distinct single-stranded cleavage events. Cleavage can result in the production of either blunt ends or staggered ends.

The nuclease of the methods of the invention may be engineered to target the nucleic acid sequence of the genomic nuclease cleavage site. In some embodiments, the genomic nuclease cleavage site may be unique to the maize genome. In other embodiments, the genomic nuclease cleavage site may occur infrequently in the maize genome. "Infrequently" may be less than 500 occurrences, less than 400, 300, 200, 100, 90, 80, 70, 60, 50, 40, 30, 20, 10, 5, or less than 3 occurrences in the maize genome.

In some embodiments, the nuclease in the methods of the invention may be a site specific nuclease, such a meganuclease, a zinc finger nuclease, a TALEN, or a CRISPR-associated nuclease. In some embodiments, the meganuclease is a homing endonuclease, for example I-SceI or I-CreI. In some embodiments, the CRISPR-associated nuclease is a Cas9, Cpf1, or dCas9 ("dead" Cas9) or dCpf1 ("dead" Cpf1). For the "dead" CRISPR-associated nuclease, the nuclease activity of the RNA binding protein is inactivated.

In some embodiments, the site specific nuclease is a TALEN or a zinc finger nuclease. In some embodiments, the TALEN or zinc finger nuclease may be chimeric. The TALEN and/or zinc finger nuclease may bind to the maize genomic target site and cleave the maize genomic target site, where upon the DNA of interest integrates within or proximal to the maize genomic target site. In an embodiment, integration of the DNA of interest occurs within the maize genomic target site may result in rearrangements. In some embodiments, the rearrangements may comprise deletions, insertions, inversions, and repeats. In one embodiment, integration of the DNA of interest may occur proximal to the maize genomic target site. According to an aspect of the embodiment, the integration site of the DNA of interest is proximal to the target maize genomic locu, and may integrate within 1.5 Kb, 1.25 Kb, 1.0 Kb, 0.75 Kb, 0.5 Kb, 0.25 Kb, 0.15 Kb, 0.10 Kb, 50 bp, 25 bp, 10 bp, or within 5 bp to the maize genomic target site. Insertion within a genomic region proximal to the maize genomic target site is known in the art, see for example for zinc finger nucleases US Patent Pub No. 2010/0257 638 A1 (herein incorporated by reference in its entirety). As used herein, the terms "adjacent" or "adjacent to" with regard to one or more nucleotide sequences of this invention means immediately next to (e.g., with no intervening sequence) or separated by from about 1 base to about 1,000 bases (e.g., 1, 2, 3, 4, 5, 6, 7, 8, 9, 10, 15, 20, 30, 40, 50, 100, 200, 500, or 1,000 bases), including any values included within this range but not explicitly recited herein.

Zinc finger, meganuclease, and TALE DNA binding domains can be "engineered" to bind to a predetermined nucleotide sequence, for example via engineering (altering one or more amino acids) of the recognition helix region of a naturally occurring zinc finger. Similarly, TALENs and meganucleases can be "engineered" to bind to a predetermined nucleotide sequence, for example by engineering of the amino acids involved in DNA binding (for example, the repeat variable diresidue or RVD region in a TALEN). Therefore, engineered DNA binding proteins (zinc fingers, meganucleases, or TALENs) are proteins that are non-naturally occurring.

Non-limiting examples of methods for engineering DNA-binding proteins are design and selection. A designed DNA binding protein is a protein not occurring in nature whose design/composition results primarily from rational criteria. Rational criteria for design include application of substitution rules and computerized algorithms for processing information. Such rational criteria can be applied for the design of zinc fingers, TALENs, meganucleases, or CRISPR-associated nucleases. See, for example, U.S. Pat. Nos. 6,140,081, 6,453,242, 6,534,261; see also WO 98/53058; WO98/53059; WO 98/53060; WO 02/016536 and WO03/016496 and U.S. Publication Nos. 20110301073, 20110239315 and 20119145940. A "selected" zinc finger protein, CRISPR-associated nuclease, meganuclease, or TALEN is a protein not found in nature whose production results primarily from an empirical process such as phage display, interaction trap or hybrid selection. See e.g., WO 96/06166; WO 98/53057;

WO 98/54311; WO00/27878; WO 01/60970 WO 01/88197 and WO 02/099084 and U.S. Publication Nos. 20110301073, 20110239315 and 20119145940.

In some embodiments, the DNA-binding domain is an engineered domain from a TAL effector derived from the plant pathogen *Xanthomonas* (see, Miller et al. (2011) Nature Biotechnology 29(2):143-8; Boch et al, (2009) Science 29 Oct. 2009 (10.1 126/science.117881) and Moscou and Bogdanove, (2009) Science 29 Oct. 2009 (10.1126/science.1178817; and U.S. Patent Publication Nos. 20110239315, 20110145940 and 20110301073).

In some embodiments, the DNA-binding domain may be associated with a cleavage (nuclease) domain. For example, homing endonucleases may be modified in their DNA-binding specificity while retaining nuclease function. In addition, zinc finger proteins may also be fused to a cleavage domain to form a zinc finger nuclease. The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., Sl Nuclease; mung bean nuclease; pancreatic DNase I; micrococcal nuclease; yeast HO endonuclease; see also Linn et al. (eds.) Nucleases, Cold Spring Harbor Laboratory Press, 1993). Non limiting examples of homing endonucleases and meganucleases include I-SceI, I-Ceul, PI-Pspl, PI-See, I-SceIV, I-Csml, I-PanI, I-Scell, I-PpoI, I-ScellI, I-CreI-TevI, I-TevII and I-TevIII. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263: 163-180; Argast et al. (1998) J. Mol. Biol. 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites proximal to the recognition site and have separable binding and cleavage domains. For example, the Type IIS enzyme Fokl catalyzes double stranded cleavage of DNA at 9 nucleotides from its recognition site on one strand and 13 nucleotides from its recognition site on the other. See, for example, U.S. Pat. Nos. 5,356,802, 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins may comprise the cleavage domain (or cleavage half domain) from at least one Type IIS restriction enzyme and one or more zinc finger binding domains, which may or may not be engineered. An exemplary Type IIS restriction enzyme, whose cleavage domain is separable from the binding domain, is Fokl. This particular enzyme is active as a dimer (Bitinaite et al. (1998) Proc. Natl. Acad. Sci. USA 95: 10,570-10,575). Accordingly, for the purposes of the present disclosure, the portion of the Fokl enzyme used in the disclosed fusion proteins is considered a cleavage half-domain. A cleavage domain or cleavage half-domain can be any portion of a protein that retains cleavage activity, or that retains the ability to multimerize (e.g., dimerize) to form a functional cleavage domain. Exemplary Type IIS restriction enzymes are described in International Publication WO 2007 I014275, incorporated by reference herein in its entirety. To enhance cleavage specificity, cleavage domains may also be modified. Non-limiting examples of modified cleavage half-domains are described in detail in WO 2007/014275, incorporated by reference in its entirety herein. In certain embodiments, the cleavage domain comprises an engineered cleavage half-domain (also referred to as dimerization domain mutants) that minimize or prevent homodimerization. Such embodiments are known to those of skill the art and described for example in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496,498, 499, 500, 531, 534, 537, and 538 of FokI are all targets for influencing dimerization of the Fokl cleavage half-domains.

The term "CRISPR-associated protein", "Cas protein", "CRIPSR-associated nuclease" or "Cas nuclease" refers to a wild type Cas protein, a fragment thereof, or a mutant or variant thereof. The term "Cas mutant" or "Cas variant" refers to a protein or polypeptide derivative of a wild type Cas protein, e.g., a protein having one or more point mutations, insertions, deletions, truncations, a fusion protein, or a combination thereof. In certain embodiments, the Cas mutant or Cas variant substantially retains the nuclease activity of the Cas protein, such as a Cas9 variant described herein which is operably linked to a nuclear localization signal (NLS) derived from a plant. In certain embodiments, the Cas nuclease is mutated such that one or both nuclease domains are inactive, such as, for example, a catalytically dead Cas9 referred to as dCas9, which is still able to target to a specific genomic location but has no endonuclease activity (Qi et al., 2013, Cell, 152: 1173-1183, hereby incorporated within). In some embodiments, the Cas nuclease is mutated so that it lacks some or all of the nuclease activity of its wild-type counterpart. The Cas protein may be Cas9, Cpf1 (Zetsche et al., 2015, Cell, 163: 759-771, hereby incorporated within) or another CRISPR-associated nuclease.

As used herein, the term "guide RNA" or "gRNA" generally refers to an RNA molecule (or a group of RNA molecules collectively) that can bind to a Cas protein and aid in targeting the Cas protein to a specific location within a target polynucleotide (e.g., a DNA). A guide RNA can comprise a crRNA segment and/or a tracrRNA. The present invention further provides a guide RNA of the invention comprising a tracrRNA, wherein the tracrRNA comprises a nucleic acid sequence that is capable of binding to protein. A guide RNA of the invention also encompasses an engineered chimeric single guide RNA (sgRNA), where the crRNA segment and the tracrRNA segment are located in the same RNA molecule. A "guide RNA" also encompasses, collectively, a group of two ("dual guide RNA") or more RNA molecules, where the crRNA segment and the tracrRNA segment are located in separate RNA molecules. As used herein, the term "crRNA" or "crRNA segment" refers to an RNA molecule or portion thereof that includes a polynucleotide targeting guide sequence, a stem sequence, and, optionally, a 5'-overhang sequence. As used herein, the term "tracrRNA" or "tracrRNA segment" refers to an RNA molecule or portion thereof that includes a protein-binding segment (e.g., the protein-binding segment is capable of interacting with a CRISPR-associated protein, such as a Cas9). The present invention further provides an engineered guide RNA comprising a chimeric crRNA segment comprising a guide RNA sequence capable of hybridizing to a genomic target sequence, a CRISPR repeat sequence and a bait RNA segment capable of hybridizing to a donor DNA molecule. In some embodiments, the guide RNA, either as a sgRNA or as two or more RNA molecules, does not contain a tracrRNA, as it is known in the art that some CRISPR-associated nucleases, such as Cpf1, do not require a tracrRNA for its RNA-mediated endonuclease activity (Qi et al., 2013).

The present invention also provides methods which include a nucleic acid molecule comprising a nucleic acid sequence encoding a guide RNA of the invention. The nucleic acid molecule may be a DNA or an RNA molecule. In some embodiments, the nucleic acid molecule is circularized. In other embodiments, the nucleic acid molecule is linear. In some embodiments, the nucleic acid molecule is single stranded, partially double-stranded, or double-stranded. In some embodiments, the nucleic acid molecule is complexed with at least one polypeptide. In some embodiments, the polypeptide is a carrier protein for mediating delivery of, for example, the guide RNA, a nuclease, and optionally a donor molecule. In some embodiments, the polypeptide is a Feldan Shuttle (U.S. Patent Publication No. 20160298078, herein incorporated by reference). The nucleic acid molecule may comprise an expression cassette capable of driving the expression of the guide RNA. The nucleic acid molecule may further comprise additional expression cassettes, capable of expressing, for example, a nuclease such as a CRISPR-associated nuclease.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the nucleotide sequence that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide. For HR-directed integration, the donor molecule contains at least 1, typically at least 2 regions of homology to the genome ("homology arms") of least 50-100 base pairs in length. See, e.g., U.S. Pat. No. 9,045,763. In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break for HR mediated integration or having no homology to the nucleotide sequence in the region of the break for NHEJ mediated integration, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another. In any of the methods described herein, additional zinc-finger proteins, meganucleases, CRISPR-associated nucleases, or TALENs can be used for additional double-stranded cleavage of additional target sites within the cell.

Accordingly, the present invention provides a maize recombinant polynucleotide, wherein the recombinant polynucleotide comprises a nucleic acid sequence of at least 50 nucleotides, at least 60, 70, 80, 90, 100, 150, 200, 250, 300, 250, 400, 450, 500, 600, 700, 800, 900, 1000, 1500, 2000, 2500, 3000, 3500, 4000, 4500, 5000, 7500, 10000, 15,000 or at least 20,000 nucleotides, and has at least 70%, at least 75%, at least 80%, at least 85%, at least 90%, at least 93%, at least 95%, at least 96%, at least 97%, at least 98%, at least 99%, or 100% identity to at least 50 contiguous nucleotides, 60, 70, 80, 90, 100, 150, 200, 250, 300, 250, 400, 450, 500, 600, 700, 800, 900, 1000, 1500, 2000, 2500, 2750, 2900, or at least 3000 contiguous nucleotides of SEQ ID NO: 1-71 or a complement thereof, and wherein the recombinant polynucleotide further comprises a DNA of interest, wherein the DNA of interest is inserted into the nucleic acid sequence to produce said recombinant polynucleotide.

In further embodiments, the recombinant polynucleotide comprises a DNA of interest inserted proximal to a nuclease cleavage site within the recombinant polynucleotide.

In some embodiments, the recombinant polynucleotide comprises a DNA of interest which is a transgene. In some embodiments, the DNA of interest comprises at least one gene of interest. In some embodiments, the DNA of interest comprises at least one expression cassette. In some embodiments, the DNA of interest comprises two or more expression cassettes. In some embodiments, the DNA of interest does not encode a polypeptide. In some embodiments, the DNA of interest comprises regulatory sequences.

In some embodiments, the recombinant polynucleotide comprises a nucleic acid sequence of at least 50 nucleotides, at least 60, 70, 80, 90, 100, 150, 200, 250, 300, 250, 400, 450, 500, 600, 700, 800, 900, 1000, 1500, 2000, 2500, 3000, 3500, 4000, 4500, 5000, 7500, 10000, 15,000 or at least 20,000 nucleotides, and has at least 70%, at least 75%, at least 80%, at least 85%, at least 90%, at least 93%, at least 95%, at least 96%, at least 97%, at least 98%, at least 99%, or 100% identity to at least 50 contiguous nucleotides, at least 60, 70, 80, 90, 100, 150, 200, 250, 300, 250, 400, 450, 500, 600, 700, 800, 900, 1000, 1500, 2000, 2500, 2750, 2900, or at least 3000 contiguous nucleotides of SEQ ID NO: 1, 8, 9, 13, 21, 22, 23, 31, 37, 39, 40, 44, 46, 55, 56, 57, 62-71, or a complement thereof.

The present invention also provides a maize plant, plant part, or plant cell comprising the recombinant polynucleotide described above.

In another embodiment, the present invention provides a method of integrating a DNA of interest into a target maize genomic locus in a maize genome, wherein the target maize genomic locus comprises a nucleic acid sequence of at least 50, at least 60, at least 70, at least 80, at least 90, at least 100, at least 110, at least 120, at least 130, at least 140, at least 150, 200, 250, 300, 250, 400, 450, 500, 600, 700, 800, 900, 1000, 1500, 2000, 2500, 2750, 2900, or at least 3000 contiguous nucleotides having at least 70%, at least 75%, at least 80%, at least 85%, at least 90%, at least 93%, at least 95%, at least 96%, at least 97%, at least 98%, at least 99%, or 100% identity to at least 50 contiguous nucleotides, at least 60, at least 70, at least 80, at least 90, at least 100, at least 110, at least 120, at least 130, at least 140, at least 150, 200, 250, 300, 250, 400, 450, 500, 600, 700, 800, 900, 1000, 1500, 2000, 2500, 2750, 2900, or at least 3000 contiguous nucleotides of SEQ ID NO: 1 through SEQ ID NO: 71, or a complement thereof, comprising introducing into a maize cell: (a) a first nucleic acid molecule comprising at least 50, at least 60, at least 70, at least 80, at least 90, at least 100, at least 110, at least 120, at least 130, at least 140, or at least 150 contiguous nucleotides, wherein said contiguous nucleotides have at least 70%, at least 75%, at least 80%, at least 85%, at least 90%, at least 93%, at least 95%, at least 96%, at least 97%, at least 98%, at least 99%, or 100% identity to at least a 50, at least 60, at least 70, at least 80, at least 90, at least 100, at least 110, at least 120, at least 130, at least 140, or at least a 150 contiguous nucleotides of SEQ ID NO: 1 through SEQ ID NO: 71, or a complement thereof, and further comprising a DNA of interest; and (b) a second nucleic acid molecule comprising a nucleotide sequence encoding a nuclease for site-directed cleavage at a genomic nuclease cleavage site of, adjacent to, or proximal to the genomic nucleotide sequence of SEQ ID NO: 1 through SEQ ID NO: 71, or a complement thereof, that corresponds to the contiguous nucleotides of (a), under conditions wherein expression of the second nucleic acid molecule can occur to produce the nuclease and the nuclease can cleave the nucleotide sequence at the genomic nuclease cleavage site, whereby the DNA of interest is integrated at the genomic nuclease target cleavage site in the maize genome.

In some embodiments of the above method, the first nucleic acid molecule can comprise at least about 100, 150, 200, 250, 300, 250, 400, 450, 500, 600, 700, 800, 900, 1000, 1500, 2000, 2500, 3000, 3500, 4000, 4500, 5000, 7500, 10000, 15,000 or 20,000 nucleotides, including any value within this range not explicitly recited herein.

In some embodiments, the first nucleic acid molecule and the second nucleic acid molecule can be introduced into the maize cell by biolistic nucleic acid delivery, via an *Agrobacterium*, by co-transformation, and/or with a T-DNA vector in any combination and/or order.

In some embodiments, the first nucleic acid molecule and the second nucleic acid molecule can be present on a single nucleic acid construct and in some embodiments, the first nucleic acid molecule and the second nucleic acid molecule can be present on separate nucleic acid constructs.

In some embodiments, the first nucleic acid molecule and/or the second nucleic acid molecule can be transiently expressed in the maize cell. In some embodiments, the first nucleic acid molecule and/or the second nucleic acid molecule can be stably integrated into the maize genome of the maize cell.

In some embodiments of the methods of the invention, the first nucleic acid molecule is a donor molecule. In some embodiments, the DNA of interest comprises at least one expression cassette. In some embodiments, the DNA of interest comprises a transgene.

In another embodiment, the present invention provides a method of making a maize plant cell comprising a DNA of interest, said method comprising: (a) selecting a target maize genomic locus, wherein the target maize genomic locus comprises a nucleic acid sequence of at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides, and has at least 70%, at least 75%, at least 80%, at least 85%, at least 90%, at least 93%, at least 95%, at least 96%, at least 97%, at least 98%, at least 99%, or 100% identity to at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides of SEQ ID NO: 1-71 or a complement thereof; (b) selecting a site specific nuclease that specifically binds to and cleaves a genomic nuclease cleavage site within said target maize genomic locus; (c) introducing said site specific nuclease and a DNA of interest into the maize plant cell; (d) allowing the DNA of interest to insert into the target maize genomic locus; and (e) selecting maize plant cells that comprise the DNA of interest inserted into the target maize genomic locus.

The site specific nuclease of the method described above may be introduced into the maize plant cell either as a polypeptide or as nucleic acid molecule, which is transcribed and/or translated in the plant cell to produce the site specific nuclease. The site specific nuclease may be transiently expressed in the plant cell. The site specific nuclease may not be expressed in the maize cell, and may only be present in the maize cell as an active nuclease. The site specific nuclease and the DNA of interest may be introduced into the cell simultaneously or not simultaneously.

In some embodiments of the methods of the invention, the genomic nuclease cleavage site is within a target maize genomic locus which comprises a nucleic acid sequence of at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides, and has at least 70%, at least 75%, at least 80%, at least 85%, at least 90%, at least 93%, at least 95%, at least 96%, at least 97%, at least 98%, at least 99%, or 100% identity to at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides of SEQ ID NO: 1, 8, 9, 13, 21, 22, 23, 31, 37, 39, 40, 44, 46, 55, 56, 57, 62-71, or the complement thereof.

In some embodiments of the methods of the invention, the DNA of interest is inserted into the target maize genomic locus via homologous recombination. In other embodiments, the DNA of interest inserted into the target maize genomic locus via non-homologous end-joining. In some embodiments, the DNA of interest and/or the target maize genomic locus are modified during insertion of said DNA of interest into said target maize genomic locus.

In some embodiments of the methods of the invention, two or more DNAs of interest are inserted into two or more target maize genomic loci by any one of the methods described herein.

In some embodiments of the methods of the invention, the DNA of interest comprises at least one expression cassette. In some embodiments, the DNA of interest comprises a transgene. In some embodiments of the methods of the invention, the DNA of interest does not encode for a polypeptide. In some embodiments of the methods of the invention, the DNA of interest encodes for regulatory sequences.

In some embodiments of the methods of the invention, the site specific nuclease is a CRISPR-associated nuclease, a zinc finger nuclease, a TALEN, or a meganuclease, singly or in combination.

In some embodiments of the methods of the invention, the maize plant cell comprising the target maize genomic locus is transgenic, such that it contains a heterologous sequence in its genome prior to the practice of the method.

In some embodiments of the methods of the invention, the site specific nuclease is a CRISPR-associated nuclease, such as Cas9, and the method includes an additional nucleic acid molecule encoding a guide RNA, which is also introduced into the maize cell. The additional nucleic acid molecule may be a DNA molecule that can be expressed in the maize cell to produce the guide RNA, or it may be an RNA molecule, the guide RNA molecule itself, which is introduced into the maize cell.

In some embodiments, methods of integrating a DNA of interest into a target maize genomic locus comprise a nucleic acid molecule which is a donor molecule. The donor molecule may be a donor vector. The donor molecule may be part of the CRISPR-Cas nuclease system. The nucleic acid sequence of the donor molecule may comprise a DNA of interest and also one or more regions that share homology with the targeted genomic locus. Generally, the homologous region(s) of the donor molecule will have at least 50% sequence identity to a genomic sequence with which recombination is desired. In certain embodiments, the homologous region(s) of the nucleic acid of interest shares at least 70%, at least 75%, at least 80%, at least 85%, at least 90%, at least 95%, at least 96%, at least 97%, at least 98%, at least 99%, or 100% sequence identity with sequences located in the targeted genomic locus. However, any value between 1% and 100% sequence identity can be present, depending upon the length of the nucleic acid of interest. A DNA of interest can contain several, discontinuous regions of sequence sharing relatively high sequence identity to cellular chromatin. For example, for targeted insertion of sequences not normally present in a targeted genomic locus, the unique sequences which comprise the DNA of interest can be present in a donor nucleic acid molecule and flanked by regions of sequences that share a relatively high sequence identity to a sequence present in the targeted genomic locus.

In some embodiments, a donor nucleic acid molecule, which comprises a DNA of interest, is introduced into a host cell for targeted insertion into a safe harbor site in the genome, wherein the donor molecule also comprises homologous flanking sequences on one or both ends of the nucleic acid of interest. In such an embodiment, the homologous flanking sequences contain sufficient levels of sequence identity to a maize genomic sequence to support homologous recombination between it and the genomic sequence to which it bears homology. Approximately 25, 50, 100, 200, 500, 750, 1000, 1500, or 2000 nucleotides, with sequence identity of at least 70%, at least 75%, at least 80%, at least 85%, at least 90%, at least 95%, at least 96%, at least 97%, at least 98%, at least 99%, or 100%, between a donor and a genomic sequence will support homologous recombination there between.

In other embodiments of targeted recombination and/or replacement and/or alteration of genomic sequence at the safe harbor, the genomic sequence is altered by homologous recombination with the donor molecule. Such homologous recombination is stimulated by the presence of a double-stranded break in cellular chromatin, if sequences homologous to the region of the break are present. Double-strand breaks in cellular chromatin can also stimulate cellular mechanisms of non-homologous end-joining. In any of the methods described herein, the donor molecule can contain sequences that are homologous, but not identical, to genomic sequences in the safe harbor, thereby stimulating homologous recombination to insert a non-identical sequence in the safe harbor. Thus, in certain embodiments, portions of the donor molecule that are homologous to sequences in the safe harbor exhibit at least 70%, at least 75%, at least 80%, at least 85%, at least 90%, at least 95%, at least 96%, at least 97%, at least 98%, at least 99%, or 100% sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the safe harbor, such that new sequences are introduced into the safe harbor. In these instances, the non-homologous sequence is generally flanked by sequences of 50 to 2,000 base pairs (or any integral value there between) or any number of base pairs greater than 2,000, that are homologous or identical to sequences in the region of interest. In other embodiments, the donor sequence is non-homologous to the region of interest, and is inserted into the genome for example by non-homologous end-joining. In some embodiments, the sequence of the genomic safe harbor site and/or of the nucleic acid sequence of interest is altered by either the homologous recombination or the non-homologous end-joining. Such alterations may be, for example, the insertion and/or deletion of nucleic acids.

The donor molecule comprising the DNA of interest may be a linear or a circularized molecule. In some embodiments, the donor molecule is circularized and is preferably linearized in vivo by a nuclease, for example one or more of the same or different nucleases that are used to introduce the double-stranded break in the genomic safe harbor site. Synchronized cleavage of the chromosome and the donor molecule in the cell may limit donor DNA degradation (as compared to linearization of the donor molecule prior to introduction into the cell). The nuclease target sites used for linearization of the donor preferably do not disrupt the transgene(s) sequence(s). The transgene may be integrated into the genome in the direction expected by simple ligation of the nuclease overhangs (designated "forward" or "AB" orientation) or in the alternate direction (designated "reverse" or "BA" orientation). In certain embodiments, the transgene is integrated following accurate ligation of the donor and chromosome overhangs. In other embodiments, integration of the transgene in either the BA or AB orientation results in insertion and/or deletion of several nucleotides.

In some embodiments of the methods of the invention, the DNA of interest is integrated into the targeted genomic site of the host cell. In the case of multicellular species, such as maize, transgenic cells may be regenerated into maize callus, a maize plant part, or a maize plant. In some embodiments, the transgenic cell may be cultured to produce a transgenic plant, for example, comprising one or more DNA sequences of interest at one or more safe harbor sites in the genome of the transgenic plant.

The present invention further provides a method of producing a maize plant, plant part, or progeny thereof comprising a DNA of interest, such as a transgene, integrated into the genomic nuclease cleavage site in the maize genome, comprising regenerating a maize plant from the maize cell produced by the method described herein.

Accordingly, the present invention provides a maize plant, plant part, or progeny thereof comprising the transgene integrated into the genomic nuclease cleavage site in the maize genome, produced by the method of this invention.

In some embodiments of the methods described above, the mutation comprises at least one nucleotide substitution, the deletion of at least one nucleotide, or a combination of substitution, deletion, and/or insertion, such as for example an INDEL.

In some embodiments of the methods described above, the nuclease for site-directed cleavage is a non-engineered nuclease. In some embodiments, the nuclease is an engineered nuclease with programmable cleavage target specificity. In some embodiments, the nuclease is a Cas9.

The present invention additionally provides a method of producing a plant, plant part, or progeny thereof comprising a transgene introduced at a nuclease cleavage site in a genome of a plant cell and lacking integration of a heterologous nucleotide sequence encoding a nuclease for site-directed cleavage of a nucleotide sequence at the nuclease cleavage site in the genome of the plant cell, comprising: a) introducing into the plant cell a nucleic acid molecule comprising a heterologous nucleotide sequence encoding a nuclease for site-directed cleavage of the nucleotide sequence at the nuclease cleavage site in the genome of the plant cell under conditions wherein expression of the nucleic acid molecule occurs transiently to produce the nuclease and the nuclease can cleave the nucleotide sequence at the nuclease cleavage site in the genome of the plant cell, thereby introducing a mutation at the nuclease cleavage site in the genome of the plant cell without integration of the heterologous nucleotide sequence encoding the nuclease into the genome of the plant cell; and b) regenerating a plant, plant part, or progeny thereof from the plant cell of (a). The nuclease cleavage site described above is located within a target genomic locus, which comprises a nucleic acid sequence of at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides, and has at least 70%, at least 75%, at least 80%, at least 85%, at least 90%, at least 93%, at least 95%, at least 96%, at least 97%, at least 98%, at least 99%, or 100% identity to at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides of SEQ ID NO: 1-71 or a complement thereof. In another embodiment, the present invention provides for the plant cell produced by the method described above. In a further embodiment, the present invention provides for a plant or plant part regenerated or derived from the plant cell produced by the method described above.

In some embodiments of the method described above, the transgene may comprise at least one, at least two, at least three, at least four, at least five, at least six, at least seven, at least eight, at least nine, at least ten, or ten or more expression cassettes.

In some embodiments of the methods described above, a second nucleic acid molecule comprising a DNA of interest is also introduced into the plant cell. In some embodiments of the methods described above, the first nucleic acid molecule and the second nucleic acid molecule are introduced at the same time, for example by co-transformation, biolistic nucleic acid delivery, or Agrobacterium-mediated transformation. In some embodiments, the first nucleic acid molecule and the second nucleic acid molecule are separate molecules. In some embodiments, a single nucleic acid molecule or construct comprises the first nucleic acid molecule and the second nucleic acid molecule described above.

In some embodiments of the methods described above, the nuclease for site-directed cleavage is a non-engineered nuclease. In some embodiments, the nuclease is an engineered nuclease with programmable cleavage target specificity. In some embodiments, the nuclease is a meganuclease, a TALEN, a zinc finger nuclease, or a CRISPR-associated nuclease, such as Cas9.

The present invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1: Identification of Candidate Safe Harbor Sites in the Maize Genome

Syngenta elite inbred maize line AX5707 was sequenced and assembled using methods known in the art. The assembled reference genome was annotated using the computer software program MAKER (Cantarel et al. 2008, MAKER: An easy-to-use annotation pipeline designed for emerging model organism genomes. *Genome Research.* 18(1):188-196. doi:10.1101/gr.6743907), AX5707 mRNA-SEQ data, and information on plant proteins publicly available from Genbank. Sequences intervals which met certain criteria were selected as potential safe harbors for targeted insertion of a DNA of interest. These criteria including: 1) they do not encode genes including predicted gene models, co-localize with mapped RNA-SEQ data or protein coding sequences; 2) they do not encode smRNAs; 3) they are not repeated in the reference genome; 4) they are ≥1,500 bps; 5) they are ≥2,000 bps away from the nearest identified features such as gene models. 61 sequence intervals were identified. (Table 1). The genomic start and stop positions are as identified on the AX5707 reference genome, referred to as MAIZE_JHAX_REG_5. These candidate safe harbor sites were identified as ideal locations in the maize genome for targeted insertion, and may also be referred to as target maize genomic loci for targeted insertion of a DNA of interest.

TABLE 1

Candidate safe harbor sequence intervals in the AX5707 genome

| Chromosome No. | Genome start position | Genome end position | Length (bp) | SEQ. ID. NO: |
|---|---|---|---|---|
| Chr_1 | 6,051,580 | 6,053,351 | 1,772 | 1 |
| Chr_1 | 9,302,205 | 9,300,245 | 1,961 | 2 |
| Chr_1 | 49,377,512 | 49,375,750 | 1,763 | 3 |
| Chr_1 | 230,909,826 | 230,911,851 | 2,026 | 4 |
| Chr_1 | 233,264,403 | 233,267,221 | 2,819 | 5 |
| Chr_1 | 240,799,470 | 240,801,585 | 2,116 | 6 |
| Chr_1 | 308,952,173 | 308,950,540 | 1,634 | 7 |
| Chr_1 | 325,437,387 | 325,434,968 | 2,420 | 8 |
| Chr_2 | 25,144,470 | 25,146,195 | 1,726 | 9 |
| Chr_2 | 75,055,711 | 75,053,789 | 1,923 | 10 |
| Chr_2 | 76,900,194 | 76,901,853 | 1,660 | 11 |
| Chr_3 | 12,722,668 | 12,724,219 | 1,552 | 12 |
| Chr_3 | 15,938,135 | 15,936,500 | 1,636 | 13 |
| Chr_3 | 58,267,137 | 58,265,554 | 1,584 | 14 |
| Chr_3 | 144,608,280 | 144,610,055 | 1,776 | 15 |
| Chr_3 | 168,663,077 | 168,661,053 | 2,025 | 16 |

TABLE 1-continued

Candidate safe harbor sequence intervals in the AX5707 genome

| Chromosome No. | Genome start position | Genome end position | Length (bp) | SEQ. ID. NO: |
|---|---|---|---|---|
| Chr_3 | 187,169,278 | 187,171,380 | 2,103 | 17 |
| Chr_3 | 192,200,564 | 192,199,030 | 1,535 | 18 |
| Chr_3 | 194,535,751 | 194,533,809 | 1,943 | 19 |
| Chr_3 | 199,586,759 | 199,588,327 | 1,569 | 20 |
| Chr_3 | 263,100,502 | 263,098,753 | 1,750 | 21 |
| Chr_4 | 11,109,020 | 11,107,079 | 1,942 | 22 |
| Chr_4 | 11,850,583 | 11,852,381 | 1,574 | 23 |
| Chr_4 | 28,740,222 | 28,741,822 | 1,601 | 24 |
| Chr_4 | 41,128,134 | 41,125,263 | 2,872 | 25 |
| Chr_4 | 122,196,154 | 122,198,795 | 2,642 | 26 |
| Chr_4 | 225,424,622 | 225,422,966 | 1,657 | 27 |
| Chr_4 | 241,199,476 | 241,201,387 | 1,912 | 28 |
| Chr_4 | 241,203,112 | 241,204,386 | 1,275 | 29 |
| Chr_4 | 260,439,892 | 260,441,993 | 2,102 | 30 |
| Chr_5 | 31,399,845 | 31,397,479 | 2,367 | 31 |
| Chr_5 | 52,271,003 | 52,269,062 | 1,942 | 32 |
| Chr_5 | 61,967,477 | 61,969,470 | 1,994 | 33 |
| Chr_5 | 106,828,555 | 106,826,658 | 1,898 | 34 |
| Chr_5 | 194,229,496 | 194,227,080 | 2,417 | 35 |
| Chr_5 | 227,918,248 | 227,916,660 | 1,589 | 36 |
| Chr_5 | 249,991,940 | 249,989,642 | 2,299 | 37 |
| Chr_5 | 254,507,410 | 254,510,012 | 2,603 | 38 |
| Chr_6 | 2,550,820 | 2,549,212 | 1,609 | 39 |
| Chr_6 | 5,357,797 | 5,356,004 | 1,794 | 40 |
| Chr_6 | 102,854,792 | 102,856,689 | 1,898 | 41 |
| Chr_6 | 125,539,340 | 125,536,747 | 2,594 | 42 |
| Chr_6 | 140,569,284 | 140,567,471 | 1,814 | 43 |
| Chr_6 | 172,684,264 | 172,686,334 | 2,071 | 44 |
| Chr_7 | 6,130,641 | 6,133,196 | 2,556 | 45 |
| Chr_7 | 22,848,628 | 22,850,204 | 1,577 | 46 |
| Chr_7 | 92,523,693 | 92,521,688 | 2,006 | 47 |
| Chr_7 | 123,048,334 | 123,046,540 | 1,795 | 48 |
| Chr_7 | 129,393,722 | 129,390,033 | 3,690 | 49 |
| Chr_7 | 143,964,001 | 143,965,742 | 1,742 | 50 |
| Chr_7 | 145,353,967 | 145,352,332 | 1,636 | 51 |
| Chr_7 | 154,264,096 | 154,267,032 | 2,937 | 52 |
| Chr_7 | 172,566,096 | 172,564,156 | 1,941 | 53 |
| Chr_7 | 179,903,048 | 179,901,489 | 1,560 | 54 |
| Chr_7 | 198,992,304 | 198,994,416 | 2,113 | 55 |
| Chr_8 | 30,777,043 | 30,778,622 | 1,580 | 56 |
| Chr_8 | 210,893,628 | 210,891,662 | 1,967 | 57 |
| Chr_9 | 90,581,099 | 90,582,704 | 1,606 | 58 |
| Chr_9 | 137,742,555 | 137,739,791 | 2,765 | 59 |
| Chr_10 | 18,312,696 | 18,314,420 | 1,725 | 60 |
| Chr_10 | 174,905,414 | 174,903,831 | 1,584 | 61 |

Example 2: Selection of Candidate Maize Genome Safe Harbor Sites for Targeted Insertion The above identified 61 AX5707 candidate safe harbor sequence intervals were blasted against the publicly available B73 genome (AGPv3/RefGen_v3; available at the maize genetics and genomics database website (Andorf et al., 2016. "MaizeGDB update: new tools, data and interface for the maize model organism database." Nucleic Acids Res, 44(d1): D1195-201). Only sequences shared between both B73 and AX5707 genomes with a minimum length of 1,500 bp were selected for further evaluation. Among them, only 1 or 2 of the best candidates from each chromosome were selected. As a result, 10 candidate safe harbor site sequences were selected for experimental validation of targeted insertion. Chromosome 9 and 10 did not have suitable sequence remaining as candidates. The potential safe harbors are described in Table 2. Table 2 indicates the genomic position of the safe harbor in both the AX5707 genome and the B73 genome. The B73 genomic locations are as found in the publicly available MAIZE_B73_REF_4 genome. These target maize genomic loci are particularly useful for targeted insertion of a DNA of interest, because each locus is present in the genome of more than one maize variety. Therefore, the target maize genomic locus is useful for targeted insertion of a DNA of interest into more than one variety of maize cell.

TABLE 2

Candidate safe harbor in AX5707 and B73 genomes

| Genome | Map | Safe harbor ID | Genome start position | Genome end position | Length (bp) | SEQ. ID. NO: |
|---|---|---|---|---|---|---|
| AX5707 | Chr_1 | SH_Chr1.1b | 325,437,387 | 325,434,968 | 2,420 | 8 |
| B73 | Chr_1 | SH_Chr1.1b | 270,485,529 | 270,483,110 | 2,420 | 62 |
| AX5707 | Chr_2 | SH_Chr2.1t | 25,144,470 | 25,146,195 | 1,726 | 9 |
| B73 | Chr_2 | SH_Chr2.1t | 20,384,387 | 20,386,397 | 1715 | 63 |
| AX5707 | Chr_3 | SH_Chr3.1b | 263,100,502 | 263,098,753 | 1,750 | 21 |
| B73 | Chr_3 | SH_Chr3.1b | 218,255,241 | 218,253,476 | 1,766 | 64 |
| AX5707 | Chr_4 | SH_Chr4.1t | 11,850,583 | 11,852,381 | 1,574 | 23 |
| B73 | Chr_4 | SH_Chr4.1t | 11,050,139 | 11,051,738 | 1,600 | 65 |
| AX5707 | Chr_5 | SH_Chr5.1t | 31,399,845 | 31,397,479 | 2,367 | 31 |
| B73 | Chr_5 | SH_Chr5.1t | 26,056,598 | 26,054,232 | 2,367 | 66 |
| AX5707 | Chr_6 | SH_Chr6.1b | 172,684,264 | 172,686,334 | 2,071 | 44 |
| B73 | Chr_6 | SH_Chr6.1b | 152,128,279 | 152,130,349 | 2,071 | 67 |
| AX5707 | Chr_7 | SH_Chr7.1t | 22,848,628 | 22,850,204 | 1,577 | 46 |
| B73 | Chr_7 | SH_Chr7.1t | 20,083,153 | 20,084,729 | 1,577 | 68 |
| AX5707 | Chr_7 | SH_Chr7.2b | 198,992,304 | 198,994,416 | 2,113 | 55 |
| B73 | Chr_7 | SH_Chr7.2b | 172,546,393 | 172,548,490 | 2,098 | 69 |
| AX5707 | Chr_8 | SH_Chr8.1t | 30,777,043 | 30,778,622 | 1,580 | 56 |
| B73 | Chr_8 | SH_Chr8.1t | 25,491,600 | 25,493,179 | 1,580 | 70 |
| AX5707 | Chr_8 | SH_Chr8.2b | 210,893,628 | 210,891,662 | 1,967 | 57 |
| B73 | Chr_8 | SH_Chr8.2b | 178,200,769 | 178,198,798 | 1,972 | 71 |

Example 3: Construction of CRISPR-Cas9 Expression and Targeting Donor Vectors The following example describes construction of vectors used for CRISPR-Cas mediated targeted insertion, using the CRISPR-associated site specific nuclease Cas9. It is well-known in the art that there are many different nuclease-mediated targeted insertion systems, including ZFNs, meganucleases, and TALENS. The examples disclosed here do not limit the invention to any particular system of targeted insertion.

To demonstrate that the selected candidate safe harbor sites can be used for targeted insertion, a 20-nucleotide target sequence, which is followed by a 5'-NGG PAM site, within each safe harbor site was chosen for designing a single guide RNA (sgRNA) to test Cas9-mediated cleavage and gene targeting (Table 3). Cas9 and sgRNA-mediated targeted insertion in maize cells have been previously described in the art (WO16106121, herein incorporated by reference). Similar Cas9 and sgRNA expression vector designs were used for testing candidate safe harbor sites here. Each Cas9-sgRNA expression vector (vector ID's shown in Table 3) comprises a coding sequence for a Cas9 nuclease, operably linked to a promoter at its 5' end and a terminator at its 3' end, and also comprises a coding sequence for a sgRNA comprising a target sequence which targets the Cas9 to a genomic nuclease cleavage site within the target maize genomic locus, also referred to as the safe harbor. The sgRNA is operably linked at its 5' end to a rice ubiquitin promoter and at its 3' end to a terminator. The sgRNA for each Cas9-sgRNA expression vector comprises a target sequence (SEQ ID NO: 72-81), as described in Table 3.

Donor vectors were also constructed to enable the targeted insertion of a DNA of interest at the target maize genomic locus to be mediated by homologous recombination. The donor vector may also be referred to as the donor molecule. A donor vector which contains at least one homologous "arm" flanking the 5' and/or the 3' end of the donor sequence can promote homologous recombination between the arm and the target genomic sequence, thereby leading to targeted insertion by homologous recombination. In these examples, the DNA of interest for each donor vector comprises the coding sequence for the selectable marker phosphomannose isomerase (PMI), which confers an ability to metabolize mannose (U.S. Pat. Nos. 5,767,378 and 5,994,629). The 5' end of the PMI coding sequence is operably linked to a rice actin promoter and the 3' end of the PMI coding sequence is operably linked to a terminator. Immediately 3' to the terminator is a homologous arm, comprising the sequence of SEQ ID NO: 82 to 91 for each corresponding safe harbor sequence, as described in Table 4. This homologous arm is sufficient to enable homologous recombination of the donor molecule into the target maize genomic locus at the cleaved genomic nuclease cleavage site. However, it will be appreciated by a person of skill in the art that the homologous arm can be of a different length, and/or that there can be an additional homologous arm adjacent to the DNA of interest at the 5' end. It will also be appreciated by a person of skill in the art that the presence of the homologous arm(s) enables homologous recombination, however the DNA of interest may still integrate into the genome within the target maize genomic locus by different means, such as non-homologous end joining. These described donor vectors enable CRISPR-Cas9 mediated insertion of the PMI

TABLE 3

Target sequences for CRISPR-Cas9 targeted insertion

| Safe harbor ID | Target sequence for Cas9-sgRNA vector design | Target sequence name | Target sequence SEQ.ID.NO. | Cas9-sgRNA vector ID | Cas9-sgRNA vector Alias |
|---|---|---|---|---|---|
| SHChr1.1b | 5'-AGCAC CGGTT GCTCG GACCG-3' | xZmSHChr1 | 72 | 23808 | SHChr1_Cas9 |
| SHChr2.1t | 5'-TACAG AAACG CGGAG AGACT-3' | xZmSHChr2 | 73 | 23811 | SHChr2_Cas9 |
| SHChr3.1b | 5'-TAACG AGCAG AGTAC ACACG-3' | xZmSHChr3 | 74 | 23812 | SHChr3_Cas9 |
| SHChr4.1t | 5'-TGAAA GCGAT GCGGT TTAGA-3' | xZmSHChr4 | 75 | 23813 | SHChr4_Cas9 |
| SHChr5.1t | 5'-TACAA TGTAC AGTCT AGCCA-3' | xZmSHChr5 | 76 | 23814 | SHChr5_Cas9 |
| SHChr6.1b | 5'-ACGAG ACCAT CCAAT GATCG-3' | xZmSHChr6 | 77 | 23815 | SHChr6_Cas9 |
| SHChr7.1t | 5'-TGGAG AGTAA TAGGA TGGCA-3' | xZmSHChr7a | 78 | 23816 | SHChr7a_Cas9 |
| SHChr7.2b | 5'-TGAAA CCAAA CCAGC AGACG-3' | xZmSHChr7b | 79 | 23817 | SHChr7b_Cas9 |
| SHChr8.1t | 5'-TAGGT TTGAC ATGTGCTAAG-3' | xZmSHChr1 | 80 | 23818 | SHChr8a_Cas9 |
| SHChr8.2b | 5'-CTTCG TAGAC ATATAGATGC-3' | xZmSHChr2 | 81 | 23819 | SHChr8b_Cas9 | expression cassette at a particular target maize genomic locus by homologous recombination.

As positive controls for targeted insertion, 3 vectors (23813, 23818 and 23819) were constructed for testing intermolecular recombination between donor vectors and the target maize genomic loci (referred to as "target site" in Table 4 below).

TABLE 4

Donor vectors for CRISPR-Cas9 targeted insertion

| Safe harbor ID | Cas9-sgRNA vector ID | Targeted insertion donor vector ID | Targeted insertion donor vector alias | Safe harbor sequence interval in the donor vector | Donor vector safe harbor sequence interval SEQ. ID. NO. |
|---|---|---|---|---|---|
| SHChr1.1b | 23808 | 23829 | SHChr1_donor_V2 | xJHAXSHChr1 | 82 |
| SHChr2.1t | 23811 | 23828 | SHChr2_donor_V2 | xJHAXSHChr2 | 83 |
| SHChr3.1b | 23812 | 23827 | SHChr3_donor_V2 | xJHAXSHChr3 | 84 |
| SHChr4.1t | 23813 | 23826 | SHChr4_donor_V2 | xJHAXSHChr4 | 85 |
| SHChr5.1t | 23814 | 23825 | SHChr5_donor_V2 | xJHAXSHChr5 | 86 |
| SHChr6.1b | 23815 | 23824 | SHChr6_donor_V2 | xJHAXSHChr6 | 87 |
| SHChr7.1t | 23816 | 23823 | SHChr7a_donor_V2 | xJHAXSHChr7a | 88 |
| SHChr7.2b | 23817 | 23822 | SHChr7b_donor_V2 | xJHAXSChr7b | 89 |
| SHChr8.1t | 23818 | 23821 | SHChr8a_donor_V2 | xJHAXSHChr8a | 90 |
| SHChr8.2b | 23819 | 23820 | SHChr8b_donor_V2 | xJHAXSHChr8b | 91 |
| Controls: Intermolecular recombination mediated CRISPR-Cas9 | | | | | |
| 23895, with SHChr4V2 target site | 23813 | 23826 | SHChr4_donor_V2 | xJHAXSHChr4 | 85 |
| 23890 with SHChr8aV2 target site | 23818 | 23821 | SHChr8a_donor_V2 | xJHAXSHChr8a | 90 |
| 23894 with SHChr8bV2_ target site | 23819 | 23820 | SHChr8b_donor_V2 | xJHAXSHChr8b v2 | 91 |

Example 4: Targeted Insertion into Target Maize Genomic Loci in Transiently Transformed Cells Targeted insertion of the donor PMI expression cassette transgene sequence into different target maize genomic loci mediated by RNA-guided Cas9 cleavage was tested by co-delivering a Cas9-sgRNA expression vector along with the corresponding donor vector (Tables 3 and 4) using particle bombardment, following techniques described previously for targeted insertion into the MIR604 insertion site, which is known to be a good safe harbor site (WO16106121). Briefly, a DNA vector comprising a Cas9-sgRNA expression cassette and a donor vector were precipitated onto gold particles (0.6 μm in diameter; Bio-Rad). A total of $2 \times 10^{10}$ molecules of Cas9-sgRNA expression vector and donor vector at 1:1 ratio were added to a tube of 20 μl prepared gold-glycerol slurry (60 mg/ml) and mixed well by finger tapping. 100 μL of $CaCl_2$ (2.5 M), and 10 μL of spermidine (0.1 M) were successively added and mixed by vortexing at room temperature. The mixture was then incubated on ice for 30 minutes. The DNA-coated particles were pelleted by centrifuging at 13,000 rpm for 1 minute. After discarding the supernatant, the particles were washed with 200 μL of absolute ethanol by vortexing for 30 seconds, centrifuging for 1 minute, and removing the supernatant and re-suspended in 20 μL of absolute ethanol. For each bombardment, 6 μL of the particle suspension was pipetted onto the center of macrocarriers. Bombardments of 3-day-old pre-cultured immature embryos in osmoticum medium were carried out using a Biolistic particle acceleration device (PDS 1000/He, Bio-Rad) under a chamber pressure of 27.5 mm of Hg at distances of 8, 10, and 65 mm from the rupture disc to the macrocarriers to the stopping screen to the target, respectively, with 1100 psi helium pressures and 3 shots per plates. The combination of Cas9-sgRNA vector, donor vector and numbers of target explants are listed in Table 5. Three days after bombardment, 25 bombarded embryos from each plate were removed for DNA extraction and PCR analysis to determine if targeted insertion of the DNA of interest (PMI expression cassette) into the safe harbor loci in the transformed cells was successful. Two samples were collected for each plate. Positive control experiments with sequences of targeted maize genomic loci cloned into vectors and co-delivered with their respective donors and Cas9-sgRNA expression vectors into maize cells were also performed to assay extra-chromosomal intermolecular recombination.

TABLE 5

Targeted insertion of target genomic loci by CRISPR-Cas9

| Safe harbor ID | Cas9 vector | Donor vector | Total # of embryos | # of embryos for 1st PCR | Explants to mannose selection | # of mannose resistant callus |
|---|---|---|---|---|---|---|
| SHChr1.1b | 23808 | 23829 | 153 | 25 × 2 | 103 | 18 |
| SHChr2.1t | 23811 | 23828 | 134 | 25 × 2 | 84 | 10 |
| SHChr3.1b | 23812 | 23827 | 155 | 25 × 2 | 105 | 35 |
| SHChr4.1t | 23813 | 23826 | 140 | 25 × 2 | 90 | 21 |
| SHChr5.1t | 23814 | 23825 | 121 | 25 × 2 | 71 | 21 |
| SHChr6.1b | 23815 | 23824 | 153 | 25 × 2 | 103 | 27 |
| SHChr7.1t | 23816 | 23823 | 161 | 25 × 2 | 111 | 16 |
| SHChr7.2b | 23817 | 23822 | 150 | 25 × 2 | 100 | 32 |
| SHChr8.1t | 23818 | 23821 | 158 | 25 × 2 | 108 | 13 |
| SHChr8.2b | 23819 | 23820 | 132 | 25 × 2 | 82 | 31 |
| Positive control 1: 23895, with SHChr4V2 target site | 23813 | 23895 | 135 | 25 × 2 | N.A. | N.A. |
| Positive control 2: 23890 with SHChr8aV2 target site | 23818 | 23890 | 132 | 25 × 2 | N.A. | N.A. |
| Positive control 3: 23894 with SHChr8bV2 target site | 23819 | 23894 | 121 | 25 × 2 | N.A. | N.A. |

Example 5: Molecular Demonstration of Targeted Insertion into Selected Safe Harbor Loci in Transiently Transformed Cells Genomic DNA was extracted from bombed maize embryo samples using Promega's Magnesil paramagnetic particles (www.promega.com). PCR primers were designed across the expected 5' and 3' homologous recombination junctions for detecting the targeted insertions (Table 6). For each of the expected recombination site, one primer was designed against a genomic sequence of the safe harbor interval, outside the targeted insertion site. The second primer (SEQ ID NO: 105) was designed against a sequence of the donor PMI expression cassette (Table 6). Table 6 also indicates the expected PCR product if targeted insertion was successful. Primers were also designed for the positive controls to assay intermolecular recombination.

TABLE 6

PCR primers for targeted insertion assay

| Safe harbor ID | SEQ ID NO. of genomic primer | Cas9-sgRNA vector ID | Donor vector ID | Expected PCR product (bp) |
|---|---|---|---|---|
| SHChr1.1b | 92 | 23808 | 23829 | 1603 |
| SHChr2.1t | 93 | 23811 | 23828 | 1603 |
| SHChr3.1 t | 94 | 23812 | 23827 | 1746 |
| SHChr4.1t | 95 | 23813 | 23826 | 1545 |
| SHChr5.1t | 96 | 23814 | 23825 | 1532 |
| SHChr6.1b | 97 | 23815 | 23824 | 1563 |
| SHChr7.1t | 98 | 23816 | 23823 | 1490 |
| SHChr7.2b | 99 | 23817 | 23822 | 1633 |
| SHChr8.1t | 100 | 23818 | 23821 | 1454 |
| SHChr8.2b | 101 | 23819 | 23820 | 1497 |
| 23895, with SHChr4V2 target site | 102 | 23813 | 23826 | 1559 |
| 23890 with SHChr8aV2 target site | 103 | 23818 | 23821 | 1598 |
| 23894 with SHChr8bV2_ target site | 104 | 23819 | 23820 | 1513 |

To detect targeted insertions in the transiently transformed embryos, two sequential PCR reactions were carried out on each sample to detect potential recombination products using PCR primers designed to amplify across the expected 5' and 3' homologous recombination junctions for detecting the targeted insertions (Table 6). The first PCR reaction was setup with 12.5 ul of Sigma JumpStart™ REDTaq ReadyMix™ Reaction Mix, 1 μl of each primers, 4 μl of gDNA and 6.5 μl of H2O. The second PCR reaction was setup with 12.5 μl of Sigma JumpStart™ REDTaq ReadyMix™ Reaction Mix, 1 μl of each primers, 2 μl of the first PCR product as template and 8.5 μl of H2O. PCR was performed on Applied Biosystems Veriti 96 Well Thermal Cycler with following amplification parameters: 95° C. for 5 minutes, 35 cycles of (95° C. 30 seconds, 55° C., 57° C. or 60° C. for 30 seconds as needed and 72° C. for 2 minutes), followed by 7 minutes at 72° C. and then hold at 4° C. until gel electrophoresis. After PCR, 10 μl of PCR product was run on a 1% agarose gel containing SyBR Safe DNA Gel Stain for visualization. PCR products of expected sizes were observed clearly in targeting experiments of 5 safe harbor sites, such that a call could be made regarding the successful targeted integration (Table 7). PCR products were cleaned up with EXO-SAP treatment before sending to Sanger sequence and subjected to Sanger sequencing. Sequencing analysis was carried out using SEQUENCHER™ software, and the sequence data was compared to the reference sequence. These results confirmed successful targeted insertion of the PMI expression cassette into the target genomic loci (SHChr5.1t and SHChr7.1t).

TABLE 7

Analysis of transiently transformed maize embryos for targeted insertion

| Safe harbor ID | # of bombed embryos | PCR results | Sequence results confirming targeted insertion? |
|---|---|---|---|
| SHChr1.1b | 50 | − | No data |
| SHChr2.1t | 50 | + | No |
| SHChr3.1 t | 50 | − | No data |
| SHChr4.1t | 50 | − | No data |
| SHChr5.1t | 50 | + | Yes, confirmed the linkage of PMI to region flanking xJHAXSHChr5 |
| SHChr6.1b | 50 | +/−? | No |
| SHChr7.1t | 50 | + | Yes, confirmed the linkage of PMI to region flanking xJHAXSHChr7a |
| SHChr7.2b | 50 | + | No |
| SHChr8.1t | 50 | − | No data |
| SHChr8.2b | 50 | − | No data |

Example 6: Targeted Insertion into Selected Safe Harbor Sites in Stably Transformed Cells The remaining explants from each plate after sampling at 3 days post-bombardment were transferred onto callus induction media for 10 days. Induced calli were then transferred onto mannose selection media. After 4 weeks of culturing in mannose-contained medium the PMI resistant calli were individually sampled, subjected to DNA extraction and PCR analysis. The numbers of mannose resistant callus were list in Table 8. Genomic DNA was extracted separately from maize embryo and callus tissue. Two sequential PCR reactions were carried out on each sample to detect potential recombination products as described above for transient targeting assays (Table 6 and Table 7). The results of PCR and Sanger sequence analysis are summarized in Table 8. Positive PCR products of expected sizes were found in 6 of 10 tested safe harbor loci. Sanger sequence analysis further confirmed targeted insertion in 3 (SHChr4.1t, SHChr5.1t and SHChr6.1b) out of the 10 target maize genomic loci tested in stably transformed callus tissues. It should be noted that negative PCR or sequencing results do not mean that these safe harbor loci are not amenable to targeted insertion; only very limited experiments were done with each safe harbor locus.

TABLE 8

Analysis of stably transformed tissue for targeted insertion

| Safe harbor ID | # of calli sampled | PCR results | Sequence results confirming targeted insertion? |
|---|---|---|---|
| SHChr1.1b | 18 | no positive | No data |
| SHChr2.1t | 10 | 6 positive | No |
| SHChr3.1 t | 35 | 1 positive | No |
| SHChr4.1t | 21 | 1 positive | Yes, confirmed the linkage of PMI to region flanking xJHAXSHChr4 |
| SHChr5.1t | 21 | 1 positive | Yes, confirmed the linkage of PMI to region flanking xJHAXSHChr5 |
| SHChr6.1b | 27 | 1 positive | Yes, confirmed the linkage of PMI to region flanking xJHAXSHChr6 |
| SHChr7.1t | 16 | 12 positive | No |
| SHChr7.2b | 32 | No positive | No data |
| SHChr8.1t | 14 | No positive | No data |
| SHChr8.2b | 31 | No positive | No data |

What is claimed is:

1. A method of integrating DNAs of interest into a target maize genomic locus in a maize genome, wherein the target maize genomic locus comprises a nucleic acid sequence having at least 100 contiguous nucleotides of SEQ ID NO: 67 or the complement thereof, comprising introducing into a maize cell:
   a) a first nucleic acid molecule comprising at least 100 contiguous nucleotides of SEQ ID NO: 67 or the complement thereof, and further comprising the DNA of interest; and
   b) a second nucleic acid molecule comprising a nucleotide sequence encoding a nuclease for site-directed cleavage at a genomic nuclease cleavage site within the target maize genomic locus, under conditions wherein expression of the second nucleic acid molecule can occur to produce the nuclease and the nuclease can cleave the nucleotide sequence at the genomic nuclease cleavage site, whereby the DNA of interest is integrated into the target maize genomic locus in the maize genome.

2. The method of claim 1, wherein two or more DNAs of interest are inserted into two or more targeted maize genomic loci.

3. The method of claim 1, wherein the DNAs of interest is inserted into the target maize genomic locus via homologous recombination.

4. The method of claim 1, wherein the DNAs of interest is inserted into the target maize genomic locus via non-homologous end-joining.

5. The method of claim 1, wherein the DNAs of interest and/or the target maize genomic locus are modified during the insertion of said DNA of interest into said target maize genomic locus.

6. A method of producing a maize plant, plant part, or progeny thereof comprising a DNA of interest, comprising regenerating a maize plant from the maize cell produced by the method of claim 1.

7. A maize plant, plant part, or progeny thereof comprising a DNA of interest, produced by the method of claim 6.

8. A method of making a maize plant cell comprising a DNA of interest, said method comprising:
   a. selecting a target maize genomic locus, wherein the target maize genomic locus comprises a nucleic acid sequence having a sequence selected from the group consisting of SEQ ID NO: 67, and the complement thereof;
   b. selecting a site specific nuclease that specifically binds to and cleaves a genomic nuclease cleavage site within said target maize genomic locus;
   c. introducing said site specific nuclease and a DNA of interest into the maize plant cell;
   d. allowing the DNA of interest to insert into the target maize genomic locus; and
   e. selecting maize plant cells that comprise the DNA of interest inserted into the target maize genomic locus.

9. The method of claim 8, wherein two or more DNAs of interest are inserted into two or more targeted maize genomic loci.

10. The method of claim 8, wherein the DNA of interest is inserted into the target maize genomic locus via homologous recombination.

11. The method of claim 8, wherein the DNA of interest is inserted into the target maize genomic locus via non-homologous end-joining.

12. The method of claim 8, wherein the DNAs of interest and/or the target maize genomic locus are modified during the insertion of said DNA of interest into said target maize genomic locus.

13. The method of claim 8, wherein the site specific nuclease is a Cas-associated nuclease and wherein a third nucleic acid molecule encoding a guide RNA is introduced into the maize cell.

14. The method of claim 8, wherein the site specific nuclease is a Cas-associated nuclease and wherein a third nucleic acid molecule comprising a guide RNA is introduced into the maize cell.

15. A method of producing a maize plant or plant part, or progeny thereof, comprising a transgene integrated into a genomic nuclease cleavage site in the maize genome, comprising regenerating a maize plant from the maize cell produced by the method of claim 8.

16. A maize plant or plant part, or progeny thereof, comprising a transgene integrated into a genomic nuclease cleavage site in the maize genome, produced by the method of claim 15.

17. A maize recombinant molecule, wherein the recombinant molecule comprises a nucleic acid sequence of at least 100 nucleotides and has at least 100 contiguous nucleotides of SEQ ID NO: 67 or the complement thereof, and wherein the recombinant molecule further comprises a DNA of interest, wherein the DNA of interest is inserted into the nucleic acid sequence to produce said recombinant molecule.

18. The recombinant molecule of claim 17, wherein the recombinant sequence comprises a nucleic acid sequence of at least 1 Kb and has a sequence of SEQ ID NO: 67 or the complement thereof.

19. A maize plant, plant part, or plant cell comprising the recombinant molecule of claim 17.

* * * * *